(12) United States Patent
Martin

(10) Patent No.: US 11,504,029 B1
(45) Date of Patent: Nov. 22, 2022

(54) MOBILE CONTROL USING GAIT CADENCE

(71) Applicant: David Martin, San Francisco, CA (US)

(72) Inventor: David Martin, San Francisco, CA (US)

(*) Notice: Subject to any disclaimer, the term of this patent is extended or adjusted under 35 U.S.C. 154(b) by 0 days.

(21) Appl. No.: 16/505,629

(22) Filed: Jul. 8, 2019

Related U.S. Application Data

(63) Continuation-in-part of application No. 14/922,174, filed on Oct. 25, 2015, now Pat. No. 10,342,462, and a continuation-in-part of application No. 14/932,591, filed on Nov. 4, 2015, and a continuation-in-part of application No. 15/296,868, filed on Oct. 18, 2016, and a continuation-in-part of application No. 16/044,833, filed on Jul. 25, 2018, and a continuation-in-part of application No. 16/275,323, filed on Feb. 14, 2019.

(60) Provisional application No. 62/750,292, filed on Oct. 25, 2018, provisional application No. 62/068,685, filed on Oct. 26, 2014, provisional application No. 62/090,698, filed on Dec. 11, 2014, provisional application No. 62/249,371, filed on Nov. 2, 2015.

(51) Int. Cl.
*A61B 5/11* (2006.01)
*A61B 5/00* (2006.01)

(52) U.S. Cl.
CPC ............ *A61B 5/112* (2013.01); *A61B 5/1126* (2013.01); *A61B 5/6802* (2013.01); *A61B 5/72* (2013.01); *A61B 2562/0219* (2013.01)

(58) Field of Classification Search
CPC ......... A61B 5/112; A61B 5/6802; A61B 5/72; A61B 5/1126; A61B 2562/0219
See application file for complete search history.

(56) References Cited

U.S. PATENT DOCUMENTS

| | | | |
|---|---|---|---|
| 7,457,719 B1* | 11/2008 | Kahn | A61B 5/1118 702/141 |
| 8,021,270 B2 | 9/2011 | D'Eredita | |
| 8,109,890 B2 | 2/2012 | Kamiar | |
| 8,206,325 B1 | 6/2012 | Najafi | |
| 8,764,532 B1 | 7/2014 | Berme | |
| 8,812,258 B2 | 8/2014 | Nadkarni | |
| 9,165,113 B2 | 10/2015 | Greene | |
| 9,599,819 B2 | 3/2017 | Alaniz | |
| 9,974,478 B1 | 5/2018 | Brokaw | |
| 2002/0028003 A1* | 3/2002 | Krebs | G06K 9/00348 382/115 |
| 2004/0015103 A1 | 1/2004 | Amininan | |
| 2004/0167420 A1 | 8/2004 | Song | |
| 2005/0192516 A1 | 9/2005 | Takiguchi | |

(Continued)

OTHER PUBLICATIONS

Nounou, Mohamah N. "Enhanced state estimation using multiscale Kalman filtering", Dec. 15, 2006, IEEE 45 conference on decision and control, pp. 1679-1684.

(Continued)

*Primary Examiner* — Rene T Towa

(57) ABSTRACT

Methods for controlling an aspect of an application in a mobile or wearable device and a mobile or wearable device user's representation in real time are described, where the user is performing a gait activity with a gait cadence, and the gait cadence is used for control. Additional user's mobility characteristics leveraged for control may include velocity and stride length, and the sensors utilized to obtain any contextual information may be accelerometers.

20 Claims, 18 Drawing Sheets

(56) References Cited

U.S. PATENT DOCUMENTS

| | | | |
|---|---|---|---|
| 2005/0234309 A1 | 10/2005 | Kiapper | |
| 2007/0074619 A1* | 4/2007 | Vergo | G10H 1/42 |
| | | | 84/612 |
| 2008/0146968 A1 | 6/2008 | Hanawaka | |
| 2009/0124938 A1 | 5/2009 | Brunner | |
| 2009/0131224 A1* | 5/2009 | Yuen | A63B 22/00 |
| | | | 482/3 |
| 2009/0137933 A1 | 5/2009 | Liberman | |
| 2010/0053322 A1 | 3/2010 | Marti | |
| 2010/0191697 A1* | 7/2010 | Fukumoto | A61B 5/1116 |
| | | | 706/54 |
| 2010/0280792 A1 | 11/2010 | Paiva Velhote Correia | |
| 2011/0009241 A1 | 1/2011 | Lane | |
| 2011/0118554 A1 | 5/2011 | Stakutis | |
| 2011/0190593 A1 | 8/2011 | McNair | |
| 2011/0196262 A1 | 8/2011 | McLeod | |
| 2011/0231101 A1 | 9/2011 | Bidargaddi | |
| 2011/0270573 A1 | 11/2011 | Chiou | |
| 2011/0288811 A1 | 11/2011 | Greene | |
| 2011/0313705 A1 | 12/2011 | Esser | |
| 2012/0041702 A1 | 2/2012 | Toda | |
| 2012/0089330 A1 | 4/2012 | Hesch | |
| 2012/0136573 A1* | 5/2012 | Janardhanan | G01C 21/165 |
| | | | 701/512 |
| 2012/0144916 A1 | 6/2012 | Doheny | |
| 2012/0303271 A1 | 11/2012 | Chowdhary | |
| 2013/0023798 A1 | 1/2013 | Greene | |
| 2013/0041291 A1 | 2/2013 | Soubeyrat | |
| 2013/0069862 A1 | 3/2013 | Ur | |
| 2013/0072807 A1 | 3/2013 | Tran | |
| 2013/0090881 A1* | 4/2013 | Janardhanan | G06F 1/163 |
| | | | 702/104 |
| 2013/0110010 A1* | 5/2013 | Fuke | A61B 5/1117 |
| | | | 600/595 |
| 2013/0123666 A1 | 5/2013 | Giuffrida | |
| 2013/0138388 A1 | 5/2013 | Jain | |
| 2013/0172691 A1 | 7/2013 | Tran | |
| 2013/0225288 A1 | 8/2013 | Levin | |
| 2013/0346014 A1 | 12/2013 | Nadkarni | |
| 2014/0088867 A1* | 3/2014 | Takaoka | G01C 21/16 |
| | | | 701/526 |
| 2014/0172361 A1 | 6/2014 | Chiang | |
| 2014/0247155 A1 | 9/2014 | Proud | |
| 2014/0275850 A1 | 9/2014 | Venkatraman | |
| 2014/0288679 A1 | 9/2014 | McNamee | |
| 2014/0288875 A1 | 9/2014 | Donaldson | |
| 2014/0309964 A1 | 10/2014 | Li | |
| 2014/0316305 A1 | 10/2014 | Venkatraman | |
| 2015/0009348 A1 | 1/2015 | Vartanian | |
| 2015/0018013 A1 | 1/2015 | Martin | |
| 2015/0100141 A1 | 4/2015 | Hughes | |
| 2015/0112603 A1 | 4/2015 | Zhong | |
| 2015/0133820 A1 | 5/2015 | Zohar | |
| 2015/0164377 A1 | 6/2015 | Nathan | |
| 2015/0181314 A1* | 6/2015 | Swanson | G01C 21/20 |
| | | | 340/870.07 |
| 2015/0213729 A1 | 7/2015 | Rhea | |
| 2015/0272511 A1 | 10/2015 | Najafi | |
| 2015/0332004 A1 | 11/2015 | Najafi | |
| 2015/0362520 A1 | 12/2015 | Wells | |
| 2015/0363965 A1 | 12/2015 | Wells | |
| 2016/0007888 A1* | 1/2016 | Nieminen | A61B 5/1118 |
| | | | 600/595 |
| 2016/0022141 A1 | 1/2016 | Mittal | |
| 2016/0034817 A1 | 2/2016 | Ali | |
| 2016/0038088 A1 | 2/2016 | Lari | |
| 2016/0113550 A1 | 4/2016 | Martin | |
| 2016/0166180 A1 | 6/2016 | Martin | |
| 2016/0169703 A1 | 6/2016 | Omr | |
| 2016/0189423 A1 | 6/2016 | Kaeser | |
| 2016/0271451 A1 | 9/2016 | Wu | |
| 2016/0317866 A1 | 11/2016 | Fung | |
| 2017/0122769 A1 | 5/2017 | Martin | |
| 2017/0188895 A1 | 7/2017 | Nathan | |
| 2017/0273601 A1 | 9/2017 | Wang | |
| 2017/0352240 A1 | 12/2017 | Carlton-Foss | |
| 2018/0177436 A1 | 6/2018 | Chang | |

OTHER PUBLICATIONS

Martin et al. "Determination of a patient's speed and stride length minimizing hardware requirements", May 25, 2011, IEEE 2011 international conference on body sensor networks, pp. 144-149.

Martin, E. "Real time patient's gait monitoring through wireless accelerometers with the wavelet transform", Jan. 19, 2011, IEEE, 2011 topical conference on biomedical wireless technologies, networks, and sensing systems, pp. 23-26.

Sayeed et al. "Comparison and adaptation of step length and gait speed estimators from single belt worn accelerometer positioned on lateral side of the body", Sep. 18 2013, IEEE, 2013 IEEE 8th international symposium on intelligent signal processing.

* cited by examiner

```
class AnimationView extends SurfaceView implements SurfaceHolder.Callback {
    class AnimationThread extends Thread implements SensorEventListener, OnTouchListener {
        Bitmap imagesStrip;
        long frame_0_StartTime;
        boolean beginning_manageCurrentFrame=true;
        long timeIntoCompleteAnimation;
        int frameCount=26;
        int completeAnimationPeriod=1000;// To be programmatically changed.
        int currentFrame=0;
        int frameWidth=300, frameHeight=360;
        Rect frameToDraw=new Rect(0,0,frameWidth,frameHeight);
        float personXPos=0, personYPos=0;
        RectF whereToDraw=new
            RectF(personXPos,personYPos,personXPos+frameWidth,personYPos+frameHeight);

//Additional code not included for clarity purposes.

public void manageCurrentFrame() {
            long time=System.currentTimeMillis();
            if (beginning_manageCurrentFrame && currentFrame==0) {
                frame_0_StartTime=time;
                beginning_manageCurrentFrame=false;
            }
            timeIntoCompleteAnimation=time-frame_0_StartTime;
            currentFrame=
        (int)(timeIntoCompleteAnimation*frameCount/completeAnimationPeriod)%frameCount;
            frameToDraw.left=currentFrame*frameWidth;
            frameToDraw.right=frameToDraw.left+frameWidth;
        }
```

FIG. 11A

```
private void doDraw(Canvas canvas) {
        manageCurrentFrame();
        canvas.drawBitmap(imagesStrip,frameToDraw,whereToDraw,null);
} public void setAnimationImagesStrip(int stripResource) {
        imagesStrip.recycle();
        imagesStrip=null;
        AssetManager assets=getResources().getAssets();
        InputStream buffer;
        String myFilename="";
        if (stripResource==0) {
                myFilename="firstImagesStripFile.png";
        } else if (stripResource==1) {
                myFilename="secondImagesStripFile.png";
        } else if (stripResource==2) {
                myFilename="thirdImagesStripFile.png";
        }
        try {
                buffer=new BufferedInputStream(assets.open(myFilename));
                imagesStrip=BitmapFactory.decodeStream(buffer);
        } catch (IOException e) {e.printStackTrace();}
        imagesStrip=
   Bitmap.createScaledBitmap(imagesStrip,frameWidth*frameCount,frameHeight,true);
    }
  }
}
```

FIG. 11B

```
public void onSensorChanged(SensorEvent event) {
    if(event.sensor.getType() == Sensor.TYPE_ACCELEROMETER) {
        double x_acceleration=(double)event.values[0];
        double y_acceleration=(double)event.values[1];
        double z_acceleration=(double)event.values[2];
        double signal_vector_module_acceleration=
                Math.sqrt((x_acceleration*x_acceleration)+
                (y_acceleration*y_acceleration)+(z_acceleration*z_acceleration));

double[] array_returned_from_determine_gait_parameters=
                determine_gait_parameters(x_acceleration,y_acceleration,
                z_acceleration,signal_vector_module_acceleration);
        double velocity=array_returned_from_determine_gait_parameters[0];
        double calories=array_returned_from_determine_gait_parameters[1];
        double cadence=array_returned_from_determine_gait_parameters[2];
        double activity= array_returned_from_determine_gait_parameters[3];

int previous_completeAnimationPeriodInMsec=completeAnimationPeriod;
        int new_completeAnimationPeriodInMsec=(int) (1000*2/cadence);
        if (new_completeAnimationPeriodInMsec!=previous_completeAnimationPeriodInMsec){
            long time_now = System.currentTimeMillis();
            frame_0_StartTime=time_now-(int)( new_completeAnimationPeriodInMsec *
            (timeIntoCompleteAnimation%previous_completeAnimationPeriodInMsec) /
            (double)previous_completeAnimationPeriodInMsec );
            completeAnimationPeriod=new_completeAnimationPeriodInMsec;
        }
    }
}
```

FIG. 13

MOBILE CONTROL USING GAIT CADENCE

CROSS REFERENCE TO RELATED APPLICATIONS

This application claims the benefits of U.S. provisional patent application No. 62/702,998, by David Martin, entitled "Leveraging mobility features for precise control", filed Jul. 25, 2018, and U.S. provisional patent application No. 62/750,292, by David Martin, entitled "Gait analysis applied for control", filed Oct. 25, 2018.

This application is a continuation-in-part of co-pending U.S. application Ser. No. 14/922,174, by David Martin, entitled "Application of Gait Characteristics for Mobile", filed Oct. 25, 2015, which claims the benefits of U.S. provisional patent application No. 62/068,685, by David Martin, entitled "Application of Gait Characteristics for Mobile", filed Oct. 26, 2014.

This application is also a continuation-in-part of co-pending U.S. application Ser. No. 14/932,591, by David Martin, entitled "Enhanced Real Time Frailty Assessment for Mobile", filed Nov. 4, 2015, which claims the benefits of U.S. provisional patent application No. 62/090,698, by David Martin, entitled "Enhanced Real Time Frailty Assessment for Mobile", filed Dec. 11, 2014.

This application is also a continuation-in-part of co-pending U.S. application Ser. No. 15/296,868, by David Martin, entitled "Mobile device control leveraging user kinematics", filed Oct. 18, 2016, which claims the benefits of U.S. provisional patent application No. 62/249,371, by David Martin, entitled "Mobile device control leveraging user kinematics", filed Nov. 2, 2015.

This application is also a continuation-in-part of co-pending U.S. application Ser. No. 16/044,833, by David Martin, entitled "Refined Control Leveraging Mobile Characteristics for health care", filed Jul. 25, 2018, which claims the benefits of at least U.S. provisional patent application No. 62/068,685, by David Martin, entitled "Application of Gait Characteristics for Mobile", filed Oct. 26, 2014.

This application is also a continuation-in-part of co-pending U.S. application Ser. No. 16/275,323, by David Martin, entitled "Mobile control using gait velocity", filed Feb. 14, 2019, which claims the benefits of at least U.S. provisional patent applications Nos. 62/651,409, 62/654,536, 62/702,998, and 62/750,292 by David Martin.

All of these applications are hereby incorporated by reference in their entireties for all purposes.

BACKGROUND

Field

This application relates to mobile and wearable devices, specifically to methodologies to leverage user's gait characteristics for control, focusing on gait cadence.

Discussion of Related Art

Common methods to obtain cadence by means of sensors embedded within mobile or wearable devices make use of thresholds, and detect steps when the value of a sensor signal reaches said thresholds. In order to achieve an accuracy improvement, the use of adaptable thresholds has also been proposed. Nevertheless, most of those approaches focus their analysis on the time domain, and although some methods make use of frequency analysis (e.g. using FFT to obtain the fundamental frequency of the signal), their algorithms still rely on thresholding in the time domain, making them prone to errors, especially with weak or noisy motion signals typical of walking. Recent studies with commercially available devices show large errors in the determination of the user's cadence, and those errors increase as the walking velocity decreases. In fact, considerable inaccuracies at low speeds may have important implications in health care applications. Consequently, there is a need for an enhanced methodology to accurately determine the cadence and other gait attributes (e.g. velocity, stride length, calories burned per time unit, activity) of mobile or wearable device users, and enable a new field of applications not possible with existing methodology. Among those applications, the control of a representation of the device user on the device screen, leveraging gait attributes such as velocity.

BRIEF DESCRIPTION OF THE DRAWINGS

FIG. 11A, 11B present schematic code to describe the control of elements displayed on the device screen to control the user's representation, according to one embodiment.

FIG. 13 presents schematic code to describe the implementation of the onSensorChanged method in a mobile application, according to one embodiment.

DETAILED DESCRIPTION OF EMBODIMENTS OF THE INVENTION

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term ' ' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning.

Some inventive functionality and inventive principles may be implemented with or in software programs or instructions and integrated circuits (ICs) such as application specific ICs. In the interest of brevity and minimization of any risk of obscuring the principles and concepts according to the present invention, discussion of such software and ICs, if any, is limited to the essentials with respect to the principles and concepts within some of the embodiments.

Figure 1A:
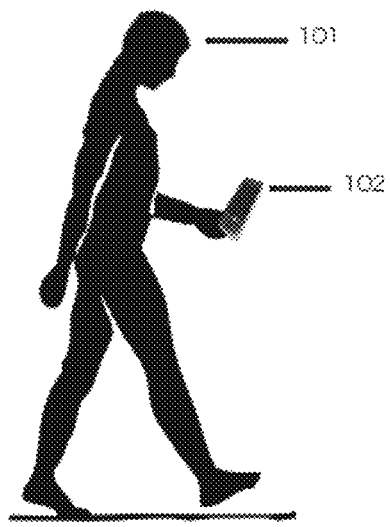
FIG. 1A represents an example of mobile device user walking with the device.
Figure 1B:
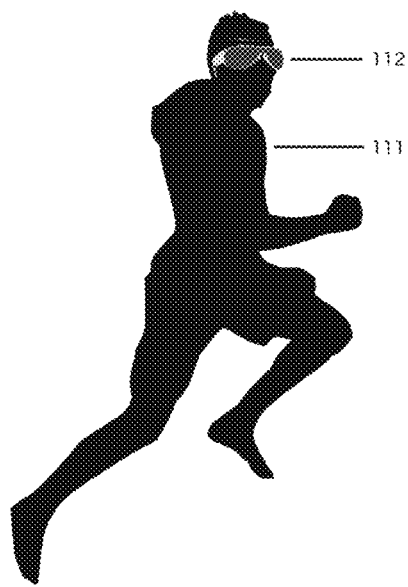
FIG. 1B represents an example of wearable device user running with the device.

FIG. 1A represents an individual, (101), walking with a mobile device, (102). In some embodiments, individual (101) may be performing any kind of walking, jogging, running, sprinting, or any other type of gait activity (including household activities. This Figure and its elements (510), (520), (530), (540), (550), (560), (570), and (580) are further described in U.S. application Ser. No. 14/922,174, by David Martin, entitled "Application of Gait Characteristics for Mobile", filed Oct. 25, 2015, and U.S. application Ser. No. 16/044,833, by David Martin, entitled "Refined Control Leveraging Mobile Characteristics for Health Care", filed Jul. 25, 2018, which are hereby incorporated by reference for all purposes. FIG. 1B represents an example of one embodiment in which individual (111) is running while wearing a device in the form of glasses (112). In some embodiments (112) may represent any type of virtual reality device, eyewear, glasses or any other type of wearable or mobile device that individual (111) is wearing in any way attached or positioned on his/her face, head, or any other place of his/her body. This Figure and its elements are further described in application Ser. No. 14/922,174 and application Ser. No. 16/044,833.

Figure 1C:
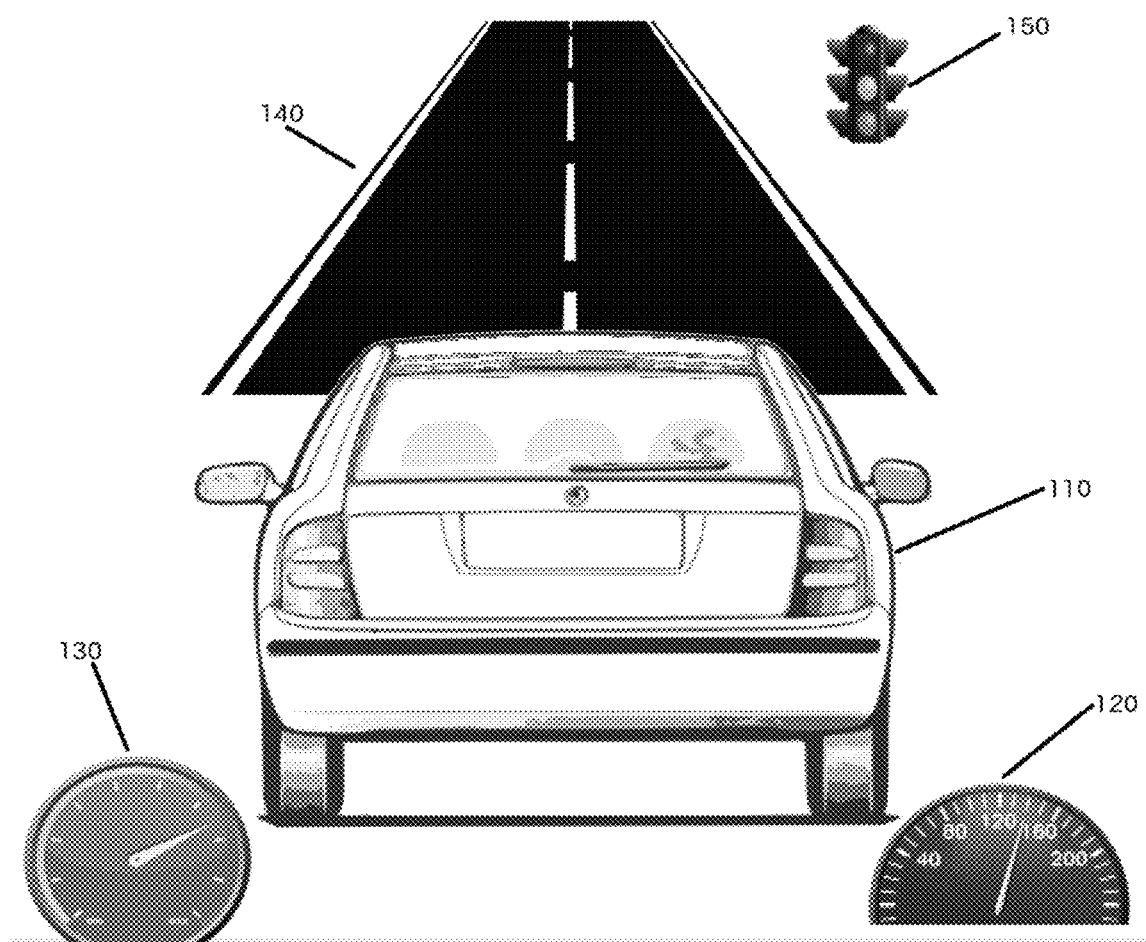
FIG. 1C illustrates an example of virtual environment displayed on the mobile or wearable device according to one embodiment.

In some embodiments, FIG. 1C may illustrate an example of screenshot of the display of devices (102) or (112), representing a virtual environment with which the individual (101) or (111) may interact. By way of example, and not limitation, the display may show a car (110) moving along a road (140) with some elements such as traffic lights (150). Moreover, the display may also show some dashboarb elements such as (120) or (130) to indicate certain magnitudes, variables or metrics of any kind. This Figure and its elements are further described in application Ser. No. 14/922,174 and application Ser. No. 16/044,833.

Figure 2A:
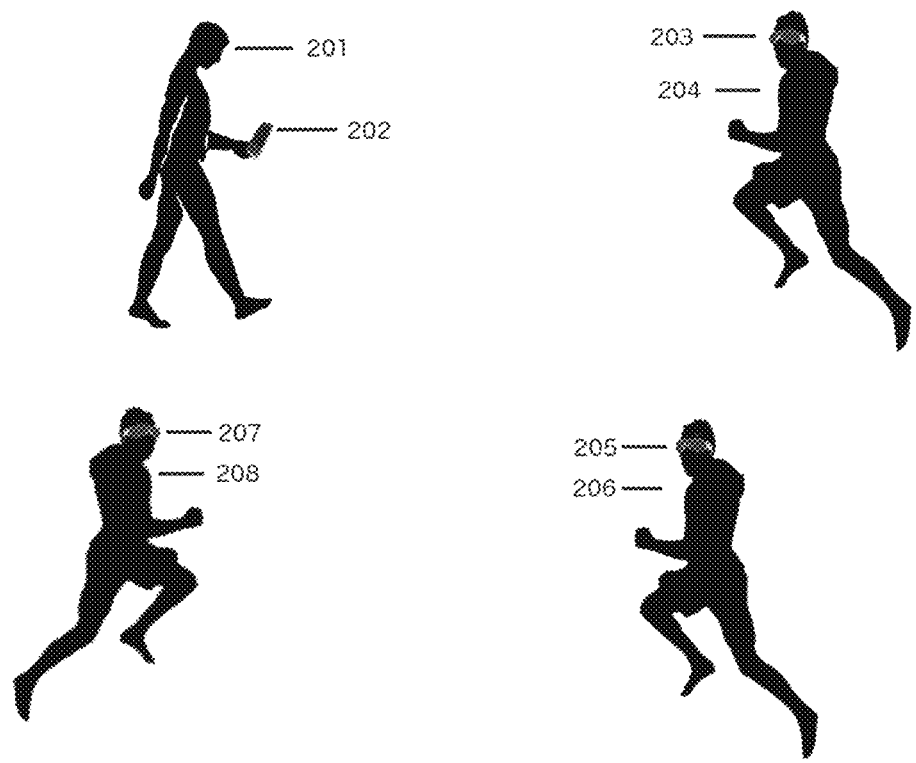
FIG. 2A represents an example of mobile and/or wearable device users performing some gait activity with their devices in a networking environment.

FIG. 2A represents an example of an embodiment in which four individuals (201), (204), (206), (208) participate in a networking environment; in this particular embodiment, each individual has one device: individual (201) is walking and has device (202), which may represent a smartphone, phablet, tablet, or any other type of device. Individual (204) is running and has device (203). In a similar way, individuals (206) and (208) are running and wearing their own devices (205) and (207) respectively. This Figure and its elements are further described in application Ser. No. 14/922,174 and application Ser. No. 16/044,833.

Figure 2B:
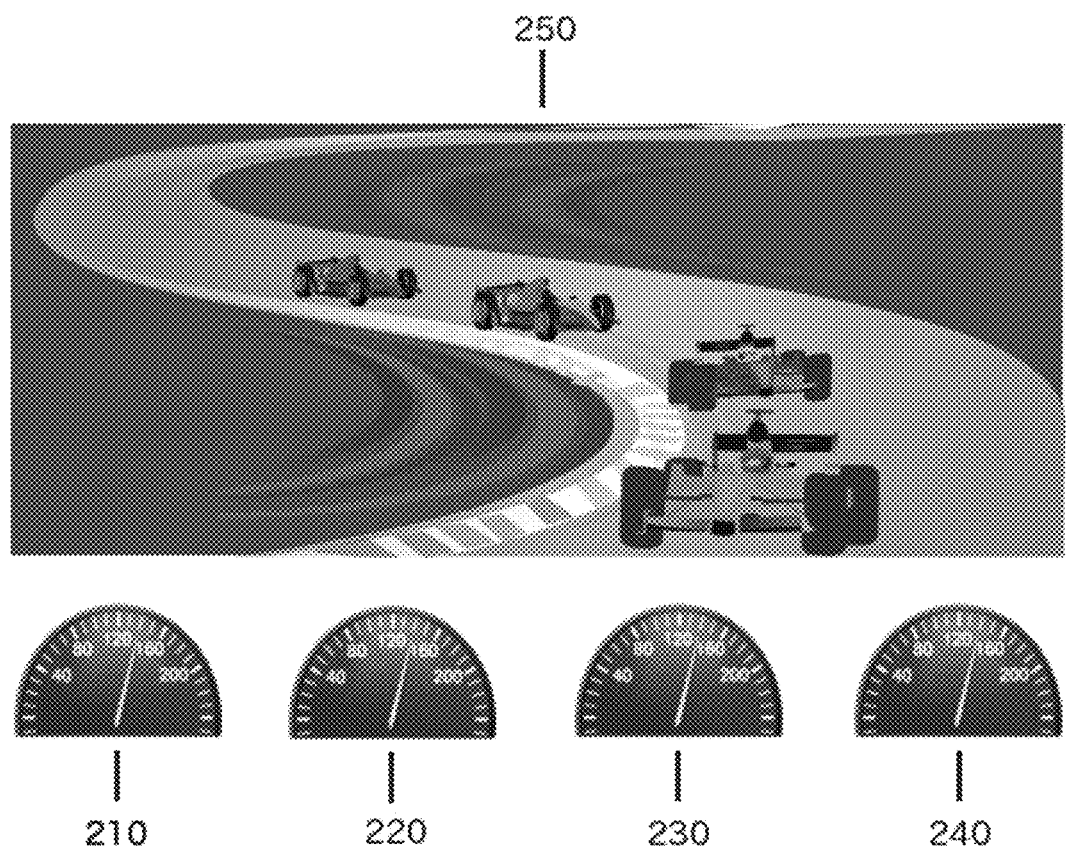
FIG. 2B illustrates an example of virtual environment displayed on the mobile and/or wearable devices in a networking environment according to one embodiment.

FIG. 2B represents an example of an embodiment illustrating an example of screenshot of the display of any or all of the devices (202), (203), (207) or (205). In a particular embodiment corresponding to a networking environment such as the one represented in FIG. 2A, FIG. 2B may represent an example of screenshot seen by individuals (201), (204), (206) and (208) in the display of any or all of their devices. This Figure and its elements (210), (220), (230), (240), and (250) are further described in application Ser. No. 14/922,174 and application Ser. No. 16/044,833.

Figure 3:
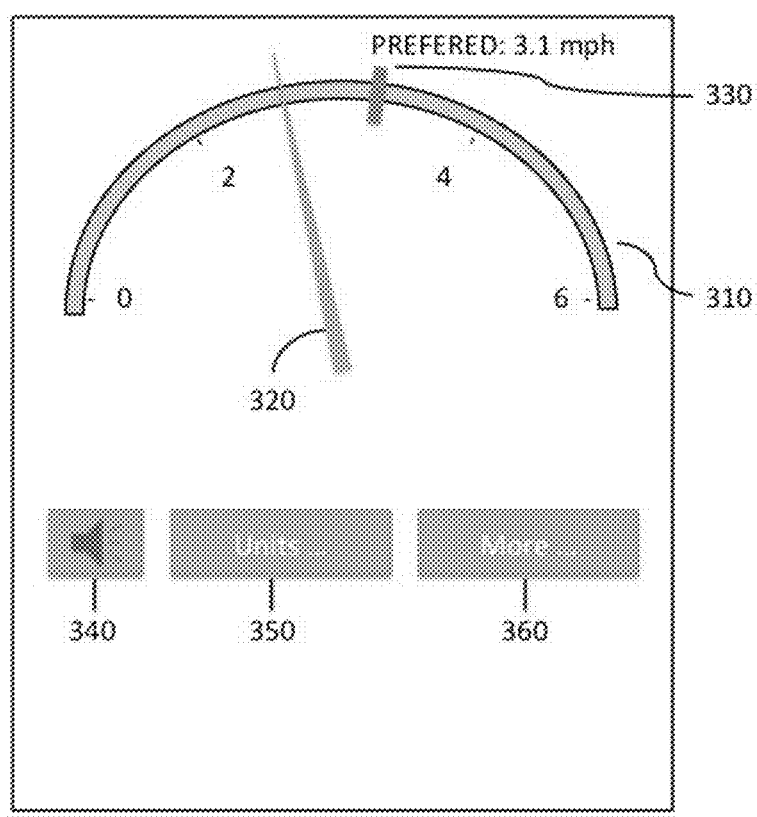
FIG. 3 shows an example of an embodiment of the presentation of contextual information on a mobile and/or wearable device.

In some embodiments, any contextual information may be displayed directly on the user's device display. By way of example and not limitation, the velocity of the user may be displayed in real time (typically, fractions of a second) on the mobile device display as shown in FIG. 3, which illustrates an example of the many possibilities. This Figure and its elements (310), (320), (330), (340), (350), and (360) are further described in application Ser. No. 14/922,174.

Figure 4:
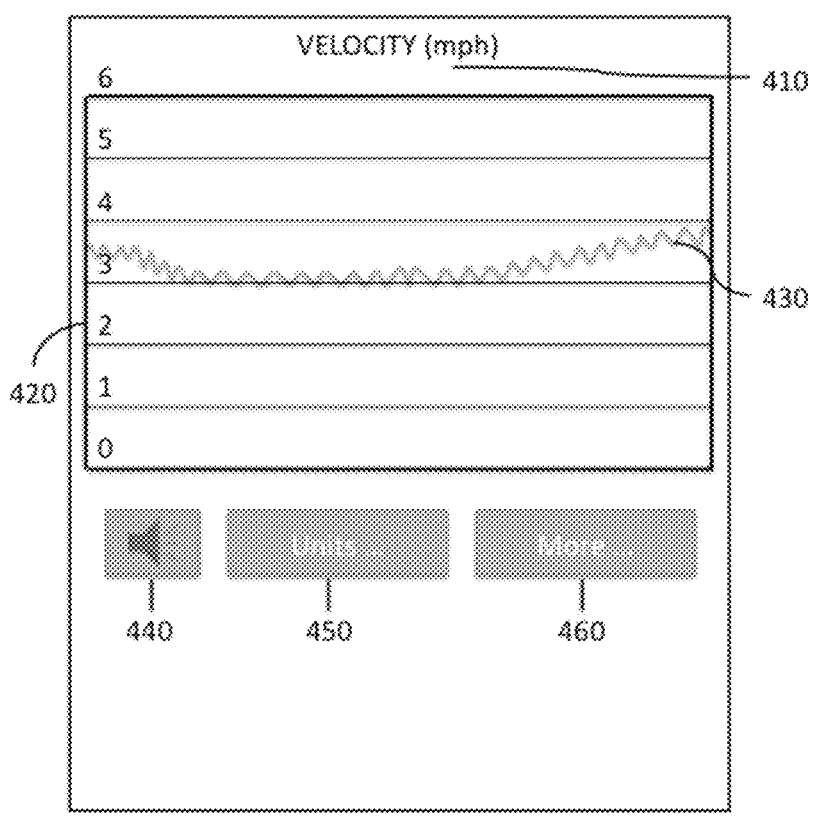
FIG. 4 shows an example of another embodiment of the presentation of contextual information on a mobile and/or wearable device.

FIG. 4 represents an embodiment of a representation of the user's velocity; in other embodiments, any other contextual information and/or gait characteristic or attribute (e.g. stride length, cadence, calories burned, etc. and combinations thereof) or related information may be represented. This Figure and its elements (410), (420), (430), (440), (450), and (460) are further described in application Ser. No. 14/922,174 and application Ser. No. 16/044,833.

Figure 5A:
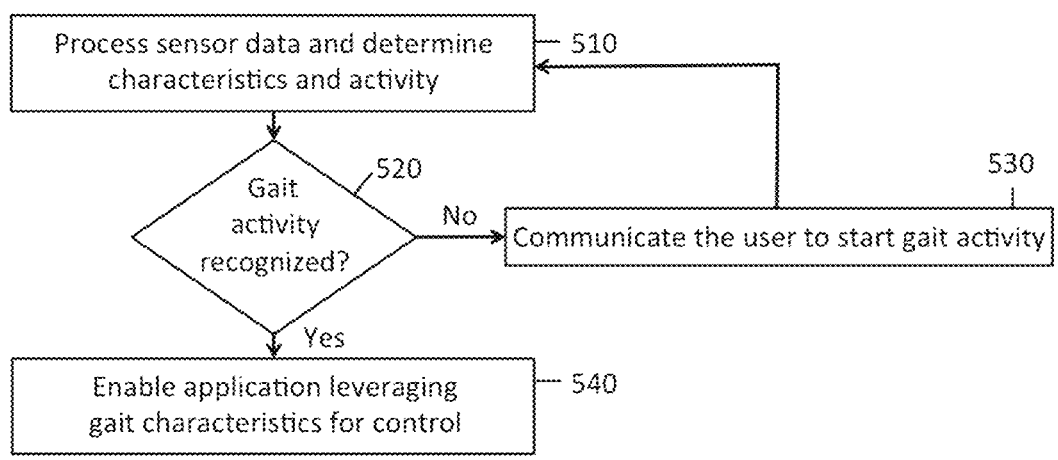
FIG. 5A presents a process flow diagram of an embodiment enabling and controlling an application with the user's gait characteristics.

FIG. 5A represents a flow diagram of possible basic steps of some embodiments enabling and controlling an application with the user's gait characteristics (including cadence, stride length, velocity, calories burned per time unit, activity, device position and/or any other and/or any variations and/or combinations thereof). This Figure and its elements (510), (520), (530), and (540) are further described in application Ser. No. 14/922,174 and application Ser. No. 16/044,833.

Figure 5B:
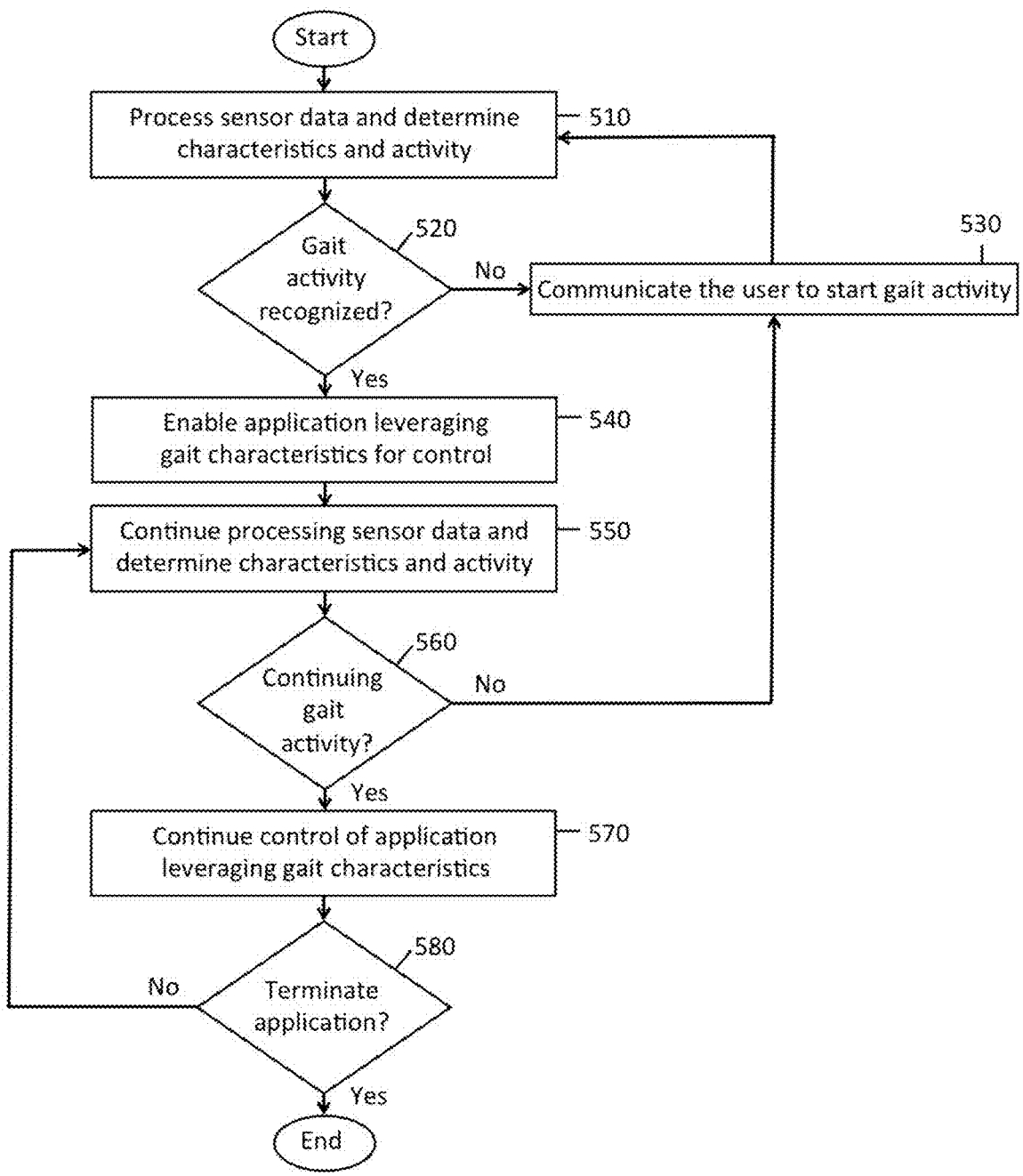
FIG. 5B presents a process flow diagram of another embodiment enabling and controlling an application with the user's gait characteristics.

FIG. 5B represents an extension of the flow diagram of possible basic steps from FIG. 5A that may be applicable to other embodiments. This Figure and its elements (510), (520), (530), (540), (550), (560), (570), and (580) are further described in application Ser. No. 14/922,174 and application Ser. No. 16/044,833.

Figure 6:
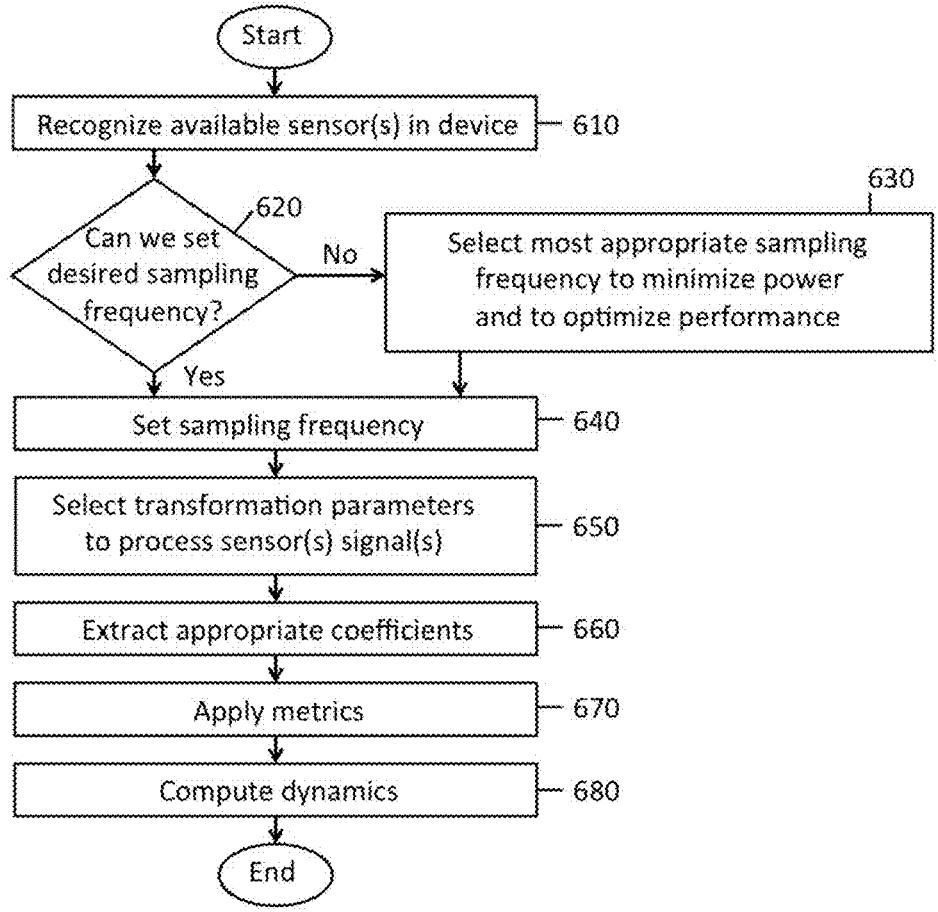
FIG. 6 illustrates a process flow diagram for the user's dynamics information determination according to one embodiment.

FIG. 6 illustrates a flow diagram of one embodiment with possible basic steps of a method for providing a user's dynamics information. In some embodiments, dynamics information may include, by way of example without limitation, velocity, activity, cadence, stride time, stride length, caloric consumption, calories burned per time unit, device position, kinetic energy, etc. and/or any combinations and/or variations thereof. This Figure and its elements (610), (620), (630), (640), (650), (660), (670), and (680) are further described in application Ser. No. 14/922,174 and application Ser. No. 16/044,833.

In some embodiments, an indication of the fundamental frequency or cadence of the gait of a mobile or wearable device user, may be determined through the analysis of a motion sensor signal (e.g. the motion sensor can be a tri-axial accelerometer embedded within the device, and the signal vector module may be analyzed), by means of a Fourier transformation of said signal over a time window. By way of example without limitation, choosing a time window of four seconds (some embodiments may use windows with different time lengths, including by way of example without limitation, 2, 4, 6, 8, 20, 40 seconds or any other amount of seconds) for the motion sensor signal, the Fourier transformation of said signal may provide a representation of its frequency components; in some cases, the strongest frequency component in said representation may coincide with the fundamental frequency of the user's gait or cadence; however, it must be noted that in some conditions, the analysis through the Fourier transformation may deliver misleading results, and special considerations may need to be taken into account to correct those results; by way of example without limitation, the combination of Fourier transformation with other techniques (e.g. wavelet transformation, Hilbert transformation, peak counting, correlation, autocorrelation, thresholding in time domain, and/or any other and/or combinations thereof) may help increase the accuracy in the determination of the user's cadence. By way of example without limitation, a cadence solution obtained through Fourier transformation analysis can be confirmed or rejected by a cadence solution obtained independently by any other technique (in case of rejection, priority can be given, for example, to the solution closest to the past (previous processing) cadence value); and in case of several techniques being used, a majority vote could be employed to decide on the final solution in case of discrepancies. Additional examples of combinations of techniques to obtain cadence are included in the rest of this specification. Any variations of any said elements and/or parameters and/or techniques and/or procedures and/or any combinations thereof may also be possible.

In some embodiments, an indication of the fundamental frequency of a motion sensor signal (or an indication of the cadence of a mobile or wearable device user's gait) can be determined by means of an autocorrelation of the motion sensor signal over a time window. By way of example without limitation, selecting the motion sensor signal over a four seconds time window and performing an autocorrelation of said signal, delivers another signal (for clarity purposes, called second signal, which typically consists of a central maximum surrounded by secondary minima and maxima), from which the inverse of the time distance between the central maximum of said second signal and the largest secondary maximum of said second signal, represents an indication of the fundamental frequency of the original motion sensor signal over said four seconds time window. Some embodiments may use a different length of the time window (e.g. two seconds, six seconds, eight seconds, twenty seconds, sixty seconds, or any other length based on criteria comprising computational costs, dynamism of the solution, accuracy of the solution, frequency content, update frequency, and/or any others). Some embodiments may use different approaches to obtain the previously called second signal, comprising by way of example without limitation, a further division of the signal by its variance, and/or using a pre-processing phase to filter the original motion sensor signal at a particular frequency band (e.g. using a dynamic filter whose central frequency is updated over time based on a previously determined fundamental frequency of the motion signal obtained by means of a frequency transformation; or using the wavelet transformation to filter the motion signal over a range of frequency bands, in response to an indication that the mobile device has experienced a substantial orientation change, wherein said indication is obtained through the analysis of the motion signal with the Fourier transformation), and/or pre-conditioning the original motion sensor signal with any type of filter in any way, and/or using a pre-processing phase to offset the original motion signal in any direction by any amount, and/or using a post-processing phase to perform any of the previously mentioned approaches to reverse some or all of those changes, or to amplify some or all of said changes, or for any other purposes; criteria to follow any of these approaches include: increased accuracy, optimization of computational costs, increased dynamism in the solution, or any other. In some embodiments, any of the mentioned and/or any other additional approaches/methods/techniques/elements/processes and/or any variations and/or any combinations thereof may be used during the pre-processing, post-processing, and in-processing stages, in any way, for any purposes, and according to any criteria.

In some embodiments, the motion sensor leveraged to obtain the user's gait cadence may be an accelerometer; in some embodiments, the motion sensor may be a single-axis accelerometer; in some embodiments, the motion sensor may be a triaxial accelerometer, and each one of the axis may be used independently; in other embodiments, the motion sensor may be a triaxial accelerometer embedded within the device, and the three axial components may be leveraged to obtain a signal vector module; in other embodiments, the motion sensor may be a triaxial accelerometer, and the three axial components may be leveraged to obtain different combinations of correlations, which may be processed to obtain the fundamental frequency of the motion of the device; by way of example without limitation, some embodiments may use the correlation between accelerations of x and y axis and/or the correlation between x and z axis, and/or the correlation between y and z axis, and analyze the resulting signals in the time domain (e.g. event detection by means of thresholding using a moving average of the signal as threshold) or in the frequency domain (e.g. leveraging Short Time Fourier Transform), or by means of any other approach or combinations thereof (e.g. leveraging the wavelet transformation to obtain both time and frequency information of the signal), or any other techniques and/or combinations thereof for any purposes.

In some embodiments, the motion sensor may be embedded within the device; in other embodiments, the motion sensor may be in a wearable unit independent from the mobile device, and positioned in any way and in any location; in some embodiments the motion sensor may be a gyroscope; in other embodiments the motion sensor may comprise an accelerometer (uni-axial or tri-axial) and/or a gyroscope (uni-axial or tri-axial) and/or a magnetometer (uni-axial or tri-axial) and any sensor fusion techniques (e.g. Kalman filtering, particle filtering, or any other) may be leveraged to increase the accuracy of the solution or for any other purposes; in other embodiments, any or all of the mentioned sensors (accelerometer and/or gyroscope and/or magnetometer) may be embedded within the mobile device, and/or independently positioned in any location by means of separate wearable units in any way. Some embodiments may use any combinations of any of the previously mentioned approaches, and/or aspects, and/or elements, and/or processes, and/or any other, in any fashion.

In some embodiments, the time window considered to process the motion sensor signal may be offset over time in any fashion as additional samples from said motion sensor keep arriving for processing. By way of example without limitation, a four seconds time window may overlap 50% with the next four seconds time window selected for the next processing; in other words, the last half of the first time window coincides with the first half of the second time window. In other embodiments, different lengths of time window (e.g. 2, 4, 6, 20, 40 seconds or any other amount of seconds) and/or different overlapping factors and/or different approaches and/or combinations thereof may be used for the continuous processing of the motion sensor signal. In another example of embodiment, a four seconds time window may be selected to process the motion sensor signal every half a second, regardless of the motion sensor sampling frequency (downsampling, upsampling, filtering, and/or any other technique and/or combinations thereof may be leveraged to adapt to particular hardware and/or software conditions); in this example, the overlapping factor is larger than in the previous example, and the update frequency and dynamism (e.g. capability to quickly adapt to changes) of the solution have increased. In some embodiments, any possible overlapping factor, length of time window, update frequency, dynamism of the solution, and/or any other element/feature and/or combinations thereof may be selected. By way of example without limitation, a fixed length time window may be selected and said time window may be offset every time a new sample arrives from the motion sensor (accepting the new arriving sample and discarding the oldest sample from the fixed length time window (again, downsampling, upsampling, filtering, and/or any other technique and/or combinations thereof may be leveraged to adapt to particular hardware and/or software conditions, if needed)), in such a way that the update frequency of the solution may be equal to the sampling frequency of the motion sensor; in other words, we may obtain the fundamental frequency (or cadence) of a mobile device user with an update frequency equal to the motion sensor sampling rate; in some embodiments, by way of example without limitation, the device motion sensor sampling rate may be equal to 60 Hz, or 120 Hz, thus obtaining an update frequency for the user's cadence greater than the user's step frequency; this is an important aspect for certain applications requiring increased dynamism in the solution (for example to control an aspect of an application or to control a process in a mobile device with the user's cadence, with an update frequency greater than the user's step frequency, thus improving the user's experience over other approaches). In other embodiments, we may work with any other motion sensor sampling rates and leverage upsampling, downsampling, filtering or any other technique to obtain an update frequency for the user's cadence higher or lower than the user's step frequency.

In some embodiments, during the processing of the original motion sensor signal (e.g. signal from an accelerometer within the device) over a time window to determine the fundamental frequency (or cadence) using autocorrelation, a pre-processing phase may be included to filter said motion sensor signal in any fashion (e.g. filter as a result of a frequency analysis, e.g. Fourier analysis or any other, of said signal); by way of example without limitation, said signal may be applied a Fourier transformation from where the frequency components of said signal may be analyzed; in particular, focusing on the frequency components below a threshold of, for example, 0.5 Hz, and above 0 Hz, if these low frequency components are stronger than the rest of frequency components of the signal (e.g. their amplitudes in the Fourier transformation domain are larger than the amplitudes of the rest of frequency components of said Fourier transformation above 0.5 Hz), that may indicate a substantial orientation change experienced by the device.

The term substantial orientation change may be defined in some embodiments, by way of example without limitation, as any orientation change (in any number of dimensions) experienced by a mobile device that causes low frequency components other than those due to gravity (e.g. below a threshold of 0.5 Hz but larger than 0 Hz) of an accelerometer signal (the accelerometer being within said device), to have an amplitude (as observed, for example, through a Fourier transformation of said signal) larger than the rest of frequency components above the threshold of 0.5 Hz. In other embodiments, the threshold of 0.5 Hz to refer to low frequencies may be modified (made larger or smaller, but always keeping the sense of low frequencies in the context of gait analysis in which typical fundamental frequencies may approximately range from 1 Hz to 4 Hz), and the condition to be fulfilled by the amplitude of said low frequencies in comparison with the rest of frequencies may be relaxed (e.g. the maximum amplitude of said low frequencies may be above 80% (or 120% or any other figure that may depend on a plurality of criteria) of the maximum amplitude of any other frequency outside the low frequencies range); in some embodiments, different metrics/figures may be leveraged to refer to approximately the same term. By way of example without limitation, the term low frequencies may refer in some embodiments to the frequencies below the typical lower limits in the values of gait cadence (e.g. below 1 Hz) without considering frequencies due to gravity (typically 0 Hz); in some embodiments the upper threshold for low frequencies may be lower (e.g. below 0.5 Hz, or below 0.3 Hz, or any other value), and the term low frequencies may refer to any frequency that may allow the detection of a substantial orientation change experienced by the device, keeping the sense of low frequencies in the context of gait analysis in which typical fundamental frequencies may approximately range from 1 Hz to 4 Hz. In some embodiments, for example, if the upper threshold for low frequencies is very small (e.g. 0.3 Hz) and the Fourier transformation of the accelerometer signal offers low granularity in the selection of frequency components (e.g. there is only one low frequency component below said threshold and above 0 Hz), the detection of a substantial orientation change experienced by the device may comprise the comparison of the amplitude of that only low frequency with the amplitudes of the other frequency components obtained through the Fourier transformation. By way of example without limitation, frequency bands rather than setting thresholds may be used to refer to low frequencies or any other frequencies (e.g. in some embodiments, the low frequency amplitude(s) may be compared with a subset (e.g. a range of frequencies comprising the strongest amplitudes, or a range of frequencies comprising the previous values of cadence, or a range of frequencies comprised between certain thresholds, etc.) of the other frequency amplitudes); or energies of frequency components (either precise, specific frequency components or whole frequency bands or sub-bands, or any other) rather than amplitudes may be used; or any other possible modification and/or combination of any of the mentioned concepts/elements or any other may be used in other embodiments.

Substantial orientation changes may typically occur for example during movements and/or shakes performed by the user while carrying the device in his/her hand during a gait activity. In some embodiments, substantial orientation changes may refer to any type of orientation change experienced by the mobile or wearable device that distorts, and/or introduces noise in, and/or introduces artifacts in, and/or influences, and/or modifies the underlying information in the motion sensor signal about the gait movement, in any way. By way of example without limitation, said low frequency components due to a substantial orientation change may be strong enough to hide or distort or introduce noise or negatively influence or alter in any other way the underlying information relative to the original gait movement (e.g. the low frequency components may be so strong that an original fundamental frequency of e.g. 1.6 Hz may appear very weak (even negligible) in comparison with said low frequency components, to the extent that it could be interpreted that the fundamental frequency is now, for instance, 0.5 Hz instead of the real 1.6 Hz; any other type of distortions may also be considered. In cases of substantial orientation change, the original motion sensor signal may be filtered and/or processed in any fashion (e.g. by means of hardware and/or software) to mitigate and/or attenuate and/or counteract and/or influence in any way the distortion and/or noise and/or artifacts and/or influence and/or modification introduced by said substantial orientation change in the underlying gait information.

By way of example without limitation, as a result of a detection of a substantial orientation change, some embodiments may use a filter (e.g. high pass, or band pass) of any type (e.g. Butterworth, Chebyshev, or any other) or apply any type of pre-processing to try to eliminate the frequency components below 0.5 Hz (or any other threshold) from said motion sensor signal before being processed to determine the fundamental frequency. Taking into account the excellent qualities of wavelet transformation to, for instance, filter dynamic signals minimizing any extra distortion, we may apply a wavelet transformation to the original motion sensor signal (typical transformation parameters may be selected; by way of example without limitation: a mother wavelet from any of Haar, or Daubechies, or Coiflets, or discrete version of Meyer; and a number of levels of decomposition sufficient to account for the frequency bands we expect, which may depend on the number of signal samples we have, the length of the time window, or the sampling frequency; in a particular example, we may apply the wavelet transformation to the original motion signal using Haar mother wavelet and eight levels of decomposition; in another example, we may apply the wavelet transformation to the original motion signal using Daubechies type 3 mother wavelet and six levels of decomposition); once the wavelet transformation coefficients are obtained, a wavelet reconstruction may be applied avoiding low frequency components/coefficients (getting rid of any other frequency component may also be possible and convenient in certain conditions); by way of example without limitation, the avoided low frequency components/coefficients may include those below the previously mentioned threshold of 0.5 Hz. In other words, we filter the original motion sensor signal leveraging a wavelet transformation by obtaining its wavelet transformation coefficients and applying a wavelet reconstruction avoiding coefficients corresponding to frequencies below 0.5 Hz; in this way, the wavelet reconstruction performed with all coefficients but those corresponding to low frequencies will be a filtered version of the original motion signal. Consequently, in this particular example, we are determining in real time the device user's cadence through the analysis of the motion sensor signal by means of a combination of techniques comprising: Fourier transformation (e.g. to analyze the frequency components of the motion sensor signal and decide if the signal needs to be filtered), wavelet transformation (to filter the signal), and autocorrelation of the filtered signal. In some embodiments, any modifications and/or combinations of any of the elements and/or processes and/or techniques mentioned and/or any other, may be applied in any fashion.

In some embodiments, abrupt changes in cadence (or motion sensor signal fundamental frequency) may be detected leveraging frequency and time information of the motion sensor signal. By way of example without limitation, abrupt changes in cadence may be characterized by sudden and/or fast (typically within a few seconds or even within fractions of a second) modifications in the value of said cadence; and wherein said abrupt modifications typically involve a relative change in the value of said cadence of at least 25% (e.g. a change from 2 Hz to 1.5 Hz involves a reduction of 25% relative to 2 Hz), although other values, larger and/or smaller, may also be considered. By way of example without limitation, abrupt changes in cadence may comprise: a change from 2 Hz to 1 Hz in the walking cadence of a mobile device user in a matter of 2 seconds, or a change from 2.1 Hz to 1.2 Hz in the walking cadence of a mobile device user in a matter of 2 steps, or a change from 0.8 Hz to 1.5 Hz in the walking cadence of a mobile device user in a matter of 3 steps, or a change from 1.9 Hz to 3.35 Hz in the gait cadence of a mobile device user in a matter of 1.5 seconds while he/she changes his/her gait from walking to running, or a change from 3.2 Hz to 1.8 Hz in the gait cadence of a mobile device user in a matter of 3.5 seconds while he/she changes his/her gait from running to walking, or any other possible combinations reflecting an important change in the value of the cadence (e.g. a factor of approximately 2 or less or more when the cadence is increased, and/or a factor of approximately 0.5 or less or more when the cadence is decreased) performed in a short period of time (typically within a few seconds).

Traditional approaches to determine cadence may fail when facing abrupt changes in cadence, because their processing of the motion signal may assume, for instance, a selected minimum time length of the user's step, or a selected frequency range of the user's cadence; the problem may be specially important when the abrupt changes in cadence (e.g. from 1 Hz to 2 Hz) result in the new cadence value (2 Hz) occupying some harmonic frequency of the previous values of cadence (1 Hz), in such a way that traditional methods may think of the new cadence value (2 Hz) as an harmonic of the previous cadence value (1 Hz), and find a subharmonic (½) of the new cadence (2 Hz) to be considered as the real cadence because it matches previous cadence values (1 Hz); consequently, traditional approaches would keep wrongly tracking said subharmonic as the fundamental frequency. Other examples may comprise any possible combinations and/or modifications of any of the concepts (including harmonics, subharmonics, and their orders) and/or figures and/or elements of the previous examples. It is worth noting that the problems may also arise with changes in cadence not necessarily involving integer multiples and/or submultiples of the original fundamental frequency.

In some embodiments, abrupt changes in the device user's cadence may be detected leveraging frequency and time information of the motion sensor signal (e.g. accelerometer signal, wherein said accelerometer is within the device). By way of example without limitation, we consider a mobile or wearable device user walking, and transitioning his/her cadence from 0.5 Hz to 1 Hz (other examples of embodiments may use different cadence values), whereby the device comprises a triaxial accelerometer with a sampling frequency of 50 Hz; the new value of 1 Hz for cadence has been determined (810) using e.g. any of the approaches described in this specification, but the new value is suspicious of being an error, because of the abrupt change in cadence (820). Consequently, there is a need to confirm as genuine the new cadence value, or reject it because it may be considered that the newly determined cadence is an error caused by harmonics of the previous cadence value (0.5 Hz). In other words, there is a need to detect genuine abrupt changes in cadence, and thus confirm as genuine the newly determined value of cadence. For this, a process composed of several stages will be explained next.

First, a pre-processing stage may comprise the identification of the accelerometer axis whose mean has the highest absolute value among the three axes, and/or the identification of two of the accelerometer axes whose means have the lowest absolute value among the three axes (830) (e.g. we identify the three axes of the accelerometer X, Y, and Z, and obtain the mean in the time domain for each one of them over a time window of, for example, four seconds (some embodiments may use windows with different time lengths, including e.g. 2, 6, 20, 40 seconds or any other amount of seconds); we obtain the absolute value of said obtained means, and compare them to identify the two accelerometer axes with the lowest means in absolute value; other embodiments may use any other length of time window or any other modifications according to criteria comprising: computing and/or storing costs and/or any other; other embodiments may use any other approaches and/or modifications and/or combinations thereof).

Once the two axes with the lowest means in absolute value have been identified (e.g. axes X and Y), an indication of a metric accounting for the average frequency value of the main (strongest) frequency components recorded over a pre-determined time window may be obtained for each of said two axes (840); for instance, said metric may be computed over a time window comprising the past twenty seconds; in some embodiments, different lengths of time window may be used (larger or shorter depending on criteria comprising accuracy, computing and storing costs, etc.), or different variables may be used for continuous updating of said metric with every new measurement/sample/processing obtained from the accelerometer signal, in such a way that there is no need to keep a window of past values; in other embodiments, different metrics may be used; for example, probabilistic models can be used to obtain a metric accounting for the strength/power and/or frequency value of each main frequency component recorded and the length of time during which said component was active; in other embodiments the metric may account for the frequency value of said component and the amount of time said value has been active over a length of time; other embodiments may use any combinations of any of said elements and/or concepts and/or any others in any fashion. For clarity purposes, we can call said determined indications X_probabl_freq and Y_probabl_freq (for X and Y axes respectively); in some embodiments, said determined indications may be retrieved leveraging any of the previously described approaches and/or using small databases, and/or registers, and/or look-up tables, and/or any kind of variables recording continuous updates in an application.

After determining said indications X_probabl_freq and Y_probabl_freq, the two previously identified axes (e.g. axes X and Y), are classified according to said indications (850); for example, if axis X has a value of said determined indication larger than axis Y, we can call axis X as primary axis and axis Y as secondary axis. Next, to check if there has been a genuine abrupt transition in the fundamental frequency, we focus (860) on a range of frequencies around the previously determined fundamental frequency (0.5 Hz), and we check if the current strength of the so called primary axis in a frequency band around the previously determined fundamental frequency is at least a threshold below the current strength of the so called secondary axis in the same frequency band (870); this strength comparison can be performed in terms of energy (e.g. using energy of a frequency component or energy of a frequency band, which can be determined for example leveraging a Fourier transformation or a wavelet transformation), or in terms of amplitude (e.g. using amplitude of a frequency component which can be determined for example through a Fourier transformation), or in terms of any other concept and/or element and/or any combinations thereof. Regarding the threshold for the strength comparison, recommended values for increased accuracy may be, by way of example without limitation: the larger quantity should be at least 2.25 times the smaller quantity if the comparison is made in terms of energies, or the larger quantity should be at least 1.5 times the smaller quantity if the comparison is made in terms of amplitudes; in some embodiments, different values (larger or smaller) may be used to account for particular conditions that may recommend tightening or relaxing said threshold. In some embodiments, any variations of any figures/concepts/approaches and/or any other and/or combinations thereof may be used.

In affirmative case regarding the previously referred strength comparison, we retrieve a history (880), over a pre-determined length of time right before the current time, of the values of the energies of both primary and secondary axes in the frequency band around the previously determined fundamental frequency (0.5 Hz); in some embodiments, said history of the values of the energies of both axes may span over several seconds (e.g. 10 seconds, although other values may also be possible depending on criteria comprising computing costs, storage costs, sampling frequency and/or any other), and it should be large enough to be able to register the transition. In some embodiments, instead of energies, the history of values may be of amplitudes of frequency components, obtained, for example, through the Fourier transform. In other embodiments, other approaches and/or figures and/or techniques and/or combinations thereof may be used.

Next, calling oldest_time_instant the instant of time corresponding to the oldest value registered in the previously mentioned history of values of strength (for clarity, it is worth remembering that strength can be expressed in terms of energy or amplitude or any other depending on the chosen approach), we check if the following three conditions are fulfilled: 1) the strength of the so called secondary axis over said frequency band at said oldest_time_instant is at least a threshold below the strength of the so called primary axis over the same frequency band at the same oldest_time_instant (881), and 2) the current strength of the so called primary axis in said frequency band is at least a threshold below the average strength of the primary axis in the same frequency band over the span of said history of values of strength (882), and 3) the current strength of the so called secondary axis in said frequency band is at least a threshold above the average strength of the secondary axis in the same frequency band over the span of said history of values of strength (883); if said three conditions are fulfilled, then some embodiments may consider that an abrupt transition in cadence has been detected (890), and consequently, the most recently determined fundamental frequency (1 Hz) is verified as genuine (891); otherwise, it would have been rejected (892) and some embodiments may use said rejection to try to keep tracking the old cadence values of 0.5 Hz (e.g. leveraging an adaptive filter centered at the old cadence values to emphasize them and reject what could be considered as errors due to harmonics, or with any other approach). Again, as previously described, regarding the threshold for the strength comparison, recommended values for increased accuracy may be, by way of example without limitation: the larger quantity should be at least 2.25 times the smaller quantity if the comparison is made in terms of energies, or the larger quantity should be at least 1.5 times the smaller quantity if the comparison is made in terms of amplitudes; in some embodiments, different values (larger or smaller) may be used to account for particular conditions that may recommend tightening or relaxing said threshold. In some embodiments, any variations of any figures/concepts/approaches and/or any other and/or combinations thereof may be used.

In some embodiments, a combination of time domain techniques and frequency domain techniques (e.g. Fourier transformation) may be used to detect abrupt changes in cadence; in other embodiments, techniques providing both time and frequency information (e.g. wavelet transformation) may be used; in other embodiments, combinations of any of those techniques and/or any other may be leveraged to obtain the time and frequency information to allow detection of abrupt changes in cadence. In other embodiments, any other modification and/or combination of any element and/or approach and/or technique and/or figure and/or combinations thereof may be used.

Some embodiments may leverage the previously mentioned information about the user's steps in combination with other metrics to enhance user's dynamics information, comprising velocity and activity. It is worth noting that in some embodiments, the user's cadence may be considered as the user's step frequency (inverse of the user's step time period). Some embodiments may leverage the obtained information on user's steps in combination with the information on user's dynamics to determine stride length. By way of example without limitation, using the physics principle velocity equals distance over time, once we have determined velocity, we can obtain distance (e.g. stride or step length) by using the time of each stride or step (step frequency (cadence) equals inverse of the user's step time period). Some embodiments may leverage the information on user's dynamics to compute distance. Some embodiments may enhance distance through the combination of user's dynamics information with localization information. Some embodiments may use different techniques, principles and/or methodologies to obtain all the previous information and metrics, including but not limited to machine learning. In some embodiments, all the computation, processing, information presentation, and other steps may be carried out within a single mobile device without the need of external resources. In some embodiments, the computation or some other step or combinations of steps may be performed external to the mobile device, or with the assistance of some external element, such as external sensor, server, database or any other element. In some embodiments, software may be stored on the mobile or wearable device, for instance, in its memory for execution by its processor or processors. Some embodiments may store data structures and code on computer readable storage medium, which by way of example, and not limitation, may comprise field-programmable gate arrays, application-specific integrated circuits, magnetic and/or optical storage devices, etc.

In some embodiments, the sensor portion of the device or the device itself or any other device containing a sensor and with the capability to communicate in any fashion with the user's device, or any other type of device or accessory may be positioned or attached to any part of the user, including by way of example without limitation, the wrist, arm, hand, face, head, waist, chest, pocket, hat, shoe, any type of clothing, accessories and any combinations thereof and in any way. In some embodiments, the system may be trained to recognize and/or learn activity, motion type, attachment position of the device, movement characteristic, etc. In some embodiments, analysis of acceleration signature may help determine activity, motion type, attachment position of the device, movement/gait characteristic, etc. By way of example without limitation, the acceleration signal may be processed to identify maximums, minimums, mean, standard deviation, frequency components, period, orientation, distribution of peaks, patterns, etc. and/or combinations thereof in order to help determine activity, motion type, attachment position of the device, movement/gait characteristic, etc. In some embodiments, Fourier analysis, any kind of filtering, peak counting, determination of frequency components leveraging the wavelet transform or any other method and combinations thereof may also be utilized to determine user's gait activity, characteristics, etc. In some embodiments, any type of prompt to the user may also be leveraged to request information about his/her activity, motion type, attachment position of the device, movement/gait characteristic, etc. In some embodiments, activity, motion type, attachment position, movement/gait characteristic, etc. may be determined through correlation of any type of sensor values or any type of parameter or metric generated with them, based on any type of model that has been calibrated in any fashion for a particular activity, motion type, attachment position, movement characteristic, etc. In some embodiments, any other sources, means, methods and/or configurations may be leveraged to determine activity, motion type, attachment position, movement/gait characteristic, etc., including by way of example without limitation, the use of sensors and/or signals obtained independently of the sensed acceleration (e.g. GPS), the use of statistics and/or any other empirical information, algorithms, databases or other information stored anywhere and in any fashion, combinations thereof, etc. In some embodiments, the referred methods, configurations, systems, etc. may be modified, updated and/or calibrated in any way, periodically or continuously over any time interval.

Some embodiments may include any external sources to obtain any parameter or information about movement, environment, context, etc. including by way of example without limitation, speed and/or distance monitors, any number of portable electronic devices (e.g. GPS receivers, any kind of computing and/or communications device, etc.), databases and/or networks. In some embodiments, other types of inputs may also be utilized, including by way of example without limitation, buttons, keys, keyboards, keypads, touchpads, joysticks, etc., which may be used in any fashion. Any type of satellite based navigation systems, cellular communications networks and other systems/networks may also be used to obtain speed in some embodiments (and/or provide feedback to help correct errors) under certain conditions.

In some embodiments, additional inputs may include traces from touch-sensitive screens, button presses, gesture recognition, voice commands, switches, and/or any other type of technological, physical or any nature means that allow the user to interact, and combinations thereof. In some embodiments, in addition to using gait characteristic for control, further control may be performed through any additional movements that the user may perform with the device, such as any type of tilting or any kind of gestures, including by way of example without limitation, any kind of raise, swing, twist, touch, press, swipe, drag, double touch, pinch, etc., and combinations thereof, regardless of performing them with or without direct contact to the device screen or any other element (e.g. the user may perform the pinch gesture touching a screen or in the air without touching a solid element). In some embodiments, any type of method may be employed to distinguish between different types of gestures, swings, twists, etc. that the user makes while he/she performs a pedestrian activity (e.g. walk, jog, run, etc.); by way of example without limitation, frequency analysis, filtering, acceleration thresholding, analysis of projection of gravity vector, feedback from other sensors, or any other technique/method and combinations thereof may be employed.

In some embodiments, the acceleration sensor may be an electrostatic or capacitance-coupling type, or any other technology (e.g. piezoelectric or piezoresistance type) now existing or later developed, and may be configured to deliver three-axis, two-axis, or one-axis acceleration. In some embodiments, in addition to accelerometers, any other type of technologies and/or sensors such as gyroscopes, magnetometers, pressure sensors, cameras, GPS, etc. may be used in any way to enhance accuracy or for any other purposes. In some embodiments, the user may have any number of any type of sensors, sensor units, devices, or accessories located anywhere in any fashion to determine the characteristics of his/her movement and/or for control or any other purposes.

In some embodiments, any processing, detection, recognition, or any other actions or operations may be performed regardless of the mode, state or any other condition of the device, application or any other entity, process or element. In other embodiments, any number of conditions and/or criteria of any type must be satisfied before proceeding with any of said actions or operations.

Any of the embodiments herein described may be implemented in numerous ways, including as a method, an apparatus, a device, a system, a computer readable medium, etc., and also be applicable in any environment, application (game, non-game, etc.), condition, etc. regardless of number of users, physical proximity, communication means, device, or any other factor.

Other configurations are also possible. By way of example, and not limitation, in some embodiments, all or part of the processes may be performed by chip-level systems, third-party applications, operating system kernel, firmware, or any other combination of hardware and/or software. In some embodiments, the software may be delivered in a variety of forms, including but not limited to, as stand-alone application, as library, as application programming interface, etc. In general, the functions of particular embodiments may be achieved by any means as is known in the art. Some embodiments may use distributed, networked sensors and/or systems, components, servers, databases, and/or circuits, and/or any combination of additional hardware and/or software and/or processing techniques and methodologies. Some embodiments may use any other type of sensor and/or system.

In some embodiments, sensors may be any of several types including, by way of example, and not limitation, any type of device, transducer or any other type of apparatus which may measure some quantity; in some embodiments, sensors may be implemented in any size, with any type of technique and technology, including but not limited to electronic, microelectronic, nanoelectronic, etc. By way of example, and not limitation, sensors may comprise any type of accelerometer, magnetometer, gyroscope, pressure sensor, proximity sensor, etc. and any other type of device sensitive to radio-frequency, sound, ultrasound, light, etc. including but not limited to, GPS antennas and/or their sensitive elements, WiFi antennas and/or their sensitive elements, and any other type of radio-frequency technology antennas and/or their sensitive elements. In some embodiments, sensors are integrated within the mobile or wearable device. In some embodiments, sensors or other mobile or wearable devices may be distributed outside the main mobile or wearable device, and they may communicate with the main mobile or wearable device by any means. Communication or transfer of data may be wired, wireless, or by any other means. In some embodiments, the user or other entity may rearrange characteristics of the components, or other features or elements of the system and the system may automatically adjust to new settings or arrangements.

Figure 7:
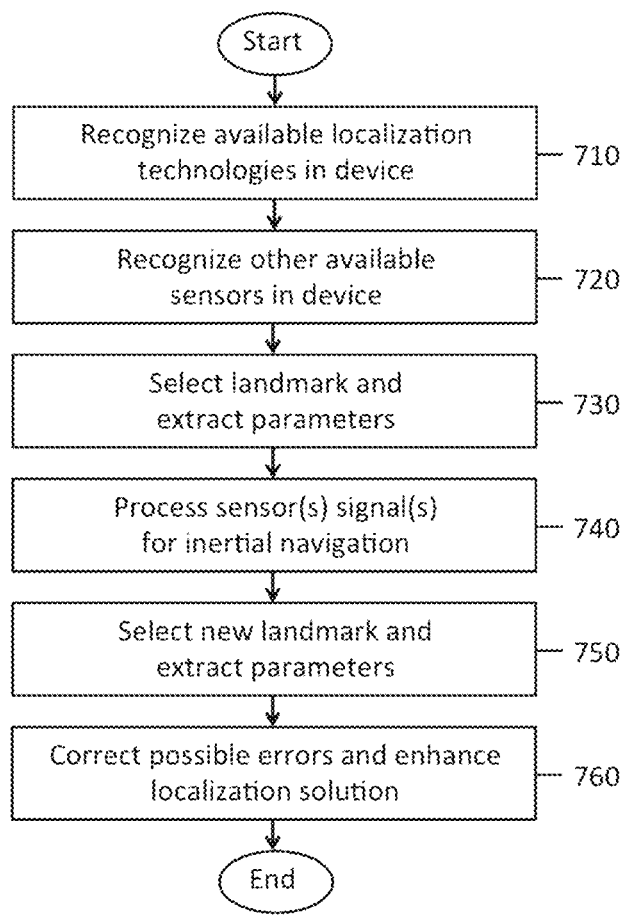
FIG. 7 illustrates a flow diagram for the process to enhance a user's dynamics and localization information according to one embodiment.
Figure 8:
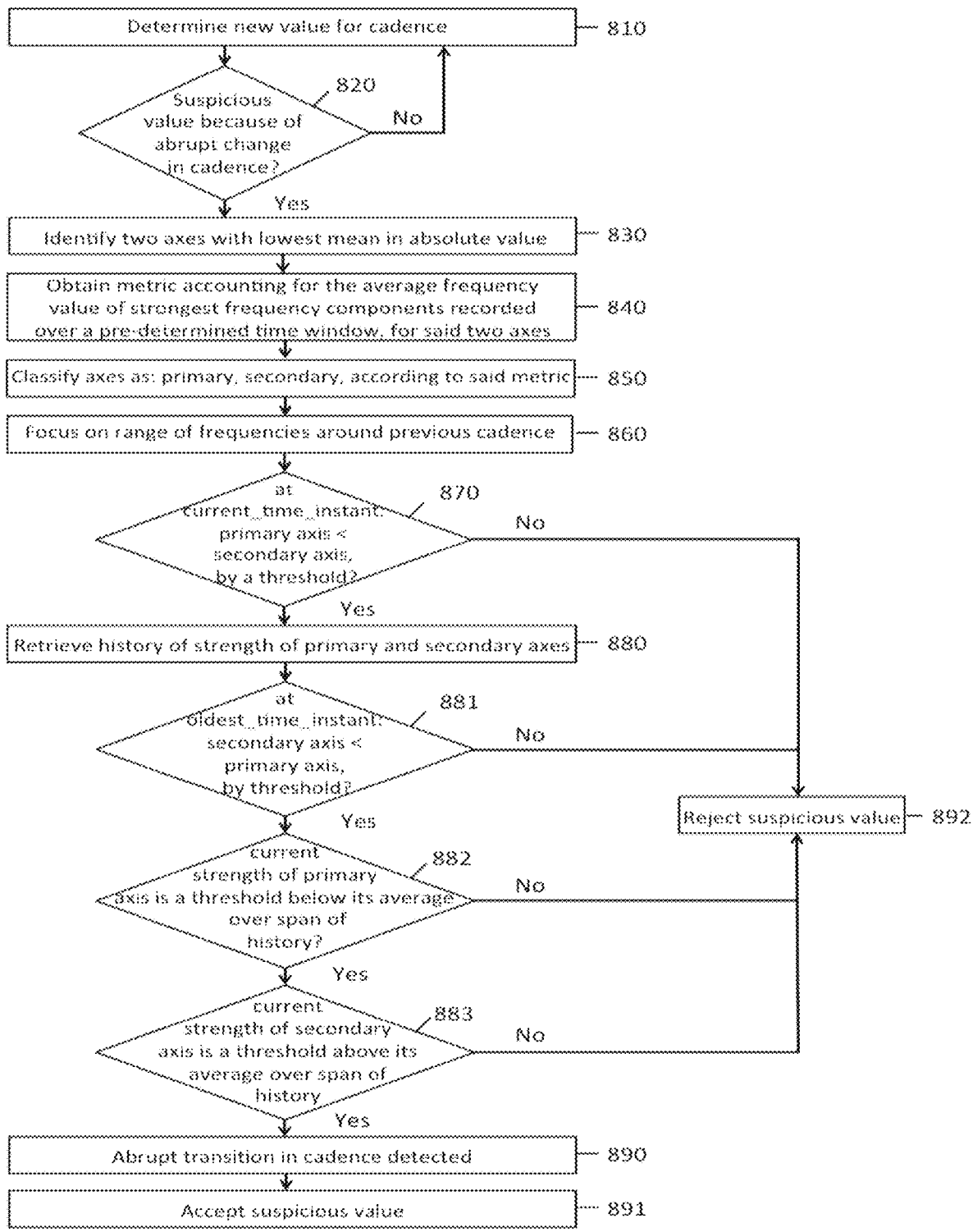
FIG. 8 illustrates a flow diagram for the process to detect an abrupt change in cadence according to one embodiment.

In some embodiments, a method for enhancing a user's dynamics and localization information may be used as shown in FIG. 7, which illustrates a flow diagram of possible basic steps. This Figure and its elements (710), (720), (730), (740), (750), and (760) are further described in application Ser. No. 14/922,174 and application Ser. No. 16/044,833.

Some embodiments may use all the available information to identify the position (and transitions between positions) of the mobile device within the user's body, as described in application Ser. No. 16/044,833.

Analogously, some embodiments may leverage any machine learning algorithm/methodology (e.g. support vector machine, decision tree, Naïve Bayes, or any other) to determine any gait attribute(s) (e.g. velocity and/or stride length and/or calories burned per time unit and/or activity and/or device position and/or other and/or any variations and/or combinations of any number of them), in a device process and/or application and/or in the context of controlling a user's representation, making use of the determined user's cadence (or fundamental frequency) as a feature for the determination of said gait attribute(s). For example, we can follow any of the procedures described within this application or any other to determine a gait attribute leveraging a machine learning algorithm and a training set of data to model said attribute, so that said model can be implemented in the device process and/or application and/or in the context of controlling a user's representation, and used to determine said gait attribute(s) by leveraging a set of features computed for said determination (in real time and with an update frequency larger than the user's step frequency or any other). In some embodiments, the features computed for said determination include the user's gait cadence; consequently, cadence will need to be also computed and recorded during the gathering of training data; in some embodiments, the features computed for said determination include the user's gait cadence and/or mean and/or variance and/or standard deviation and/or skew and/or kurtosis and/or principal frequency component and/or energy in selected frequency bands, and/or any other obtained from e.g. accelerometer data over a time window; in other embodiments, any variations and/or combinations thereof may also be possible. Some embodiments may use any of the procedures/strategies/methodologies described within this application and/or any other for the determination of the user's cadence to be used as a feature, including, by way of example without limitation: 1) analyzing a motion sensor signal using a combination of techniques comprising: wavelet transformation, Fourier transformation, and autocorrelation and/or 2) detecting abrupt changes in the user's cadence leveraging frequency and time information of the motion sensor signal.

FIG. 9A, 9B, 9C, 9D, 9E, 9F show scaled representations of images strip files used for animation. They have been scaled to fit in the document of this patent application, but their sizes can be chosen depending on a plurality of criteria, including by way of example without limitation, the available memory for the application using said images strips in the mobile or wearable device, the amount of heap memory expected to be used by the application in the mobile or wearable device, the screen size (e.g. physical size in terms of height millimeters*width millimeters or height pixels*width pixels) of the mobile or wearable device where said images strips are going to be used, the proportion of the device screen expected to be occupied by the animation, the density of the screen of the device (e.g. number of pixels per squared inch), the available storage capacity of the mobile or wearable device, any design and/or esthetic choices made by the developer of the application, and/or any other criteria and/or variations thereof and/or any combinations of any of the elements, criteria, and/or any other.

In a particular embodiment intended for an application in an Android device, FIG. 9A, 9B, 9C, 9D, 9E, 9F may represent images strip files with png extension (other file formats, e.g. jpg extension or others, may also be possible) stored in the "assets" folder of the mobile application, or in the "res/drawable-mdpi" folder of the mobile application, or in any other appropriate possible location chosen by the application developer. Criteria to choose folder in which to store the images strip files may include, by way of example without limitation: the expected density of the device screen (e.g. folder name with extension of: mdpi is usually assigned to resources for medium-density (mdpi) screens (~160 dpi), ldpi to resources for low-density (ldpi) screens (~120 dpi), hdpi to resources for high-density (hdpi) screens (~240 dpi), xhdpi to resources for extra-high-density (xhdpi) screens (~320 dpi), xxhdpi to resources for extra-extra-high-density (xxhdpi) screens (~480 dpi), xxxhdpi to resources for extra-extra-extra-high-density (xxxhdpi) uses (~640 dpi), etc.), the way the operating system of the device handles image files (bitmap files) in memory, the resources of the device (e.g. storage capabilities, memory, etc), and/or any other and/or any variations and/or combinations thereof. In one example of embodiment, FIG. 9A, 9B, 9C, 9D may be images strip files with png extension stored in the "assets" folder, with dimensions: 3146 pixels*145 pixels (again, sizes can be chosen depending on a plurality of criteria, as discussed above), with color space RGB (although in this patent application drawings have been grayscaled), containing 26 (in other embodiments, may contain 22, 16, or other numbers depending on criteria such as: type of activity being displayed, expected gait frequency of the activity, etc.) frames (sub-images) corresponding to a complete gait cycle (e.g. 26 frames span one complete gait (walking, jogging, running, or any other activity) cycle). In other words, these images strip files contain 26 frames (26 sub-images of 121 pixels*145 pixels each) arranged consecutively and timely ordered in such a way that displaying the frames consecutively in a device screen one after the other fast enough (e.g. frequency larger than 12 Hz) to make the human eye perceive them as continuous movement, we can achieve the effect of animation; this is a well-known technique used for example in cinemas, displaying consecutive frames fast enough (e.g. frequency of approximately 25 Hz), to achieve the illusion of animation to the human eye. By way of example without limitation, if the 26 frames are displayed on the device screen sequentially and continuously and cyclically repeated (frame 1, frame 2, frame 3, . . . , frame 25, frame 26, frame 1, frame 2, frame 3, . . . , frame 25, frame 26, frame 1, frame 2, . . . , and again and again), the device user will have the illusion that the person in the frames is walking continuously.

Figure 9A:
FIG. 9A, 9B, 9C, 9D, 9E, 9F show images strip files for a representation of a user with different gait attributes according to one embodiment.
Figure 9B:
Figure 9C:
Figure 9D:
Figure 9E:
Figure 9F:

FIG. 9E, 9F may represent images strip files with png extension, stored in the "assets" folder, with dimensions: 2662 pixels*145 pixels and 1936 pixels*145 pixels respectively (again, sizes can be chosen depending on a plurality of criteria, as discussed above), with color space RGB (although in this patent application drawings have been grayscaled), containing a number of frames of 22 and 16 respectively. In this example of embodiment, FIG. 9E, 9F represent complete cycles of running for a person, in contrast with FIG. 9A, 9B, 9C, 9D, which represent complete cycles of walking. It is worth noting that in this particular embodiment, FIG. 9E, 9F may have a number of frames (e.g. 22, 16) different from FIG. 9A, 9B, 9C, 9D (e.g. 26 frames), because FIG. 9E, 9F represent running cycles, while FIG. 9A, 9B, 9C, 9D represent walking cycles. In general, running cycles may be carried out faster than walking cycles, so the number of frames needed to cover a whole cycle (achieving good illusion of animation to the human eye) may be smaller for running than for walking. And even representing the same activity (e.g. running), an images strip file may have even smaller number of frames (e.g. 16 instead of 22) if the running activity represented in said strip is expected to be carried out at a faster frequency (e.g. FIG. 9F represents a running mode faster than the one represented in FIG. 9E, and consequently, it can use a smaller number of frames to complete the cycle, still achieving good illusion of animation to the human eye). On the other hand, some embodiments may use the same number of frames for all image strips regardless of the activity represented, following criteria including, by way of example without limitation, prevention of memory management problems (e.g. images strip files with different number of frames generally will have different sizes in terms of number of pixels (pixels height*pixels width), which will translate into allocations of blocks of memory of different sizes (typically the amount of memory allocated for an image file or a bitmap file may be equal to the number of pixels in height of the image, multiplied by the number of pixels in width of the image, multiplied by 4, if the amount of information bits used per pixel is 4); for instance, in the previous example, where the walking images strips have a size of 3146 pixels*145 pixels, the amount of memory allocated for each strip is: 3146*145*4~=1.8 MB; if the application is running low on memory, a procedure called garbage collection may be triggered to free unused blocks of memory; however, if we need to allocate a new image and the available memory is fragmented into small blocks of different sizes, none matching with the size required to allocate our new image, the application could face an "out of memory" error, which in some circumstances could be prevented if we use image files of the same size, and release or recycle an unused image file before trying to allocate a new image file). Different embodiments may have images strips with different numbers of frames (even if the strips represent the same type of activity). Other embodiments may use different approaches/ methodologies and/or any others and/or any variations and/ or combinations thereof.

In some embodiments, the user's representation shown in the images strip files (e.g. the person in FIG. 9A, 9B, 9C, 9D, 9E, 9F, 10A, . . . 10F) may take any other form(s), including, by way of example without limitation, any type of person, avatar, object, vehicle, robot, and/or any of the entities/forms mentioned in reference to element (110) in FIG. 1C, and/or any other elements in FIG. 1C and FIG. 2B, with any characteristics, and/or any other, and/or any variations and/ or combinations thereof.

Figure 10A:
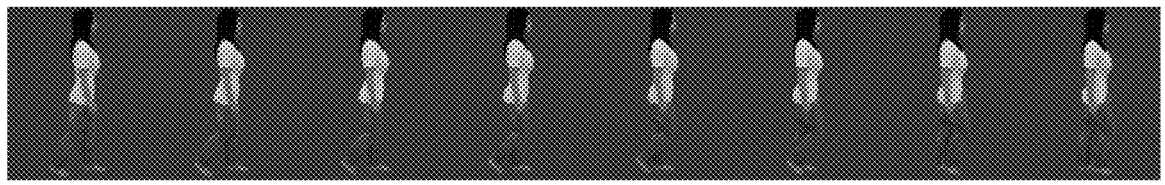
FIG. 10A, 10B, 10C, 10D, 10E, 10F show scaled portions of the previous images strip files for a representation of a user with different gait attributes according to one embodiment.
Figure 10B:
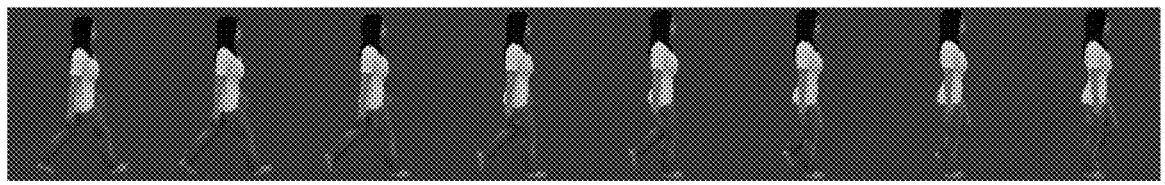
Figure 10C:
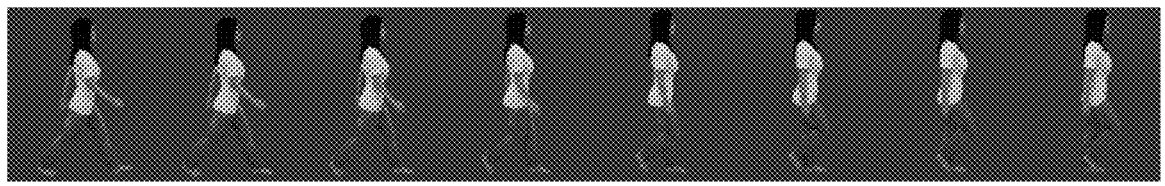
Figure 10D:
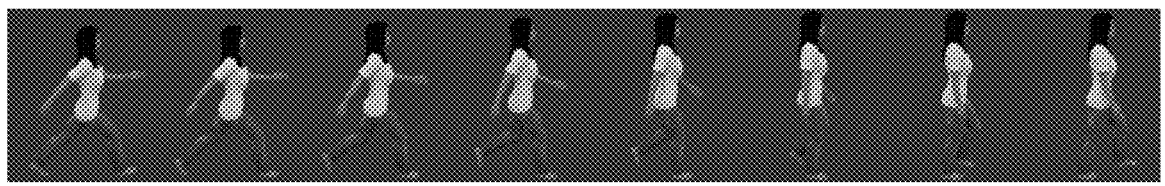
Figure 10E:
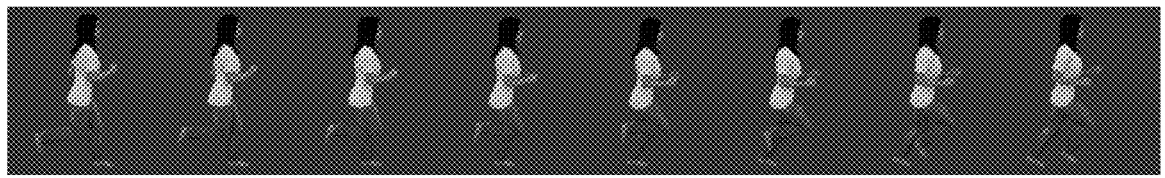
Figure 10F:
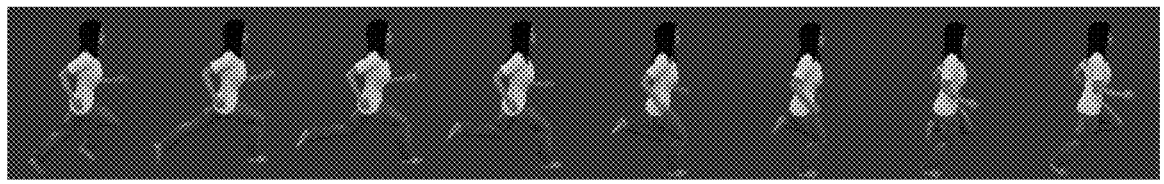

Since we want to show in real time changes in the user's representation being displayed on the device screen when the device user changes his/her gait (and/or gait attribute(s)), we can use different images strip files with different characteristics to show the differences brought by the change in the user's gait. By way of example without limitation, FIG. 9A, 9B, 9C, 9D represent walking cycles, but with different characteristic for the person being displayed on the screen; for instance, FIG. 9A displays a relatively short stride length for the person displayed, while FIG. 9B shows a bit larger stride length, FIG. 9C shows a larger stride length, and FIG. 9D shows a very large stride length; on the other hand, FIG. 9E, 9F represent running cycles, but also with different characteristic for the person being displayed on the screen; for instance, FIG. 9E displays a relatively short stride length for the person displayed as running, while FIG. 9F shows a larger stride length for the person displayed as running. These and other details can be observed more clearly in FIG. 10A, 10B, 10C, 10D, 10E, 10F, which represent scaled (zoomed in) portions of FIG. 9A, 9B, 9C, 9D, 9E, 9F respectively; in particular, we can see that the walking cycles represented in FIG. 10A, 10B, 10C, 10D, present different characteristics in the person being displayed; for instance, the stride length increases progressively from FIG. 10A to FIG. 10D, but there are also progressive changes in other details, such as, by way of example without limitation, the swing of the arms, the angles of the knees when taking new steps, the angles of the elbows, the back and forth movement of the head (achieved e.g. through appropriate rotations of the bone(s) controlling the head movement), the rotation of the hips, the rotation of the shoulders, the rotations of the feet, the change in elevation of the hips, the forward angle of the upper body, etc; these details and additional ones may be seen more clearly in FIG. 10E, 10F, which represent different running cycles, also showing differences in, by way of example without limitation, the way the fingers in the hands are grouped together in the form of a fist, the way the forearms shake, the way and angles in which the arms rotate, the angles of the thighs with the vertical direction, the angle at which the feet land on the ground with every step, the way the hair moves and bounces with every step, etc. In some embodiments, all the parts of the body shown in any of the figures FIG. 9, FIG. 10, may be controlled (e.g. their location, rotation, scale, surface texture, material, color, etc. may be chosen/modified/controlled by the designer rendering them appropriately, and/or by a programmer selecting their values/features programmatically, etc.) following any criteria.

In one example of embodiment, the effect of animation to the human eye can be achieved as described next. First, we are making the following assumptions for this particular example of embodiment: the mobile device the user is carrying is a smartphone; the operating system of the mobile device is Android; other embodiments may use different devices (e.g. smart glasses, smart watches, and/or any other type of mobile or wearable device, running in any type of operating system (by way of example without limitation, iOS by Apple, or any other)); the version of the operating system is Android 6.0.1. The mobile device has a touch screen of 4.5 inches (480 pixels*854 pixels), a 1.1 GHz Quad Core chipset, 1 GB RAM+8 GB ROM, supports microSDXC card up to 32 GB, and has the typical wireless and other type of functionalities of an average smartphone. An application is developed for said example of smartphone (again, other embodiments may use any other type of device, characteristics, elements, and/or any other and/or any variations and/or combinations thereof) using any of the available software and/or hardware and/or any other type tools (e.g. a MacBook Pro with OS X El Capitan, processor of 2.4 GHz, memory of 8 GB, equipped with integrated development environment such as Eclipse or Android Studio, together with any available plugins, tools (e.g. Android Development tools, Android SDK tools, or any other), and/or any other elements if needed). One possible example of embodiment for the developed Android application can be described with the help of the Java-style pseudocode in FIG. 11A, 11B, which will be used to discuss details of how the animation (or control of the user's representation) can be achieved on a mobile device screen in one embodiment. Different embodiments may use different approaches, and even the same approach can be tackled in different ways using a variety of alternative software and/or hardware resources; any modifications and/or combinations of any elements and/or procedures and/or any other type of entity may also be possible in some embodiments. As shown in FIG. 11A, a class extending the SurfaceView class and implementing the SurfaceHolder.Callback interface may be created, named AnimationView; one of the purposes of the SurfaceView class is to provide a surface in which a secondary thread can render into the screen; when used in this way, we should to be aware of some threading semantics: 1) All SurfaceView and SurfaceHolder.Callback methods will be called from the thread running the SurfaceView's window (typically the main thread of the application). They thus need to correctly synchronize with any state that is also touched by the drawing thread. 2) It is important to ensure that the drawing thread only touches the underlying Surface while it is valid—between SurfaceHolder.Callback.surfaceCreated( ) and SurfaceHolder.Callback.surfaceDestroyed( ). The SurfaceHolder.Callback interface may be implemented to receive information about changes to the surface.

Within the AnimationView class, a class named AnimationThread may be created extending the Thread class and implementing the interfaces SensorEventListener (used for receiving notifications from the SensorManager when sensor values have changed), and OnTouchListener (for a callback to be invoked when a touch event is dispatched to the view. The callback will be invoked before the touch event is given to the view). A Thread is a concurrent unit of execution. It has its own call stack for methods being invoked, their arguments and local variables. Each application has at least one thread running when it is started, the main thread, in the main ThreadGroup. The runtime keeps its own threads in the system thread group. There are two ways to execute code in a new thread. You can either subclass Thread and overriding its run( ) method, or construct a new Thread and pass a Runnable to the constructor. In either case, the start( ) method must be called to actually execute the new Thread. Each Thread has an integer priority that affect how the thread is scheduled by the OS. A new thread inherits the priority of its parent. A thread's priority can be set using the setPriority(int) method.

Focusing on FIG. 11A, the 12 lines following the first 2 lines, are used to declare some variables needed for the management and drawing of the images. For instance, imagesStrip is defined as a Bitmap to hold the information (in memory) of the image strip file we want to work with; frame_0_StartTime is defined as a long variable to hold the time (in milliseconds) at which the 0th (in other words, first) frame was started to be displayed on the screen, thus serving as an origin reference point in time; beginning_manageCurrentFrame is defined as a boolean variable (initially set to true) to indicate whether we are entering the manageCurrentFrame method for the first time; once said method is entered (and if currentFrame is equal to zero), beginning_manageCurrentFrame will be set to false; timeIntoCompleteAnimation is defined as a long variable to hold the time (in milliseconds) elapsed since an origin reference point in time, thus allowing us to know how deep into a complete animation cycle we are in terms of time; frameCount is defined as an integer variable (set to 26 in this particular example, but any other values are also possible, and it could even be changed programmatically in the application), and its purpose is to account for the number of frames (sub-images) in the images strip file(s) (e.g. with extension png) we are working with; in some embodiments, it may be advisable to keep frameCount constant across different images strip files to prevent memory segmentation that could lead to "out of memory" errors under some circumstances (e.g. low memory conditions); completeAnimationPeriod is defined as an integer variable, and its purpose is to hold the amount of milliseconds a complete animation period should last (initially set as 1000 in this particular example, for instance, assuming 2 Hz cadence, the complete animation (2 steps) period=1 second=1000 milliseconds; nevertheless this value should be programmatically changed based on the determined cadence or fundamental frequency of the user; for instance, if the determined cadence is 1 Hz, the complete animation (2 steps) period=2 seconds=2000 milliseconds); currentFrame is defined as an integer (initially set to zero), and its purpose is to account for the order of the frame (e.g. from 0 to 25 if we work with 26 frames, and cyclically repeating (e.g. . . . , 24, 25, 0, 1, . . . )) within the images strip file we are working with, that is to be displayed on the screen for the purpose of achieving animation to the human eye; frameWidth and frameHeight are defined as integers (initialized to 300 and 360 in this particular example, but other values are also possible), and their purpose is to set the actual dimensions of the frame when displaying it on the device screen, in terms of the actual number of pixels the frame will occupy on the screen of the device.

It is worth noting that these values can be modified in any way for other embodiments depending on a plurality of criteria, including by way of example without limitation, the physical size of the screen of the device, the density of pixels of the screen, the amount of heap memory an application is allocated in the device, the amount of heap memory an application is expected to allocate for bitmaps, design criteria of the developer, and/or any variations and/or combinations thereof; it is also worth noting that these numbers do not need to match the actual physical dimensions of the frames in the images strip file (e.g. png extension), because Android OS allows scaling (increase or reduction) of the bitmaps in memory, before displaying them on the screen of the device; frameToDraw is defined as a Rect variable (rectangle), specifying the rectangular region to be selected from the scaled bitmap (to be obtained from the images strip file), to be displayed on screen; said rectangular region is delimited by means of the (x,y) coordinates of its top-left point (in this example, (0,0)) and the (x,y) coordinates of its bottom-right point (in this example, (frameWidth,frameHeight)); in this particular example of initialization, Rect(0, 0,frameWidth,frameHeight), we are delimiting the rectangular region covered by the first frame within the scaled bitmap obtained from the images strip file to be drawn on the device screen; personXPos and personYPos are defined as float variables, and their purpose is to account for the x and y coordinates (in pixels) of the top-left point of the rectangular region in the device screen where the frame to be displayed will be placed; whereToDraw is defined as a RectF variable (rectangle delimited by float coordinates), and its purpose is to specify the rectangular region to be selected from the device screen to draw the frame we are dealing with; said rectangular region is delimited by means of the (x,y) coordinates of its top-left point (in this example, (personXPos, personYPos)) and the (x,y) coordinates of its bottom-right point (in this example, (personXPos+frameWidth, personYPos+frameHeight)); in this particular example of initialization, RectF(personXPos,personYPos, personXPos+frameWidth,personYPos+frameHeight), we are delimiting a rectangular region of dimensions equal to the frame to be displayed, where the top-left point is defined by (personXPos, personYPos), in this case (0,0), thus coinciding with the upper left corner of the device screen.

It is worth noting that although (personXPos, personYPos) coordinates are not changed in the pseudocode presented in FIG. 11A, 11B, some embodiments may change these values programmatically, thus making the frame displayed on the device screen change its position within the device screen (in other words, the rectangular region defined to hold the frame in the device screen is translated across the screen, since its defining coordinates have been changed by changing (personXPos, personYPos)); the effect of these changes would be the illusion of the person displayed in the frames moving across the screen of the device; this is different from moving (walking, running, etc.) in place, that is, moving in a fixed position in the device screen, as if the person was moving (walking/running, etc.) over a treadmill; some embodiments may choose to translate across the screen some other image bitmap displayed as a background over which the person in our frames is drawn, thus achieving the illusion that the person in our frames is moving across the background image bitmap, even if the person in our frames is moving (walking/running/etc.) in a rectangular region fixed in the device screen; in other words, the background image bitmap is translated across the device screen while the person in our frames moves in place (in a fixed position), thus giving the illusion that the person in our frames is translating across the scene displayed in the background image bitmap; other embodiments may use any variations and/or combinations of any said elements/changes/strategies and/or any other, including, by way of example without limitation, the translation and/or rotation and/or scaling of the person's image bitmap and/or the background's image bitmap and/or any other image bitmap to achieve any of the effects and/or illusion of animation of any kind (including navigation through virtual environments) and/or any other. Other embodiments may use any other variations and/or combinations of any of said elements/devices/specifications/characteristics/tools/variables/initializations/methods/approaches/techniques and/or any other tools/library/API, or any other in any fashion and for any purpose, including by way of example without limitation, achieving similar or different and/or variations and/or combinations of any effects described above.

Continuing with FIG. 11A, the method manageCurrentFrame( ) may be used to select the appropriate frame in the scaled bitmap of the images strip in order to achieve the illusion of animation (or control of the user's representation, or control of an attribute (e.g. cadence, stride length, velocity, activity, calories burned per time unit, etc.) of the user's representation) to the human eye; in simple words, the illusion of animation can be achieved by quickly displaying ordered and consecutive frames showing static postures of the user's representation; if the frames are displayed fast enough (e.g. frames updated with a frequency larger than approximately 12 Hz), they will look as a continuous and smooth transition to the human eye, achieving the effect of animation; in this example of embodiment, we first obtain the current time in milliseconds, and store it in a variable called time; next, if this is the first time accessing this method and we are starting the application (circumstance characterized by beginning_manageCurrentFrame being true, and currentFrame being 0), then we set the origin of time reference (frame_0_StartTime) equal to the previously obtained time, and we set beginning_manageCurrentFrame as false to avoid further changes; next, we obtain timeIntoCompleteAnimation as the difference between the previously determined time and frame_0_StartTime; next, we determine currentFrame as the integer value of (timeIntoCompleteAnimation*frameCount/completeAnimationPeriod) being applied the modulus operand (%) with frameCount (in order to obtain the rest of the division between (timeIntoCompleteAnimation*frameCount/complete AnimationPeriod) and frameCount); next, frameToDraw.left=currentFrame*frameWidth and frameToDraw.right= frameToDraw.left+frameWidth update the rectangular region borders within the scaled images strip to be drawn; in particular, the left border of said rectangular region is defined multiplying the currentFrame number by the frameWidth, while the right border of said rectangular region is defined as its left border plus frameWidth, the frame width; other embodiments may use any other approaches, and/or software, and/or libraries, and/or APIs, and/or variables, and/or methodologies, and/or any other and/or variations and/or combinations thereof to achieve the same or similar effects.

Continuing with FIG. 11B, the method doDraw(Canvas canvas) is mainly used to draw (render) on the device screen; first, the method manageCurrentFrame( ) is called to select the frame (rectangular region) within the scaled images strip to be drawn; next, canvas.drawBitmap performs the drawing or rendering on the device screen (canvas) of the specified rectangular region (frameToDraw) of the scaled images strip bitmap (imagesStrip), scaling/translating automatically to fill the destination rectangle (whereToDraw); it is worth noting that within this doDraw method, additional calls to canvas.drawBitmap can be performed to draw different images (e.g. background images, or images of other elements to be drawn within the device screen, etc. defined in analogous ways to how the imagesStrip bitmap is defined), which can be rendered in different positions (again, modifying the borders or coordinates of delimiting points of their defining rectangular (or other shape) regions), (and/or rendered with different rotations and/or scaling factors) within the device screen, as desired, thus achieving the effect or illusion of different types of movement across the device screen; it is also worth noting that some embodiments may leverage additional software methods implemented by the developer or provided by the device operating system to achieve any of the effects or any other in any fashion, including any variations and/or combinations thereof; by way of example without limitation, some embodiments may leverage Android operating system methods to perform rotations, scaling, translations or any other and/or variations and/or combinations thereof to achieve any effect in any fashion, for instance to achieve an illusion of movement/ displacement of a person (e.g. a representation of the device's user) within a virtual environment displayed on the device screen; it is also worth noting that the doDraw method may be triggered (e.g. called within the main Thread) fast enough to achieve illusion of animation to the human eye (typically every 16 milliseconds, or a frequency of 60 Hz, although other frequencies may also be possible); some embodiments may use any variations and/or combinations of any terms/elements/procedures or any other in any fashion.

Continuing with FIG. 11B, the method setAnimationImagesStrip(int stripResource) is mainly used to select the images strip file (e.g. extension png) from which its frames are to be drawn on the device screen; the input parameter of this method, stripResource, is an integer to identify the images strip file we want to work with; for sake of simplicity, in this particular example of embodiment, we are assuming 3 images strip files ("firstImagesStripFile.png", "secondImagesStripFile.png", "thirdImagesStripFile.png") stored in the assets folder of the application, and stripResource will take values of 0, 1, and 2 to identify the first, second and third images strip files respectively; in this particular example, we may assume that said images strip files may correspond to FIG. 9A, FIG. 9B, and FIG. 9C respectively. Other embodiments may have a smaller or larger number of images strip files following any criteria including memory management, storage capabilities, design strategies, granularity in the changes of attributes of the representation, and/or any other including any variations and/or combinations thereof; by way of example without limitation, some embodiments may use 6 images strip files, corresponding to FIG. 9A, FIG. 9B, FIG. 9C, FIG. 9D, FIG. 9E, and FIG. 9F or any variation of them; in one embodiment, FIG. 9E and FIG. 9F may have the same number of frames (e.g. 26) as FIG. 9A, FIG. 9B, FIG. 9C, and FIG. 9D for efficient memory management purposes (e.g. to avoid heap memory fragmentation); other embodiments may use a very large number of images strip files, each one of them with the person (or user's representation) whose gait cycle is being displayed presenting, by way of example without limitation, a different value for a gait (or any other type) attribute (or one or more attributes) we may be focusing on; for instance, we could have 21 (or any other number) images strip files of 26 frames each, and each images strip file would present the person performing the gait activity (walk/run/jog or any other type of activity) with a different value (or any characterizer) of attribute(s).

Focusing by way of example without limitation on stride length, it may range for example from 15 inches to 45 inches (these values in inches may correspond to an exemplary user, and to a natural scale representation of a user, but it is obvious that the images strip files show scaled representations of a user, and consequently the stride length values of the person being shown in these images strip files are scaled values of the previously referred ones (e.g. 15 inches to 45 inches could accordingly be scaled down to 15 millimeters to 45 millimeters, or any other values following any criteria including by way of example without limitation, design)), with the first images strip file showing a stride length accordingly scaled to represent a real user's stride length of 15 inches, the second images strip file presenting a stride length accordingly scaled to represent a real user's stride length of 16.5 inches, the third images strip file illustrating a stride length accordingly scaled to represent a real user's stride length of 18 inches, and so on; consequently, we can control (e.g. by selecting the appropriate images strip file (with the appropriate value of attribute) to be rendered on the screen) in real time the stride length of the representation of the device user being displayed on the device screen, and we can replicate the values of stride length of the user with the values of stride length of the representation (obviously accordingly scaled to fit within the device screen), with a granularity (in this example, 1.5 inches) equal to the range in the values of stride length (in this example, 30 inches=45 inches–15 inches) divided by the number of images strip files we have minus 1 (in this example, 20=21-1). By way of example without limitation, the user's representation's stride length (or one or more attributes) may be controlled by setting its value proportional to the value of the user's determined stride length. Analogously, an aspect of an application or process in the device may be controlled by setting its value proportional to the value of the user's determined stride length (e.g. the value of brightness of the screen (and/or any aspect of user interface, settings, etc.) may be set proportionally to the value of the determined stride length), or by triggering/stopping/controlling in any way any procedure/process/application depending on the value of the determined stride length (e.g. if stride length is equal to 20 inches, then trigger (e.g. software activation) an out-loud reader), or in any other way. In some embodiments, the control over the stride length of the representation of the user can be performed with an update frequency larger than the user's step frequency, e.g. performing the selection of the appropriate images strip file (with the appropriate value of attribute (e.g. stride length)) to be rendered on the screen, with an update frequency larger the the user's step frequency; some embodiments may achieve this, for example, by calling the setAnimationImagesStrip method with the desired frequency and/or as soon as a new images strip file is needed; for this, some embodiments may call the setAnimationImagesStrip method from within the manageCurrentFrame method (e.g. called from within the doDraw method, which may be typically triggered with a frequency of 60 Hz); other embodiments may choose to call the setAnimationImagesStrip method from outside the manageCurrentFrame method, but within the onSensorChanged method (e.g. may be triggered with a frequency equal to the accelerometer sampling rate, which may be larger than the user's step frequency); other options are also possible; additional details are provided throughout the rest of this application.

It is also interesting to note that the setAnimationImagesStrip method presented in FIG. 11B may be modified in some embodiments: for example, the application may create and hold in memory the Bitmaps for each one of the images strip files stored in the assets folder (keeping for example several Bitmap variables, named e.g. imagesStrip1, imagesStrip2, imagesStrip3, etc.) and work directly with these Bitmaps rather than working with a single Bitmap and recycling it and assigning it the information of a new images strip file every time a new images strip file is needed; other embodiments may use any other strategies and/or any variations and/or combinations thereof.

It is worth noting that stripResource (e.g. in FIG. 11B) can be easily set programmatically, by way of example without limitation, using "if else" structures leveraging the value of, for example, the determined stride length (e.g. if the determined stride length is equal to (or less than) 15 inches, then stripResource is equal to 0; else, if the determined stride length is equal to (or less than) 16.5 inches, then stripResource is equal to 1; else, if the determined stride length is equal to (or less than) 18 inches, then stripResource is equal to 2; and so on); other embodiments may use alternative approaches, and leverage additional variables to programmatically set the value of stripResource; by way of example without limitation, some embodiments which determine in real time the device user's gait cadence (or frequency), together with the device user's gait velocity, together with the device user's gait activity, may programmatically set (with update frequency which can be chosen to be as the frequency of determination of cadence, velocity and activity, e.g., it may be larger than the user's step frequency) the value of stripResource using "if else" structures, leveraging as variables: the current value of stripResource (to be changed to a new value of stripResource), the newly determined user's gait cadence (or frequency), the newly determined user's gait velocity, the previously determined user's gait activity (associated to the current value of stripResource, which can be different from the new to be determined value of stripResource), and the newly determined user's gait activity. By way of example without limitation, if stripResource is equal to 0 (associated to e.g. activity "walking"), then, if the newly determined activity is "walking", and the newly determined velocity and the newly determined cadence (or frequency) have values that establish a newly determined stride length of 16.5 inches (e.g. velocity divided by cadence (after appropriate unit conversions, if needed), is equal to 16.5 inches), then stripResource is set equal to 1, and the value of activity is set to "walking". Or, if stripResource is equal to 10 (associated to e.g. activity "walking"), then, if the newly determined activity is "running", and the newly determined velocity and the newly determined cadence (or frequency) have values that establish a newly determined stride length of 45 inches (e.g. velocity divided by cadence (after appropriate unit conversions, if needed), is equal to 45 inches), then stripResource is set equal to 20, and the value of activity is set to "running". It is worth noting that some embodiments may use ranges or intervals for the decisions, and/or adjust the granularity of the decisions, and/or set assumptions or additional conditions that need to be satisfied in order to allow a change in stripResource; for example, some embodiments may choose to keep the same value of stripResource for some predefined ranges in the values of velocity and cadence (and thus some ranges in the value of stride length) given a previously determined activity (e.g. to prevent hysteresis cycles), or even prevent changes for some threshold of time if the newly determined values involve some drastic change (e.g. sudden change from "running" with stride length of 45 inches to "walking" with stride length of 15 inches).

It is also worth noting that, following any criteria referenced above, or any other, some embodiments may call the setAnimationImagesStrip method within the manageCurrentFrame method (which is called within the doDraw method), achieving an update frequency of the images strip file being displayed equal to the screen refresh rate (typically 60 Hz); some embodiments may also use alternative strategies (e.g. use of timers to delay operations, or use of conditionals to call setAnimationImagesStrip only after doDraw has been called for a number of times, or call setAnimationImagesStrip outside manageCurrentFrame (but within onSensorChanged method, which is triggered every time the sensor (e.g. accelerometer) delivers a new measurement, thus achieving an update frequency for setAnimationImagesStrip equal to the accelerometer sampling frequency) or any other strategies and/or variations and/or combinations thereof), in order to change or set the update frequency with which the setAnimationImagesStrip method is called; consequently, some embodiments may choose to set an update frequency for setAnimationImagesStrip higher (or lower) than the user's step frequency, thus controlling the stride length (e.g. some embodiments may use images strip files with a different stride length each, so every time we call setAnimationImagesStrip with a new value of stripResource, the user's representation displayed on the device screen is changing its stride length, and we may control this process leveraging the determined user's stride length (e.g. user's velocity divided by user's cadence)) of the representation of the user being displayed on the device screen with an update frequency higher (or lower) than the user's step frequency. It is also worth noting that in some embodiments, the referred controlling may apply to any other attribute (including by way of example without limitation, any angles (with respect to any direction (e.g. vertical, horizontal, etc.)) or any colors or any texture or any kind of displacements due to movement or any other characteristic of any part of the body (e.g. knees, arms, trunk, hips, shoulders, feet, neck, head, hands, fingers, etc.), or any characteristic of the gait (e.g. velocity, cadence, stride length, calories burned per time unit, activity, or any other)) or any other attributes (including by way of example without limitation, any number of them, e.g. any from 0 to a plurality) of the representation of the user on the device screen; analogously to the way the controlling of the stride length of the representation of the user can be achieved in some embodiments with an update frequency larger (or lower in other embodiments) than the user's step frequency, simply by selecting the appropriate frame of the appropriate images strip file with the appropriate stride length to be displayed on the device screen with the appropriate update frequency, other embodiments may perform the controlling of any other (or others, including e.g. any number of) attribute(s) (including without limitation, any of those mentioned above) of the representation of the user with an update frequency larger (or lower in other embodiments) than the user's step frequency, simply by selecting the appropriate frame of the appropriate images strip file with the appropriate attribute (or attributes) to be displayed on the device screen with the appropriate update frequency. Other embodiments may use any variations and/or any other approaches/methodologies/variables and/or any additional ones and/or combinations thereof.

It is also worth noting that a single one of the user's determined attributes (e.g. stride length), may control one or more attributes of the user's representation being displayed on the device screen; for example, as described above, the user's determined stride length may control the stride length of the user's representation being displayed on the device screen; this may be achieved in some embodiments by controlling, leveraging the value of determined user's stride length, the selection of an appropriate images strip file where the user's representation has the appropriate value of stride length (e.g. in pseudocode: if (determined_stride_length==value1) {then, images_strip_file="file1.png";} else if (determined_stride_length==value2) {then, images_strip_file="file2.png";} . . . and so on); in some embodiments, said user's representation may change other attributes besides stride length if we compare it with different images strip files; in other words, when we select the appropriate images strip file with the new value of stride length, other attributes in the user's representation may have also changed besides the stride length; for example, looking at FIG. 9A, 9B, 9C, 9D, (or FIG. 10A, 10B, 10C, 10D for more details) we see progressive enlargements in the stride length of the user's representation, but at the same time we also see changes in, by way of example without limitation: the swing of the arms, the vertical displacement of the hips (and the whole upper body), the rotations of the hips on the horizontal plane, the rotations of the shoulders on the horizontal plane, the rotations of the neck (and head) on the forward-backward direction, the angles of the thighs with the vertical direction, etc. Further details may also be appreciated in FIG. 10E, 10F, where, by way of example, the hair of the user's representation is changed (e.g. it bounces with every step), or the angle of the feet at landing on the ground is also changed. Other embodiments may choose to modify or control these and/or any other attributes in any way. Consequently, the determined stride length of the user may control the stride length of the user's representation being displayed on the device screen, and it may also control additional attributes of said representation (even if it is because of indirect reasons); as described in the rest of this application, said control may be performed in real time and with an update frequency larger than the user's step frequency, because for example in some embodiments said control is based on the same principles ruling the control of the user's representation's stride length with the user's stride length.

The same reasoning may be extended to any other attribute of the user, since in some embodiments, a user's determined gait attribute (e.g. cadence, activity, velocity, calories burned per time unit, etc.) may control one or more attributes of the user's representation being displayed on the device screen. By way of example without limitation, the user's representation's cadence (or one or more attributes) may be controlled by setting its value proportional to the value of the user's determined cadence. Analogously, an aspect of an application or process in the device may be controlled by setting its value proportional to the value of the user's determined cadence (e.g. the value of brightness of the screen (and/or any aspect of user interface, settings, etc.) may be set proportionally to the value of the determined cadence), or by triggering/stopping/controlling in any way any procedure/process/application depending on the value of the determined cadence (e.g. if cadence is equal to 2 Hz, then trigger (e.g. software activation) an out-loud reader), or in any other way. For example, as shown in FIG. 13 and FIG. 11A, the user's determined cadence may control the user's representation's cadence in real time and with an update frequency larger than the user's step frequency: the variable completeAnimationPeriod is controlled by the determined (in real time and with an update frequency larger than the user's step frequency) user's cadence, and it controls the value of the variable currentFrame, which is responsible for how fast a whole gait cycle of the user's representation is displayed, or how long it will take to display a whole user's representation's gait cycle (e.g. doDraw method in FIG. 11B is called with regular frequency of, for instance, 60 Hz, and this method calls the manageCurrentFrame method (FIG. 11A) to control which frame to be rendered on the device screen (currentFrame); as shown in FIG. 11A, if completeAnimationPeriod is large, it will take long time for the value of currentFrame to change, while if completeAnimationPeriod is short, it will take short time for the value of currentFrame to change; thus we are controlling the time it takes for currentFrame to change, or the time it takes for frames to change, or the time it takes for 26 frames to be changed, or the time it takes for a whole gait cycle to complete, or the time period of the gait, or the cadence or frequency (=1/period) of the gait of the user's representation on the device screen). At the same time that the user's determined cadence controls the user's representation's cadence, in the same conditions it may also control other attributes in the user's representation; for example, some embodiments may leverage the variable completeAnimationPeriod (controlled by the determined user's cadence) to control the selection of the images strip file whose frames are to be displayed on the screen; this can be easily achieved e.g. by using the variable completeAnimationPeriod within the setAnimationImagesStrip method in FIG. 11B, and including completeAnimationPeriod within the conditionals used to select the images strip file; for example: if (stripResource==0 && completeAnimationPeriod<1000) {myFilename="firstImagesStripFile_shortPeriod.png";} else if (stripResource==0 && completeAnimationPeriod>1000) {myFilename="firstImagesStripFile_longPeriod.png";} . . . and so on; other embodiments may use more complex conditionals and/or structures and/or any other methodologies/approaches/strategies and/or variations and/or combinations thereof. Consequently, the variable completeAnimationPeriod may control the images strip file to be displayed on the device screen in real time and with an update frequency larger than the user's step frequency; since we can modify/control one or more attributes of the user's representation in the images strip files (e.g. translations, scaling factors and rotation angles with respect to the vertical (and/or horizontal and/or forward-backward and/or any other) direction of thighs, shins, feet, hips, spine, chest, neck, head, shoulders, upper arms, forearms, hands, fingers, etc. and/or color, texture, material, etc. of any of the parts of the body or surfaces composing the user's representation, etc.), we can control one or more attributes of the user's representation in real time and with an update frequency larger than the user's step frequency, leveraging the determined user's cadence.

Analogous reasoning may be extended to any of the other determined user's gait parameters. By way of example without limitation, the determined user's activity, velocity, calories burned per time unit, and device position, may be leveraged analogously to the way the variable completeAnimationPeriod may be used to control one or more attributes of the user's representation in real time and with an update frequency larger than the user's step frequency, as described in application Ser. No. 16/044,833.

Continuing with FIG. 11B, within the setAnimationImagesStrip method, the first line: imagesStrip.recycle( ) is intended to free the memory resources being assigned to the currently used images strip file, because in this example of embodiment we want to assign those memory resources to hold a new different images strip file; it is worth noting that other embodiments may not need this step, but instead use additional memory allocations to handle different images strip files; this decision may depend on the available heap memory for the application, the size of the images strip files being handled, or any other criteria; other embodiments may employ any variations and/or any combinations and/or any other strategies, procedures, elements and/or any other. The next line: imagesStrip=null reiterates the previous line memory management aspect, trying to make sure that the memory allocated for the images strip file has been released; again, this step can be avoided in some embodiments following the plurality of criteria; it is also worth noting that in some embodiments working with early versions of Android operating system, in order to quickly free memory resources, the application developer might call the garbage collection procedure directly (System.gc( );); other embodiments may use any other procedures, variations and/or combinations thereof for efficient memory management. The next line: AssetManager assets=getResources( ).getAssets( ) is intended to declare the assets in the Android application in order to have easy access programmatically to the images strip files stored in the assets folder; it is worth noting that other embodiments may not store said files in the assets folder, so alternatives methods and/or procedures may be used; the next line: InputStream buffer is intended to declare an InputStream type variable, called buffer, destined to hold information from the images strip file we work with; again, some embodiments may use alternative methods and/or procedures and/or any other to read information from images strip files, so this and some of the next lines in this method may be substituted by different alternatives in some embodiments; the next line: String myFilename=" " declares a String type variable called myFilename, initialized empty, whose purpose is to hold the name of the images strip file we work with; in this particular example of embodiment we have 3 images strip files stored in the assets folder, whose names are: "firstImagesStripFile.png", "secondImagesStripFile.png", and "thirdImagesStripFile.png". The next 6 lines within the setAnimationImagesStrip method are "if else" structures intended to assign the appropriate images strip file name to the myFilename variable depending on the value of the stripResource variable; next, we create a try and catch block in order to safely (e.g. in terms of properly handling possible exceptions) perform the tasks stated within the try block: buffer=new BufferedInputStream(assets.open(myFilename)), which is intended to programmatically open the selected file from the assets folder and assign the information to the buffer variable, and imagesStrip= BitmapFactory.decodeStream(buffer), which is intended to decode the information held by the buffer variable and covert it into a Bitmap type variable, in this case, imagesStrip. The next line: imagesStrip=Bitmap.createScaledBitmap(imagesStrip, frameWidth*frameCount,frameHeight,true) is intended to process the information held by the imagesStrip variable, in order to create a scaled version of that Bitmap, where the new dimensions of the scaled Bitmap are specified by frameWidth*frameCount, and frameHeight, since the Bitmap will hold the information of the images strip file scaled to have a width equal to frameWidth multiplied by frameCount, and to have a height equal to frameHeight.

It is also worth noting that some embodiments may leverage the onSensorChanged method provided by the SensorEventListener interface (used for receiving notifications from the SensorManager when sensor values have changed); FIG. 13 shows schematic squeleton pseudocode for the onSensorChanged method for an example of embodiment, which would include this method within the AnimationThread class of FIG. 11A; multiple additions and/or variations and/or alternatives and/or combinations thereof are also possible in some embodiments. The "public void onSensorChanged(SensorEvent event)" method is called when sensor values have changed; detailed information on this and other topics can be found online at the android developer website or any other online sources (e.g. developer.android.com developer.android.com); basically, to summarize in simple words, every time the accelerometer, if(event.sensor.getType( )===Sensor.TYPE_ACCELEROMETER), has new measurements, the onSensorChanged method is triggered and the new acceleration values can be read (e.g. double x_acceleration=event.values[0]; double y_acceleration=event.values[1]; double z_acceleration=event.values[2]); some embodiments may use the read acceleration values as inputs for a method that may determine the device user's gait velocity, calories burned per time unit, cadence, and activity (and/or any other gait (or any other type) attribute, such as stride length, and/or any other, and/or any variations and/or combinations thereof, including any number of them (e.g.: velocity, cadence, and activity; or velocity, cadence, activity, and stride length; etc.)) following any of the procedures/methodologies described in this specification or any other and/or any variations and/or combinations thereof; for example, the method determine_gait_parameters(double x_acceleration, double y_acceleration, double z_acceleration, double z_acceleration, double signal_vector_module_acceleration), may return an array of doubles containing the determined gait parameters: e.g. double[ ] gait_parameters=determine_gait_parameters (x_acceleration, y_acceleration, z_acceleration, signal_vector_module_ acceleration); by way of example, the method determine_gait_parameters may be called directly from within the onSensorChanged method, thus determining the gait parameters with a frequency equal to the accelerometer sampling rate, which may be larger than the user's step frequency.

Some embodiments may determine (e.g. using the determine_gait_parameters method) only one of the device user's gait attributes (e.g. only velocity, or only cadence, or only activity, or only stride length, or only calories burned per time unit, or any other possibilities), while other embodiments may determine one or more (or any number) of the device user's gait (or any other type) attributes; again, it is worth noting that some embodiments may determine said attributes in real time simultaneously (or nearly simultaneously, e.g. one after the other, but with very small time differences, since some embodiments may determine them all with very high update frequencies (e.g. 60 Hz or higher)); other embodiments may use different approaches and/or variations and/or combinations thereof; for example, some embodiments may hold the read acceleration values in arrays that can be passed as inputs to the determine_gait_parameters method at desired time intervals, thus achieving a desired update frequency for the determination of the gait parameters; other embodiments may use upsampling/downsampling/filtering/or any other techniques to help in the setting of a desired update frequency for the determination of gait parameters; other embodiments may perform storing of acceleration values (e.g. creating a time window of acceleration values) within the determine_gait_parameters method and only trigger the actual determination of parameters when a desired amount of acceleration values (or a desired time interval in a time window has been reached; other embodiments may use different approaches and/or variations and/or combinations thereof. Some embodiments may use the determine_gait_parameters method to determine any gait parameters or any others leveraging any possible methodology, including by way of example without limitation, the stride length (e.g. stride length equals the gait velocity divided by the gait cadence (or frequency)), the calories burned by the device user (for instance, the relationship between velocity and calories burned has been extensively studied (e.g. "Medicine and Science in Sports and Exercise", 2011, by Ainsworth B E, Haskell W L, Herrmann S D, Meckes N, Bassett Jr D R, Tudor-Locke C, Greer J L, Vezina J, Whitt-Glover M C, Leon A S), and said relationship (e.g. Calories burned per second equal to the user Weight (in Kg) multiplied by MET/3600, where MET is well known (e.g. MET for walking equals 1 plus velocity in mph times 0.7663 if velocity lower than 3.5, or −6.69 plus velocity in mph times 2.642 otherwise)) may be leveraged in some embodiments in order to determine the calories per time unit burned by a mobile device user), or any other (e.g. calories burned by the user equal the calories burned per time unit multiplied by the time under consideration (e.g. time unit=second)). Some embodiments may leverage the determine_gait_parameters method to compute only a few of said gait parameters (e.g. only velocity, cadence and activity), and compute additional parameters (e.g. stride length, calories burned, etc.) in additional methods (or in any other place within the application) leveraging the determined velocity, cadence and activity, in a way that all parameters are determined in real time with an update frequency larger than the user's step frequency; other embodiments may leverage the determine_gait_parameters method to compute all desired parameters (e.g. velocity, calories burned per time unit, cadence, activity and stride length, and any others) directly, also in real time with an update frequency larger than the user's step frequency; some embodiments may leverage any techniques/methodologies (e.g. upsampling, downsampling, filtering of any kind, use of specific time windows (with specific overlapping factors) to hold sensor values before the time window of those sensor values is being processed to determine parameters, and/or any other, and/or any variations and/or combinations thereof) to control the time intervals between determinations of parameters (or to control the determination update frequency), allowing determination in real time with an update frequency larger than the user's step frequency, or lower than the user's step frequency, or any other, following any criteria. Some embodiments may use any variations and/or combinations thereof.

Regarding the activity of the device user, some embodiments may determine it in real time within the determine_gait_parameters method, leveraging the acceleration values (or any sensor values), which may be processed over a desired time window or in any other way, together with other gait parameters already determined within said method (e.g. velocity, cadence, stride length, calories burned per time unit and/or any others, although some embodiments may not use all or any of these gait parameters), and/or any additional parameters computed making use of any of the previously referred inputs (e.g. mean and/or variance and/or standard deviation and/or skew and/or kurtosis and/or principal frequency component and/or energy in selected frequency bands, and/or any other obtained from acceleration (and/or any other sensor(s) values) signal vector module over a selected time window (e.g. 4 seconds time window), and/or from x,y,z components of acceleration (and/or any other sensor(s) values) over a selected time window (e.g. 4 seconds time window) or any other); in some embodiments all said parameters may be computed in real time within the determine_gait_parameters method, for example after determining the user's velocity, cadence, stride length and calories burned per time unit, and all (or some of them) may be leveraged as features to compute activity by means of a model (in some embodiments it may be a simple formula or a simple structure of conditionals or more complex structures or any other) generated (e.g. offline in a desktop PC, or directly within the device using appropriate software, or any other way and/or variations and/or combinations thereof) using machine learning or any other algorithms/methods and training data previously gathered from volunteers replicating/performing the range of activities (and/or any gait characteristics/attributes (e.g. velocity, cadence, stride length, calories burned per time unit, etc.) and/or any other such as the position of the device) we try to recognize using the device while their data on acceleration (and/or any other sensor(s) values), the type of activity (and/or values of gait attributes such as velocity, cadence, stride length, calories burned per time unit, device position, etc.) and any other parameters (including the features) are being recorded to create a training set; by way of example without limitation, any of the available software packages (e.g. MATLAB and Toolboxes, python and modules, weka, etc.) may be leveraged for modeling purposes (e.g. the model may be obtained leveraging the training set and using support vector machine, Naive Bayes, k-nearest neighbors, decision trees, random forests, logistic regression, linear regression or any other method/algorithm and/or any variations and/or combinations thereof, depending on criteria including without limitation: type and number of activities (and/or gait attributes and/or others) we try to recognize, accuracy, complexity, qualities of training set, and/or any other); an example of embodiment may use support vector machine to recognize between walking (e.g. coded with value 0) and running (e.g. coded with value 1), while other embodiments may use any alternative methods (and recognize any other activities, e.g. walking, jogging, jumping, cooking, household activities, running, cycling, driving, or any other), and some embodiments may leverage as features to determine activity and/or any gait attribute (e.g. velocity, stride length, cadence, calories burned per time unit, device position, and/or any other): 1) the user's velocity and the user's cadence, or 2) the user's velocity and the user's cadence and the mean, standard deviation, principal frequency component and energy in selected frequency bands of the acceleration (and/or any other sensor(s) values, and again, taken as x,y,z components and/or signal vector module) over a desired time window, or 3) the user's velocity and the user's cadence and the mean, variance, standard deviation, skew, kurtosis, principal frequency component and energy in selected frequency bands of the acceleration (and/or any other sensor(s) values, and again, taken as x,y,z components and/or signal vector module) over a desired time window, or 4) the mean, variance, standard deviation, skew, kurtosis, principal frequency component and energy in selected frequency bands of the acceleration (and/or any other sensor(s) values, and again, taken as x,y,z components and/or signal vector module) over a desired time window, or 5) any or all of the previous features and/or any other additional ones, and/or any variations and/or combinations thereof. In some embodiments any or all of said features may be determined in real time with an update frequency larger than the user's step frequency, and leveraging said features the user's activity (and/or any gait attribute (e.g. velocity, stride length, cadence, calories burned per time unit, device position, and/or any other)) may be determined in real time with an update frequency larger than the user's step frequency. In some embodiments, the determined user's activity may be used to control the activity of the user's representation on the device screen in real time with an update frequency larger than the user's step frequency: by way of example, by selecting an appropriate images strip file whose frames are to be displayed on the device screen (e.g., if activity is "walking" (e.g. coded as 1), then the images strip file may be any of FIG. 9A, 9B, 9C, 9D or any other representing a walking activity; or if the activity is "running" (e.g. coded as 2), then the images strip file may be any of FIG. 9E, 9F, or any other representing a running activity, etc.).

By way of example without limitation, some embodiments may employ the same (or similar) procedure described above for the determination of activity, to determine in real time and with an update frequency larger than the user's step frequency, the velocity (and/or cadence an/or calories burned per time unit and/or stride length and/or device position and/or any other attribute) of the user, as described in application Ser. No. 16/044,833.

It is interesting to note that the last block of 8 lines in FIG. 13 summarizes the way some embodiments may handle the change in the user's cadence through the variable completeAnimationPeriod, which may be used to select the appropriate frame from the appropriate images strip file to be displayed on the device screen to adequately control the cadence of the user's representation on the device screen (as shown for example in the manageCurrentFrame method defined in FIG. 11A); in other words, completeAnimationPeriod is programmatically changed (if needed, that is, if the newly determined value and the previous value are different, in which case the time reference value of frame_0_ StartTime will also be accordingly updated) leveraging the newly determined value of cadence; as shown in FIG. 11A, the value of completeAnimationPeriod will control the value of the currentFrame variable; in other words, by changing the value of completeAnimationPeriod, we are controlling the frame to be displayed on the device screen (and thus, how fast a new frame is to be displayed: for example, if we keep the same value of currentFrame during many consecutive calls to the manageCurrentFrame method (typically called within the doDraw method at a specific frequency of, for instance, 60 Hz), then the transition between consecutive frames will be slow, thus giving the illusion of a low value of cadence; on the other hand, if we keep the same value of currentFrame during very few consecutive calls to the manageCurrentFrame method, the transition between consecutive frames will be fast, thus giving the illusion of a high value of cadence); in this example of embodiment, we may be updating completeAnimationPeriod every time cadence is determined (e.g. update frequency may be equal to accelerometer sampling rate, which may be e.g. 60 Hz); since the value of the currentFrame variable may typically be updated with a frequency of 60 Hz (every time manageCurrentFrame is called from the doDraw method), we have fine control over the value of currentFrame, because we can keep repeating the same value of currentFrame for longer periods of time when completeAnimationPeriod is large, but we will quickly transition to the next values of currentFrame when completeAnimationPeriod is short, thus achieving control over the cadence of the user's representation on the device screen. In simple words, when the user's cadence is large (completeAnimationPeriod is short), the values of currentFrame will change quickly (time difference between consecutive frames being displayed will be small, thus achieving high cadence of the representation displayed on the device screen); on the other hand, when the user's cadence is low (completeAnimationPeriod is long), the values of currentFrame will change slowly (time difference between consecutive frames being displayed will be large, thus achieving low cadence of the representation displayed on the device screen); consequently, the device user's determined cadence controls the user's representation cadence in real time, and with an update frequency that may be larger than the user's step frequency.

Again, some embodiments may use any variations and/or modifications and/or combinations of any said elements, concepts, procedures, methods, or any other additional ones, in any fashion. Definitions and/or further details for each one of the concepts, terms, etc. can be found online (e.g. developer.android.com or any other website).

Figure 12:
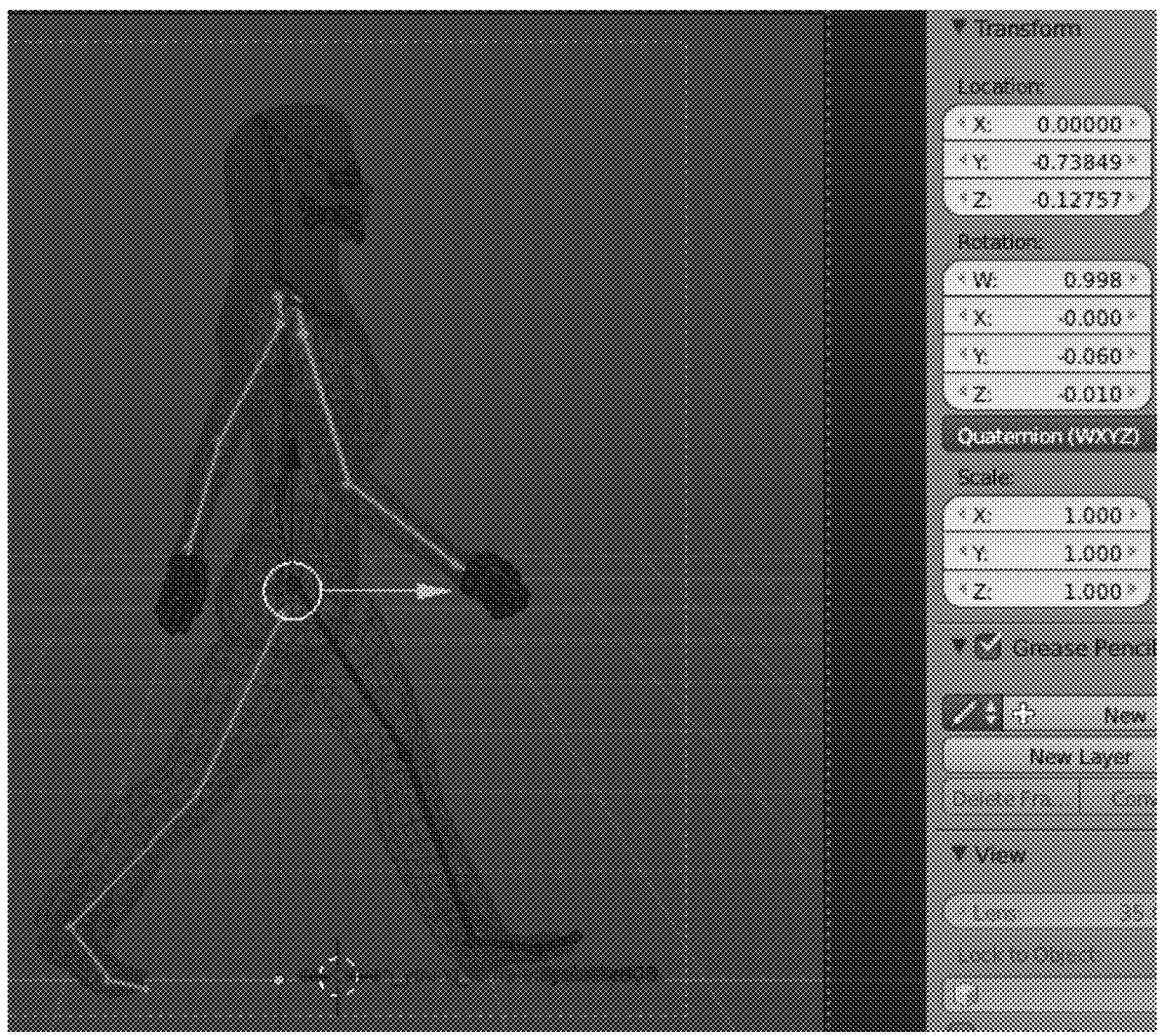
FIG. 12 illustrates part of the user interface of the open-source 3D computer graphics software Blender used in one embodiment.

FIG. 12 shows a screenshot of part of the Blender software's user interface that may be used in some embodiments. Blender is a professional, free and open-source 3D computer graphics software toolset used for creating animated films, visual effects, art, 3D printed models, interactive 3D applications and video games. Blender's features include 3D modeling, UV unwrapping, texturing, raster graphics editing, rigging and skinning, fluid and smoke simulation, particle simulation, soft body simulation, sculpting, animating, match moving, camera tracking, rendering, motion graphics, video editing and compositing. It also features an integrated game engine. In other embodiments, any other type of motion graphics and animation and/or 3D computer graphics and/or any other software (including by way of example without limitation, Autodesk, DAZ Studio, Shark 3D, MakeHuman, Unity) may be used (including in combination with Blender and/or any other) for any purposes, including the creation of a mesh (or set of joint surfaces) to form the 3D model leveraged to represent the mobile or wearable device user, and its integration with an skeleton (or set of joint bones) to control the movement of any part of the 3D model's body (e.g. see FIG. 12), and/or any other. In an example of embodiment, Blender may be used to create each one of the 26 frames composing the images strip files of FIG. 9A, 9B, 9C, etc. For instance, a 3D model (mesh structure and some bones used to control some of its features may be seen in FIG. 12, showing on the right side the x,y,z location, w,x,y,z quaternion rotation, x,y,z scale of an element selected from the 3D body on the left) may be leveraged and appropriately positioned in a scene to be rendered with the desired features, attributes, etc.; by way of example without limitation, each one of the elements (from the surfaces composing the mesh forming the model to each one of the bones controlling the attributes of different parts of the body) composing the 3D model, can be modified in different ways by the designer; for instance, the color, texture, materials (e.g. type of cloth), etc. of the surfaces composing the mesh forming the model can be controlled by the designer, or the location (3D coordinates x,y,z), rotation (quaternion w,x,y,z), scale (x,y,z) of the different parts of the body can be controlled by the designer, making use of, for instance, the bones and/or joints intended for controlling the body parts. For example, by appropriately choosing the location and rotation of the bones (and/or their edges and/or the joints) in the legs and feet, the stride length may be controlled; analogously, by appropriately choosing the location and rotation of the bones (and/or their edges and/or the joints) in the arms and hands, the swinging of the hands and arms may be controlled; the same applies to any other feature and/or attribute of the 3D model, which in some embodiments may have over 70 bones, each one for a particular part of the body, while other embodiments may have even larger number of bones to increase the level of control. By way of example without limitation, features and/or attributes in the 3D model that may be controlled by the designer in some embodiments may include: location, rotation and scale of any part of the body, color, texture, material, etc. of the different surfaces composing the mesh forming the model, stride length, swing of arms, bouncing of any soft parts of the body (e.g. hair bouncing with the movement), and/or any other and/or any variations and/or combinations thereof. By way of example without limitation, a particular embodiment may control the stride length, the locations and rotations of all the bones in the feet, legs, spine, hips, back, arms, hands, neck and head, the bouncing of the hair, the color and/or texture of the skin in order to control the appearance of sweat in skin and/or clothes and/or any other way to indicate any level of caloric consumption (e.g. calories burned per time unit, calories burned during a determined period of time, and/or any other) due to the exercise (e.g. gait activity). It is also worth noting that control of any attributes and/or features of the 3D model and/or any other object represented in the scene or control of the 3D model as a whole can be programmatically done (also in real time animations) by means of software (e.g. assigning the different values of x,y,z coordinates controlling the location of each body part (e.g. using their bones and/or their edges and/or the joints) to different variables in a software program, and/or assigning the different values of w,x,y,z quaternion controlling the rotation of each body part to different variables, and/or assigning the different values of x,y,z scaling factors controlling the size of each body part to different variables, etc.) to achieve the effect or illusion of animation and/or any other. In some embodiments, each one of the frames (e.g. static screenshots) constituting an animation may be rendered into pictures files (e.g. png extension files, or any other) using Blender, and said frames may be placed consecutively (e.g. ordered by sequence time) to obtain an images strip file such as FIG. 9A, 9B, 9C, 9D, 9E, 9F, and/or any other. For any of said purposes, any of the mentioned software packages and/or any other (e.g. Photoshop and/or any other raster graphics editor, and/or any of their plugins, etc.) may also be leveraged.

Some embodiments may leverage time domain windows to process the accelerometer (and/or any other sensor(s)) measurements, where the time length of said windows may be such (e.g. 2, 3, 4, 5, 6, 7, 8, 20, 40 seconds or any other length) that the amount of accelerometer (and/or any other sensor(s)) samples (e.g. having chosen a particular sampling frequency, or using upsampling/downsampling/filtering/thresholding and/or any other technique to process the read raw samples and obtain new processed samples at a fixed desired sampling rate) processed for the determination of the user's gait (or any other type) attribute(s) (e.g. velocity, cadence, stride length, calories burned per time unit, activity, device position and/or any other and/or any combinations thereof) is fixed at a particular value. By way of example without limitation, some embodiments may determine said attributes leveraging (processing) windows containing a fixed amount (e.g. called "amount_of_samples") of sensor (e.g. accelerometer and/or any other type) samples, where the sensor samples may correspond e.g. to each one of the x,y,z components and/or the signal vector module (square root of summation of squared components) of the sensor. In an example of embodiment, said windows or groups of samples of fixed size (amount_of_samples) may be created and held in the application leveraging the sensor measurements read from the sensor(s), and applying any technique if needed (e.g. upsampling/downsampling/filtering/thresholding and/or any other) to achieve the quantities desired, and using any required data structure (e.g. arrays, lists and/or any others and/or combinations thereof) to hold them for processing. For instance, if the sensor (e.g. accelerometer) sampling rate is fixed and constant at 46.5 Hz and we use time windows of 4 seconds, we may achieve a group (or groups (e.g. x,y,z components and/or signal vector module)) of 46.5 (samples/second)*4 (seconds)=186 samples; once we obtain the 186 samples, we can e.g. store them in an array (or arrays if we have several groups) that may be used as input for a method in the application (e.g. determine_gait_parameters in FIG. 13) in order to process them to determine the desired user's attribute(s). By way of example without limitation, we may achieve groups of 186 samples (e.g. using 4 seconds windows at 46.5 Hz sampling rate, or any other combinations of window length and sampling rate (e.g. 2 seconds at 93 Hz, 3 seconds at 62 Hz, etc.)) for each one of the x, y, z components of the accelerometer in the device, and store those values in arrays (e.g. array_x, array_y, array_z); next, we obtain another group of 186 samples for the signal vector module of the acceleration (square root of summation of squared x, y, z components), and store those 186 values in another array (e.g. array_svm); next we pass those 4 arrays (array_x, array_y, array_z, array_svm) as inputs parameters to the determine_gait_parameters method to process them in order to obtain the desired gait attributes.

We may also use any desired amount of overlapping to keep creating/holding/storing/processing groups of 186 samples at a desired frequency; for example, we may keep the newest 93 of the 186 samples (e.g. 50% overlapping) to create a new group (e.g. every 2 seconds), or we may discard the oldest 9 of the 186 samples (e.g. —95% overlapping) to create a new group (e.g. every ~0.2 seconds), thus enabling the determination of the user's attribute(s) in real time and with an update frequency larger than the user's step frequency. Regarding the processing of said groups (or arrays) of 186 samples of sensor (e.g. accelerometer) data, some embodiments may leverage any of the techniques/approaches/methodologies/pre-processing/strategies/procedures, etc. described within this application and/or any others and/or any variations and/or combinations thereof to determine any or all of the desired gait attribute(s) (e.g. velocity, cadence, stride length, calories burned per time unit, activity, device position, etc.) and/or for any other purposes; by way of example without limitation, some embodiments may process any or all of said groups of 186 samples (and/or any other groups in any number) of accelerometer data leveraging wavelet transformation, selecting, for instance, as transformation parameters: a mother wavelet from any of Haar, or Daubechies, or Coiflets, or discrete version of Meyer, and a number of levels of decomposition sufficient to account for the frequency bands we expect. In a particular example, we may apply the wavelet transformation to said groups of 186 samples using Haar mother wavelet and eight levels of decomposition; in another example of embodiment, we may apply the wavelet transformation to said groups of 186 samples using Daubechies type 3 as mother wavelet and six levels of decomposition. Other embodiments may use any other values/numbers/qualities for any of the referred elements/quantities/variables and/or any other, including any variations and/or combinations thereof, and/or any other approaches/methodologies. Consequently, some embodiments may process groups of 186 samples of sensor data for the determination of the desired gait attributes, and some embodiments may process groups of 186 samples of sensor data using Daubechies type 3 as mother wavelet and six levels of decomposition.

Some embodiments may apply any of the mentioned approaches/strategies/methodologies, etc. for any other purposes, including the controlling of any attributes of any elements in FIG. 1C or FIG. 2B or any others. By way of example without limitation, other embodiments may use different numbers of image strip files, representing different or same type of activities, and each images strip file may contain different number of frames; any variations and/or combinations of any aspect and/or element and/or any additional elements and aspects are also possible. Multiple additions and/or variations and/or alternatives and/or combinations thereof are also possible in some embodiments. Other embodiments may use any other variations and/or combinations of any of said elements/devices/specifications/characteristics/tools/variables/initializations/methods/approaches/techniques and/or any other (hardware/software) tools/library/API, or any other in any fashion and for any purpose, including by way of example without limitation, achieving similar or different and/or variations and/or combinations of any effects described above.

Some embodiments may use any type of smartphones, mobile devices, wearable devices and/or sensors, or any other types of devices or combinations of them, including but not limited to, personal digital assistants, personal navigation systems, portable electronic devices, tablets, laptops, computers, and their peripheral devices. In some embodiments, the definition of mobile device may comprise any type of mobile phone, smartphone, wearable device and/or sensor, or any other types of device or wearable or combinations of them.

Some embodiments may use combinations of strategies and techniques, including, by way of example, and not limitation, machine learning techniques, probabilistic models, sensor fusion techniques, extraction of statistics, employment of filter banks, application of dimensionality reduction techniques, a variety of approaches for classification, etc. Details are omitted to improve the clarity of the description. In addition, some embodiments may use a variety of programming languages and methodologies in combination with varied hardware configurations and execution strategies.

Applications of some embodiments may comprise monitoring a variety of information of people in a variety of circumstances or contexts, including but not limited to, health-care, army, sports, etc., as described in application Ser. No. 16/044,833.

It is also worth noting that in some embodiments, the user's representation may be displayed/rendered/placed/projected on a place different from the device screen (e.g. it may be projected over a surface within or outside the device, or it may be rendered on a display/screen or any kind of projection/rendering electronics outside the device (e.g. a wall, other device, etc.)).

Threads are the cornerstone of any multitasking operating system and can be thought of as mini-processes running within a main process, the purpose of which is to enable at least the appearance of parallel execution paths within applications. By way of example without limitation, when an Android application is first started, the runtime system creates a single thread in which all application components will run by default. This thread is generally referred to as the main thread. The primary role of the main thread is to handle the user interface in terms of event handling and interaction with views in the user interface. Any additional components that are started within the application will, by default, also run on the main thread. Any component within an application that performs a time consuming task using the main thread may cause the entire application to appear to lock up until the task is completed; in some embodiments, this may be avoided simply by launching the task to be performed in a separate thread, allowing the main thread to continue unhindered with other tasks. In other words, some embodiments may avoid performing time-consuming operations (e.g. determining a user's gait characteristic, such as velocity and/or cadence and/or stride length and/or activity and/or calories burned per time unit and/or step count and/or device position and/or status of a medical condition and/or any other, and/or controlling an aspect of an application, such as inserting a new measurement of any of the referred user's gait characteristics or any others into a time chart representing the real time evolution of said gait characteristic, and/or selecting a frame (or a strip of images/frames) to be displayed based on the determined gait characteristic(s) and/or any other criteria and/or any other type of controlling and/or any variations and/or combinations thereof) on the main thread of an application. In order to create a new thread (e.g. a separate thread, or a thread separate from the main thread), the task or code to be executed in that thread needs to be placed within the run( )method of a runnable instance. A new thread object then needs to be created, passing through a reference to the runnable instance to the constructor. Finally, the start( )method of the thread object needs to be called to start the thread running. All these known concepts and others are further described in references such as: www.techotopia.com/index.php/A_Basic_Overview_of_Android_Threads_and_Thread_handlers, developer.android.com, "Multi-threaded Programming with Java Technology" by Bil Lewis, Prentice Hall, 2000, or "Taming Java Threads" by Allen Holub, Apress, Jun. 1, 2000, or "Multithreading Programming Techniques" by S. Prasad, McGraw-Hill, 1996, or "The art of multiprocessor programming" by Herlihy, Maurice, and Nir Shavit. Morgan Kaufmann, 2011, all of which are hereby incorporated by reference in their entireties for all purposes. By way of example without limitation, the following lines:

```
Thread slowThread = new Thread(new Runnable( ) {
  @Override
  public void run( ) {
    while (!Thread.interrupted( )) {
      determine_gait_parameters( );
    }
  }
});
slowThread.start( );
```

Schematically represent an example of structure of schematic pseudocode that could help the skilled reader to implement a thread to be used in some embodiments to perform the task of the method "determine_gait_parameters" within a new (separate) thread called "slowThread", which is started using "slowThread.start( );". In some embodiments, we may substitute the determine_gait_parameters method by the setAnimationImagesStrip method or any other responsible for a controlling task, so that instead of determining gait characteristic(s), we would be controlling an aspect of an application or one or more attributes of a user's representation with the determined gait characteristic(s). In some embodiments, by way of example without limitation, this type of structure (or any others as shown in the many examples included with the mentioned references, and/or any variation and/or any combinations thereof) could be used in any way as described in any of the mentioned references.

By way of example without limitation, some embodiments may use the application's main thread or a separate thread or multiple separate threads (different from the main thread of the application) to launch tasks such as: determining any number of the user's gait characteristics such as velocity, cadence, step length, step count, calories burned per time unit, activity, device position, status of a medical condition, and/or any other of any type; for instance, said determining can be performed leveraging the determine_gait_parameters method of FIG. 13; consequently the determine_gait_parameters method would be called in some embodiments from within a separate thread (please remember, a separate thread is a thread different from the main thread). Some embodiments may use any other elements and/or methods and/or techniques and/or attributes and/or characteristics and/or any others and/or any variations and/or combinations thereof. In some embodiments, tasks for the determining of the user's gait characteristic(s) can be performed at a selected update frequency which can be different from the accelerometer sampling rate; for example, some embodiments may wait for a selected amount of time (e.g. wait(amount_of_time)) before the determining task is launched, or some embodiments may skip a selected number of accelerometer samples to perform the determination of the gait characteristic(s) with an update frequency lower than the accelerometer sampling rate (e.g. if every other accelerometer sample is skipped, we can determine the gait characteristic using every non-skipped accelerometer sample, thus achieving an update frequency for the determination equal to half the accelerometer sampling rate), or some embodiments may use any other techniques and/or methodologies (e.g. any filtering, upsampling, downsampling, and/or any other technique) and/or any variations and/or combinations thereof. Next, a series of examples of embodiments will be presented describing the update frequency of the determining of the user's gait characteristic(s); it is interesting to note that, in some cases, by way of example without limitation, said embodiments may be applicable regardless of the thread (e.g. main thread or a separate thread(s)) from which the determining task is launched; in other words, in some embodiments, the following examples may be applied when the task of determining the user's gait characteristic is launched from the main thread or when the task of determining the user's gait characteristic is launched from a separate thread. It is interesting to note that throughout this whole specification, when we refer to gait characteristic or gait characteristics, we may refer to any or all of velocity and/or cadence and/or stride length and/or activity and/or calories burned per time unit and/or device position and/or status of a medical condition of the user and/or step count and/or any other and/or any variations and/or combinations thereof.

As used herein, the term "frequency band of a gait activity" refers to the range of frequencies spanned by typical cadences of average users performing said gait activity. For example, in some embodiments, a frequency band of the gait activity of the user may span the range of frequencies at which average users typically perform the activity; by way of example without limitation, if the gait activity is walking, the range of frequencies for typical users may span in some embodiments from e.g. 0.25 Hz to 2.3 Hz, while in other embodiments it may span from e.g. 0.3 Hz to 2.35 Hz, depending on a variety of criteria (e.g. age of the users, health status of the users, height and weight of the users, etc.); in some embodiments the range of frequencies can be determined through tests/experiments with the users; by way of example without limitation, the scientific report "The role of stride frequency for walk-to-run transition in humans" by E. A. Hansen et. al, available online at www-.nature.com/articles/s41598-017-01972-1 states that a calculated walk-to-run transition stride frequency may be approximately 70.6 strides/minute, which is approximately a step frequency of 2.35 Hz; some embodiments may choose a higher upper limit (e.g. 2.5 Hz or 3 Hz) as a precaution to make sure that the step frequency still corresponds to walking; consequently some embodiments may select a walking frequency band of e.g. 0.25 Hz to 3 Hz; similar reasoning may be applied to other types of gait activity, such as running, where some embodiments may select a running frequency band of e.g. 2.35 Hz to 7 Hz, while other embodiments may chose different values (e.g. as a precaution to make sure that the step frequency still corresponds to running, some embodiments may select a running frequency band of e.g. 2.5 Hz to 8 Hz); other embodiments may obtain the frequency band of the gait activity of a user or of a group of users through experimentation, and adapt the edges accordingly; other embodiments may use any variations and/or combinations thereof.

Some embodiments may set the update frequency of the determining of the gait characteristic as a constant value regardless of the sampling frequency of the device accelerometer, which may be variable/dynamic (e.g. it may not maintain a perfectly constant sampling rate over time, due to any reason such as hardware configuration, and/or computation burden in the device, and/or software configuration, and/or any other and/or any combinations thereof) or set dynamically in some embodiments (e.g. some embodiments may change the sampling rate depending on the user's activity; e.g. if the user is running, the sampling rate may be set higher than if the user is still), while it may be constant in other embodiments; by way of example without limitation, determining the gait characteristic leveraging the device accelerometer samples can be performed at a constant frequency; for example, we may set a fixed time interval (period of the determining, which is the inverse of the frequency of the determining) for determining the gait characteristic, and the accelerometer samples leveraged for the determining may be, for example, those contained in a window of a selected length of time (e.g. 10 seconds, or 20 seconds, or any other) up until the actual time instant of the determining; in some embodiments we may use any type of filtering and/or upsampling and/or downsampling and/or any other techniques to obtain, from the actual accelerometer generated samples, a constant amount of samples (e.g. processed samples) at every period of the determining of the gait characteristic; for example, if the accelerometer is generating samples at 60 Hz, and our period for determining the gait characteristic is 33 milliseconds (determining frequency=30 Hz; please know rounding may be used in some quantities for clarity), and we want one new processed sample at every determining period, we may skip every other accelerometer sample, and determine the gait characteristic at a constant update frequency of 30 Hz; for example, if the accelerometer is generating samples at 15 Hz, and our period for determining the gait characteristic is 33 milliseconds (determining frequency=30 Hz), and we want one new processed sample at every determining period, we may repeat every accelerometer sample, and determine the gait characteristic at a constant update frequency of 30 Hz; some embodiments may use any other techniques, such as any type of filtering and/or upsampling and/or downsampling and/or interpolation and/or averaging and/or any variations and/or combinations thereof. Consequently, in some embodiments we may set the update frequency of the determining of the gait characteristic as a constant value (e.g. 30 Hz or 60 Hz or 120 Hz or 14 Hz or any other value) while the sampling frequency of the device accelerometer is variable or is set dynamically (e.g. from 60 Hz to 15 Hz or any other values); in some embodiments the accelerometer sampling rate may be set dynamically depending on the determined user's activity (e.g. 60 Hz for running, 50 Hz for walking, 40 Hz for standing, and/or any other values and/or activities and/or choices and/or any variations and/or combinations thereof). Some embodiments may use any other values and/or techniques and/or elements and/or any variations and/or combinations thereof. Some embodiments may set the update frequency of the determining of the gait characteristic as a constant greater than the upper edge of the frequency band of the gait activity of the user (e.g. if the user's gait activity is walking, said update frequency may be set as e.g. 3.5 Hz, or 9 Hz, or 60 Hz, or 120 Hz, or any other value; if the user's gait activity is running, said update frequency may be set as e.g. 8.5 Hz, or 12 Hz, or 60 Hz, or 120 Hz, or any other value); in some embodiments, setting update frequencies above the upper edge of the frequency band of the gait activity of the user may be useful to be able to e.g. detect or account for details that may occur at high frequencies of said band. Similar reasoning may be extended in some embodiments to set the update frequency of the determining of the gait characteristic as a constant value (or variable value in other embodiments) greater than the upper edge of the frequency band of the gait activity of the user and lower than the device accelerometer sampling rate; by way of example without limitation, we may have an accelerometer sampling rate of 60 Hz, but we may set the update frequency of the determining of the gait characteristic as a constant value (or variable value in other embodiments) below that rate (e.g. constant at 30 Hz, or 20 Hz, or 10 Hz or any other value, and regardless of the user's activity; or variable at 30 Hz while the user is running, 20 Hz while the user is walking, and 10 Hz while the user is still) and greater than the upper edge of the frequency band of the gait activity of the user (e.g. 3 Hz if the user's gait activity is walking, or 8 Hz if the user's gait activity is running). In some embodiments we may set the update frequency of the determining of the gait characteristic as a constant value (or variable value in other embodiments) greater than the upper edge of the frequency band of the gait activity of the user and lower than the device accelerometer sampling rate, while the sampling frequency of the device accelerometer is variable or is set dynamically; for example, we may have an accelerometer sampling rate of 60 Hz, but we may set the update frequency of the determining of the gait characteristic as a constant (or variable in other embodiments) value (e.g. 20 Hz, or 10 Hz or any other value, following the example above) below the accelerometer sampling rate and greater than the upper edge of the frequency band of the gait activity of the user (e.g. greater than 3 Hz if the user's gait activity is walking, or greater than 8 Hz if the user's gait activity is running), and if the accelerometer sampling rate is varied (e.g. reduced to 25 Hz), we may keep the previously set update frequency of the determining of the gait characteristic constant (or variable in other embodiments) (e.g. 20 Hz, or 10 Hz, or any other value) and still below the accelerometer sampling rate and greater than the upper edge of the frequency band of the gait activity of the user (e.g. 3 Hz if the user's gait activity is walking, or 8 Hz if the user's gait activity is running).

It is interesting to note that in some embodiments we may try to minimize any computation burden on the main thread (or thread in charge of the user interface and/or aspects such as refreshing of screen (or frames)) of the application, so we may launch the task of determining the gait characteristic(s) from a separate thread with a selected update frequency, which in some embodiments may be different from the frame (or screen) refresh rate; by way of example without limitation, if the frame (or screen) refresh rate is 25 Hz, we may determine the gait characteristic(s) from a separate thread with an update frequency of e.g. 20 Hz or 60 Hz or 120 Hz (e.g. waiting for a specific amount of time to launch the determining task with the desired periodicity (e.g. waiting 50 milliseconds to launch determine_gait_parameters if we want an update frequency of 20 Hz), or using any of the methods mentioned in this specification or any others). In other embodiments we may still determine the gait characteristic(s) from the main thread but with an update frequency different from the frame (or screen) refresh rate; for example, if the frame (or screen) refresh rate is 25 Hz, we may launch the task of determining the gait characteristic(s) from within the main thread but with a specific periodicity, or specific update frequency, thus updating at e.g. 20 Hz or 60 Hz or 120 Hz (e.g. as explained before); by way of example without limitation, we may launch the task of determining the gait characteristic(s) from within the onSensorChanged method of FIG. 13 (e.g. with an update frequency equal to the accelerometer sampling rate (e.g. 60 Hz or 20 Hz or any other value), which may be different from the frame (or screen) refresh rate (e.g. 25 Hz)). Consequently, in some embodiments, the update frequency of the determining of the gait characteristic(s) may be different from the application's frame (or screen) refresh rate (e.g. lower or higher than the frame (or screen) refresh rate), and this may be achieved launching the task of determining the gait characteristic(s) from within the main thread of the application or from within a separate thread of the application, and all this may be achieved in some embodiments while 1) setting the update frequency of the determining of the gait characteristic as a constant value (or variable in other embodiments) while the sampling frequency of the device accelerometer is variable or is set dynamically, and/or 2) setting the update frequency of the determining of the gait characteristic as a constant (or variable in other embodiments) value greater than the upper edge of the frequency band of the gait activity of the user and lower than the device accelerometer sampling rate and/or 3) setting the update frequency of the determining of the gait characteristic as a constant (or variable in other embodiments) value greater than the upper edge of the frequency band of the gait activity of the user and lower than the device accelerometer sampling rate, while the sampling frequency of the device accelerometer is variable or is set dynamically. Some embodiments may use any other techniques and/or approaches and/or methodologies and/or any variations and/or combinations thereof, including any combinations with any of the possible values and/or variations and/or combinations of update frequency of any controlling with the gait characteristic(s).

By way of example without limitation, some embodiments may use the application's main thread or a separate thread or multiple separate threads (different from the main thread of the application) to launch tasks such as: controlling an aspect of an application and/or controlling one or more attributes of a user's representation (e.g. velocity and/or cadence and/or stride length and/or step count and/or calories burned per time unit and/or activity and/or device position and/or status of a medical condition, and/or any other of any type, such as the color of the skin and/or the bouncing of the hair and/or the rotation angles of the limbs and/or the movements of the head and/or the movements of the hands, etc of the user's representation, and/or any others and/or any variations and/or combinations thereof) with any or all of the determined user's gait characteristics (e.g. velocity and/or cadence and/or stride length and/or step count and/or calories burned per time unit and/or activity and/or device position and/or status of a medical condition, and/or any others and/or any variations and/or combinations thereof) by selecting the appropriate frame to be displayed and/or by selecting the appropriate strip of frames for displaying the user's representation; for instance, in some embodiments the selecting of the appropriate strip of frames may be performed leveraging the setAnimationImagesStrip method of FIG. 11B; consequently the setAnimationImagesStrip method may be called in some embodiments from within a separate thread (different from the main thread). Some embodiments may use any other elements and/or methods and/or techniques and/or attributes and/or characteristics and/or any others and/or any variations and/or combinations thereof.

In some embodiments, tasks for the controlling of an aspect of the application and/or for the controlling of one or more attributes of a user's representation with the determined user's gait characteristic(s) can be performed at a selected update frequency which can be different from the accelerometer sampling rate; for example, some embodiments may wait for a selected amount of time (e.g. wait (amount_of_time)) before the controlling task is launched, or some embodiments may skip a selected number of accelerometer samples before launching the controlling task, thus performing the controlling with an update frequency lower than the accelerometer sampling rate (e.g. if every other accelerometer sample is skipped before we launch the controlling task, we can perform the controlling with the determined gait characteristic every non-skipped accelerometer sample, thus achieving an update frequency for the controlling equal to half the accelerometer sampling rate), or some embodiments may use any other techniques and/or methodologies (e.g. any filtering, upsampling, downsampling, and/or any other technique) and/or any variations and/or combinations thereof. Next, a series of examples of embodiments will be presented describing the update frequency of the controlling of an aspect of the application and/or the controlling of one or more attributes of a user's representation with the determined user's gait characteristic(s); it is interesting to note that, in some cases, by way of example without limitation, said embodiments may be applicable regardless of the thread (e.g. main thread or a separate thread(s)) from which the controlling task is launched; in other words, in some embodiments, the following examples may be applied when the task of controlling is launched from the main thread or when the task of controlling is launched from a separate thread. It is interesting to note that throughout this whole specification, when we refer to gait characteristic or gait characteristics, we may refer to any or all of velocity and/or cadence and/or stride length and/or activity and/or calories burned per time unit and/or device position and/or status of a medical condition of the user and/or step count and/or any other and/or any variations and/or combinations thereof.

Some embodiments may set the update frequency of the controlling of an aspect of the application and/or controlling of one or more attributes of a user's representation with the determined user's gait characteristic(s) as a constant value (or variable value in other embodiments) regardless of the sampling frequency of the device accelerometer, which may be variable or set dynamically in some embodiments, while it may be constant in other embodiments; by way of example without limitation, controlling can be performed at a constant (or variable in other embodiments) frequency (e.g. constant at 8 Hz or 30 Hz or 60 Hz or 120 Hz; or variable by setting a frequency of e.g. 8 Hz while the user is still, 30 Hz while the user is walking, and 60 Hz while the user is running); for example, we may set a fixed time interval (period of the controlling, which is the inverse of the frequency of the controlling) for launching the task of controlling with the determined gait characteristic; for instance, some embodiments may wait for said fixed time interval (period of the controlling, which may be e.g. 50 milliseconds if the controlling update frequency is 20 Hz) to expire before launching the controlling task. In some embodiments we may set the controlling frequency in terms of the sampling frequency of the device accelerometer and launch the controlling task after a selected number of accelerometer samples have been generated, which would result in a controlling frequency equal or lower than the accelerometer sampling frequency (e.g. equal if we launch the controlling at every accelerometer sample, and lower (e.g. by half) if e.g. we launch the controlling at every other accelerometer sample); in other embodiments we may use any type of filtering and/or upsampling and/or downsampling and/or any other techniques to obtain, from the actual accelerometer generated samples, a constant amount of samples (e.g. processed samples) at every period of the controlling; for example, if the accelerometer is generating samples at 60 Hz, and our period for controlling is 33 milliseconds (controlling frequency=30 Hz), and we want one new processed sample at every controlling period, we may skip every other accelerometer sample, and perform the controlling at a constant update frequency of 30 Hz; for example, if the accelerometer is generating samples at 15 Hz, and our period for controlling is 33 milliseconds (controlling frequency=30 Hz), and we want one new processed sample at every controlling period, we may repeat every accelerometer sample, and perform the controlling at a constant update frequency of 30 Hz; some embodiments may use any other techniques, such as any type of filtering and/or upsampling and/or downsampling and/or interpolation and/or averaging and/or any variations and/or combinations thereof. Consequently, in some embodiments we may set the update frequency of the controlling of an aspect of the application and/or controlling of one or more attributes of a user's representation with the determined user's gait characteristic(s) as a constant value (e.g. 30 Hz or 60 Hz or 120 Hz or 14 Hz or any other value) while the sampling frequency of the device accelerometer is variable or is set dynamically (e.g. from 60 Hz to 15 Hz or any other values). Some embodiments may use any other values and/or techniques and/or elements and/or any variations and/or combinations thereof. Some embodiments may set the update frequency of the controlling with the gait characteristic as a constant (or variable in other embodiments) greater than the upper edge of the frequency band of the gait activity of the user (e.g. if the user's gait activity is walking, said update frequency may be set as a constant at e.g. 3.5 Hz, or 9 Hz, or 60 Hz, or 120 Hz, or any other value; if the user's gait activity is running, said update frequency may be set as a constant at e.g. 8.5 Hz, or 12 Hz, or 60 Hz, or 120 Hz, or any other value; in other embodiments choosing a variable value, we may set said update frequency as e.g. 10 Hz if the user is walking, and 20 Hz if the user is running). Similar reasoning may be extended in some embodiments to set the update frequency of the controlling of an aspect of the application and/or controlling of one or more attributes of a user's representation with the determined user's gait characteristic(s) as a constant (or variable in other embodiments) value greater than the upper edge of the frequency band of the gait activity of the user and lower than the device accelerometer sampling rate; by way of example without limitation, we may have an accelerometer sampling rate of 60 Hz, but we may set the update frequency of the controlling with the gait characteristic as a constant value below that rate (e.g. 30 Hz, or 20 Hz, or 10 Hz or any other value) and greater than the upper edge of the frequency band of the gait activity of the user (e.g. 3 Hz if the user's gait activity is walking, or 8 Hz if the user's gait activity is running); embodiments choosing a variable value may set said frequency e.g. at 10 Hz if the user is walking or 20 Hz if the user is running. In some embodiments we may set the update frequency of the controlling of an aspect of the application and/or controlling of one or more attributes of a user's representation with the determined user's gait characteristic(s) as a constant (or variable in other embodiments) value greater than the upper edge of the frequency band of the gait activity of the user and lower than the device accelerometer sampling rate, while the sampling frequency of the device accelerometer is variable or is set dynamically; for example, we may have an accelerometer sampling rate of 60 Hz, but we may set the update frequency of the controlling as a constant value (e.g. 20 Hz, or 10 Hz or any other value) below the accelerometer sampling rate and greater than the upper edge of the frequency band of the gait activity of the user (e.g. greater than 3 Hz if the user's gait activity is walking, or greater than 8 Hz if the user's gait activity is running), and if the accelerometer sampling rate is varied (e.g. reduced to 25 Hz), we may keep the previously set update frequency of the controlling constant (e.g. 20 Hz, or 10 Hz, or any other value) and still below the accelerometer sampling rate and greater than the upper edge of the frequency band of the gait activity of the user (e.g. 3 Hz if the user's gait activity is walking, or 8 Hz if the user's gait activity is running). Embodiments choosing a variable value for the controlling frequency may set it e.g. as 20 Hz while the user is running and 10 Hz while the user is walking, while the accelerometer sampling rate is either 60 Hz or 25 Hz.

It is interesting to note that in some embodiments we may try to minimize any computation burden on the main thread (or thread in charge of the user interface and/or aspects such as refreshing of frames (or screen)) of the application, so we may launch the task of controlling with the gait characteristic(s) from a separate thread with a selected update frequency, which in some embodiments may be different (e.g. lower or higher) from the frame (or screen) refresh rate; by way of example without limitation, if the frame (or screen) refresh rate is 25 Hz, we may perform the controlling with the gait characteristic(s) from a separate thread with an update frequency of e.g. 20 Hz or 60 Hz or 120 Hz (e.g. waiting for a specific amount of time to launch the controlling task with the desired periodicity (e.g. waiting 50 milliseconds to launch the setAnimationImagesStrip method (or any other method for controlling with the determined gait characteristic(s)) if we want an update frequency of 20 Hz), or using any of the methods mentioned in this specification or any others). In other embodiments we may still perform the controlling with the gait characteristic(s) from the main thread but with an update frequency different (e.g. lower or higher) from the frame (or screen) refresh rate; for example, if the frame (or screen) refresh rate is 25 Hz, we may launch the task of controlling with the gait characteristic(s) from within the main thread but with a specific periodicity, or specific update frequency, thus updating at e.g. 20 Hz or 60 Hz or 120 Hz (e.g. as explained before); please note that as used herein, the term "animation frame(s) update frequency" (how often a new frame is displayed) is a different concept/term from the term "screen (or frame(s)) refresh rate" (how often the screen is refreshed, regardless of the content on the screen, which in some embodiments may remain without being updated while it is being refreshed); for example, we may refresh at 60 Hz, but we may update the animation's frames at 30 Hz (thus a same animation frame will be refreshed before any update); in some embodiments both frequencies may be different (e.g. screen (or frame) refresh rate=60 Hz and animation frame update frequency=30 Hz), while in other embodiments they may have the same value (e.g. screen (or frame) refresh rate=60 Hz and animation frame update frequency=60 Hz); other embodiments may use any other values and/or variations and/or combinations thereof; by way of example without limitation, we may launch the task of controlling with the gait characteristic(s) from within the onSensorChanged method of FIG. 13 (e.g. with an update frequency equal to the accelerometer sampling rate (e.g. 60 Hz or 20 Hz or any other value), which may be different from the frame (or screen) refresh rate (e.g. 25 Hz)). Consequently, in some embodiments, the update frequency of the controlling of an aspect of the application and/or controlling of one or more attributes of a user's representation with the determined user's gait characteristic(s) may be different from the application's frame (or screen) refresh rate (e.g. lower or higher than the frame (or screen) refresh rate), and this may be achieved launching the task of controlling with the gait characteristic(s) from within the main thread of the application or from within a separate thread of the application, and all this may be achieved in some embodiments while 1) setting the update frequency of the controlling with the gait characteristic as a constant (or variable in other embodiments) value while the sampling frequency of the device accelerometer is variable or is set dynamically, and/or 2) setting the update frequency of the controlling with the gait characteristic as a constant (or variable in other embodiments) value greater than the upper edge of the frequency band of the gait activity of the user and lower than the device accelerometer sampling rate and/or 3) setting the update frequency of the controlling with the gait characteristic as a constant (or variable in other embodiments) value greater than the upper edge of the frequency band of the gait activity of the user and lower than the device accelerometer sampling rate, while the sampling frequency of the device accelerometer is variable or is set dynamically. Some embodiments may use any other techniques and/or approaches and/or methodologies and/or any variations and/or combinations thereof, including any combinations with any of the possible values and/or variations and/or combinations of update frequency of the determining of the gait characteristic(s); and in some embodiments, both the update frequency of the controlling and the update frequency of the determining may be equal.

It is interesting to note that in some embodiments, by way of example without limitation, a user's representation can be controlled in real time with a gait velocity (and/or cadence and/or activity and/or stride length and/or calories burned per time unit and/or device position and/or step count and/or status of a medical condition and/or any other and/or any variations and/or combinations thereof) of the user, which may be determined in real time; in some embodiments the user's representation can be displayed/shown/presented/represented/illustrated etc. within the user's mobile or wearable device (e.g. on a screen of the device), while in other embodiments the user's representation can be displayed/shown/presented/represented/illustrated etc. outside the user's mobile or wearable device (e.g. on a desktop computer screen, or on a laptop, or projected on a wall or any other surface) and any type of communication and/or connection and/or means and/or any other well known procedures and/or methodologies can be used to link the user and/or the user's device with any external device and/or element where the user's representation is displayed/shown/presented/represented/illustrated etc. For example, a user's representation such as any of those in FIG. 9A to 9F and/or FIG. 10A to 10F and/or FIG. 12 and/or any other Figures and/or any others and/or variations and/or any combinations thereof, can have its velocity controlled by the determined user's gait velocity, and its value can be shown e.g. on a dashboard element such as any of (120) and/or (130) of FIG. 1C, and/or (210) and/or (220) of FIG. 2B and/or any other.

It is interesting to note that throughout the whole of this specification (and any other cross references with which this application is linked), the term velocity or gait velocity may be replaced or substituted by any and/or all and/or any combinations of the following terms: gait cadence and/or activity and/or stride length and/or calories burned per time unit and/or device position and/or step count and/or status of a medical condition and/or any other; this is because describing particular examples using just one word (e.g. velocity) clarifies things to the reader, but all possible combinations should be considered (although we do not write them all to avoid confusing the reader); by way of example without limitation, when we describe controlling the user's representation's velocity with a determined gait velocity of the user, the reader should consider as well all the following possibilities: controlling the user's representation's cadence with a determined gait cadence of the user; controlling the user's representation's stride length with a determined gait stride length of the user; controlling the user's representation's activity with a determined gait activity of the user; controlling the user's representation's calories burned per time unit with determined calories burned per time unit of the user; controlling the user's representation's device position with a determined device position of the user; controlling the user's representation's step count with a determined step count of the user; controlling the user's representation's status of a medical condition with a determined status of a medical condition of the user. Again, any variations and/or combinations thereof should also be considered.

In some embodiments, one or more attributes of one or more elements of the user's representation are controlled with the determined gait velocity (or any other characteristic e.g. cadence, and/or stride length, and/or activity, and/or device position, and/or calories burned per time unit, and/or status of a medical condition, and/or step count, etc.) in real time. For example, a user's representation may be composed of one or more elements such as right foot and/or left foot and/or right leg and/or left leg and/or right arm and/or left arm and/or right hand and/or left hand and/or shoulders and/or spine bone and/or hip bone and/or neck bone and/or neck and/or head and/or head bone and/or hair and/or eyes and/or mouth and/or eye brows and/or face, etc. Additional examples of elements of a user's representation and more can be found e.g. in en.wikibooks.org/wiki/Blender_3D:_Noob_to_Pro, cgi.tutsplus.com/tutorials/building-a-complete-human-character-rig-in-maya--cg-14575, gamedevelopment.tutsplus.com/tutorials/animating-a-makehuman-character-in-blender-part-one--cms-26489, en.blender.org/index.php/Doc:2.6/Tutorials/Your_First_Animation/2.Animation and/or any references and/or links within, all of which are herein incorporated by reference for all purposes. Each one of the elements of a user's representation may have one or more attributes, such as color, texture, etc.; for example, the face may have a skin color (e.g. black or white or any other) which may vary with the determined user's gait velocity/cadence/stride-length/calories per time unit/activity/device position/status of medical condition/etc. (e.g. if the determined velocity/cadence/stride-length/calories per time unit/activity/device position/status of medical condition/etc. is above 4 mph/2.2 Hz/0.85 m/250 Cal per hour/walking activity/pocket position/healthy/etc., the skin color of the face may be set to a reddish color to reflect exhaustion, or if the determined velocity/cadence/stride-length/calories per time unit/activity/device position/status of medical condition/etc. is below 1 mph/0.8 Hz/0.4 m/120 Cal per hour/walking activity/pocket position/unhealthy/etc. the skin color of the face may be set to a pale color to reflect weakness in the motion); well-known software packages such as Blender easily enable the setting of colors and/or textures and/or position and/or rotation and/or scaling and/or any other property of any element of a user's representation; by way of example without limitation, analogously to the way the skin color of the face was controlled in the example above, we can control the transform related attributes of e.g. the hip bone (or any other element) of the user's representation as e.g. shown in FIG. 12, and set/control them with or accordingly with the determined velocity and/or cadence and/or stride-length and/or activity and/or device position and/or calories burned per time unit and/or status of a medical condition and/or step count and/or any other and/or any variations and/or combinations thereof; for example, if the determined velocity/cadence/stride-length/calories per time unit/activity/device position/status of medical condition/etc. is/are above 4 mph/2.2 Hz/0.85 m/250 Cal per hour/walking activity/pocket position/healthy/etc. we can control the transform related attributes of the user's representation's hip (or of any movable part of the user's representation, e.g. right foot, left hand, head, etc.) by setting their values accordingly (e.g. changing said transform related attributes from one frame to the next as follows: e.g. from: Location x, y, z: 0.00000, −0.73849, −0.12757, Rotation (Quaternion w, x, y, z): 0.998, −0.000, −0.060, −0.010, Scale x, y, z: 1.000, 1.000, 1.000, to: Location x, y, z: 0.00000, −0.50799, −0.08775, Rotation (Quaternion w, x, y, z): 0.999, −0.000, −0.036, −0.006, Scale x, y, z: 1.000, 1.000, 1.000); and if the determined velocity/cadence/stride-length/calories per time unit/activity/device position/status of medical condition/etc. is/are below 1 mph/0.8 Hz/0.4 m/120 Cal per hour/walking activity/pocket position/unhealthy/etc. we can control the transform related attributes of the user's representation's hip (or of any movable part of the user's representation, e.g. right foot, left hand, head, etc.) by setting their values accordingly (e.g. changing said transform related attributes from one frame to the next as follows: e.g. from: Location x, y, z: 0.00000, −0.73849, −0.12757, Rotation (Quaternion w, x, y, z): 0.998, −0.000, −0.060, −0.010, Scale x, y, z: 1.000, 1.000, 1.000, to: Location x, y, z: 0.00000, −0.69140, −0.11943, Rotation (Quaternion w, x, y, z): 0.999, −0.000, −0.048, −0.008, Scale x, y, z: 1.000, 1.000, 1.000); other embodiments may use any other values and/or approaches and/or configurations and/or methods and/or any other and/or any variations and/or combinations thereof; further information can be found in "The Complete Guide to Blender Graphics, Second Edition: Computer Modeling and Animation" 2012 by John M. Blain, and/or in www.blender.org/support/tutorials/ all of which are herein incorporated by reference for all purposes. Additional examples of one or more attributes of elements of the user's representation which can be controlled with the determined user's gait velocity/cadence/stride-length/etc include: the texture of the skin of the neck, which can be modified to reflect sweat when the determined gait characteristics (again, velocity and/or cadence and/or stride-length and/or any other) indicate levels of high intensity in the gait activity.

In some embodiments, one or more attributes (e.g. color and/or texture) of three or more elements of the user's representation (e.g. right foot, left foot, right leg) may be controlled with the determined gait velocity in real time and independently; again, please consider that any other gait characteristic (e.g. cadence and/or stride length and/or activity and/or calories per time unit and/or device position and/or status of a medical condition and/or steps count and/or any other) can substitute the term velocity in these descriptions; for example, if the determined gait velocity is 4 mph, the right foot may be assigned a purple color, the left foot may be assigned a red color and the right leg may be assigned a texture showing sweat; if the determined gait velocity is 3 mph, the right foot may be assigned a red color, the left foot may be assigned an orange color and the right leg may be assigned a texture showing less sweat; if the determined gait velocity is 2 mph, the right foot may be assigned an orange color, the left foot may be assigned a yellow color and the right leg may be assigned a texture showing very little sweat; if the determined gait velocity is 1 mph, the right foot may be assigned a yellow color, the left foot may be assigned a white color and the right leg may be assigned a texture showing no sweat. It is interesting to note that in some embodiments, the controlled one or more attributes of said elements of the user's representation comprise one or more attributes different from properties of a transformation (change of location and/or rotation and/or scaling) affecting the whole user's representation equally; for example, the controlled attributes of the elements could be color, and/or texture, but not location and/or rotation and/or scaling coordinates/attributes when said location and/or rotation and/or scaling attributes are being modified only by a transformation that affects all the representation's elements equally (e.g. when we control the location and/or rotation and/or scaling coordinates/attributes (or any other(s) (e.g. velocity) derived from transform related attributes) of a user's representation as a whole, or of the user's representation's center of mass); for example, the control of the velocity of the user's representation as a whole (or the control of the velocity of the user's representation's center of mass) with the determined user's velocity does not satisfy the condition that one or more attributes of three or more elements of the user's representation are controlled independently. In some embodiments, one or more attributes of three or more elements of the user's representation are controlled with, and vary as a function of, the determined gait velocity (and/or cadence, and/or stride length and/or calories burned per time unit, and/or device position, and/or activity, and/or status of a medical condition, and/or balance, and/or steps, etc.) in real time and independently. By way of example without limitation, if we consider the right foot as an element, and the maximum displacement in the horizontal direction of said right foot as an attribute (e.g. said attribute may indicate the maximum advancement or maximum displacement of the right foot in the horizontal direction at every footstep), said attribute may vary in real time as a function of the determined gait velocity (e.g. maximum displacement may be proportional to 10 times the determined velocity, or vary with any other function in terms of the determined velocity); and in some embodiments, this variation may be different and/or independent for attributes of different elements of the user's representation (e.g. the maximum displacement in the horizontal direction in the left foot may vary with velocity differently than in the right foot (e.g. maximum displacement of the left foot may be proportional to 11 times the determined velocity); and the maximum displacement of the left hand may be proportional to 7 times the determined velocity. In some embodiments, the described variation of said attribute(s) may occur while the user performs a same type of activity. For example, the maximum displacement of the right foot may vary proportionally with the determined velocity while the user performs a walking activity (e.g. maximum displacement in centimeters=velocity in mph*10); or the color of the right foot may be assigned different values for each one of at least four different values of the determined velocity while the user performs a walking activity (e.g. said color is set as purple, red, orange, and yellow when the determined user's walking velocity is, respectively, 4 mph, 3 mph, 2 mph and 1 mph); or the color of the right foot may be assigned different values for each one of at least four different values of the determined velocity while the user performs a running activity (e.g. said color is set as black, blue, magenta, and pink when the determined user's running velocity is, respectively, 8 mph, 7 mph, 6 mph and 5 mph).

In some embodiments, the user's representation shows feet landing on (or touching) a ground (or a horizontal plane that in some embodiments may represent any type of ground, including an invisible ground in some examples of virtual environments) in synchronism with the user's feet landing on (or touching) a ground (or stepping), and this may happen in some embodiments while the user's representation (or one or more attributes (or one or more attributes of one or more elements) of the user's representation) is/are being controlled in real time with the determined user's gait velocity and/or cadence and/or stride-length and/or activity, and/or calories burned per time unit, and/or device position, and/or status of a medical condition, and/or balance, and/or steps, etc. An example of embodiment describing a user's representation showing feet landing on (or touching) a ground (or stepping) in synchronism with the user's feet landing on (or touching) a ground (or stepping) can be found at least in application U.S. 62/750,292 entitled "Gait analysis applied for control", by David Martin, filed on Oct. 25, 2018, herein incorporated by reference for all purposes. For example, some embodiments may detect the time instants at which the mobile or wearable device user's feet land on the ground through the analysis of a motion sensor (e.g. embedded within the mobile or wearable device) signal (e.g. detecting peaks of maximum amplitude of said motion sensor signal, where the motion sensor may be an accelerometer embedded within the device), and display a frame by frame animation (e.g. using frames 0 to 25 from e.g. FIG. 9A or FIG. 9B or any other) assigning the frame at which the user's representation shows a foot landing on the ground (e.g. frame 0 and frame 13), to the time instants at which the user's foot touching the ground is detected, thus achieving a synchronism between the user's representation showing a foot landing on the ground and the user's foot landing on the ground. For example, at the time a new step of the user is detected (in other words, a user's foot landing on the ground is detected), the frame by frame animation may show frame 0 (e.g. showing a user's representation's foot landing on the ground); in subsequent time instants, the following frames are displayed (e.g. respecting time intervals between frames to achieve correspondence between the period of the animation cycle and the period of the user; for instance, if the user's period is 0.5 seconds, which can be determined as the inverse of a determined user's gait cadence (e.g. 2 Hz), and the frame by frame animation has 26 frames (0 to 25) the time interval between frames may be approximately 0.038 seconds=1 second of a whole animation cycle (2 periods)/26 frames); e.g. frame 1 is displayed 0.038 seconds after frame 0 and so on; when a new step is detected, frame 13 should be displayed to maintain synchronism between the user's detected steps and the user's representation's steps; if the user kept cadence constant, we should be normally displaying frame 13 at the time the new user's step is detected; however, if the user changes cadence, we may find ourselves displaying a frame different from frame 13 (e.g. we might be displaying frame 11), so we should display frame 13 instead of frame 11 in order to maintain the synchronism; the process is repeated when the next step of the user is detected, in which case we should display frame 0 again and so on repeating the cycle.

Other embodiments may use any other methods and/or any variations and/or combinations thereof. In some embodiments, the synchronism may be achieved with a latency equal to or below a fraction of one step period (e.g. updating the detection of the time instants at which the user's feet land on the ground with a frequency greater than the user's step frequency, or in other words, fast enough to be able to assign the frame at which the user's representation (or animation) lands on the ground, to the time instant of the detection of the user's foot landing on the ground, before a fraction of one step period has elapsed). Some embodiments may select a time interval (e.g. 0.125 seconds, or 0.1 seconds, or 0.05 seconds, or any other value below a threshold of e.g. 0.125 seconds (and obviously larger than 0 to be physically possible)) for updating the detection of the time instants at which the user's feet land on the ground, regardless of the user's step period, but small enough to be a fraction of a user's step period (e.g. considering normal gait frequencies below 6 Hz, any time interval smaller than e.g. $\frac{1}{6}$=0.166 seconds would be a fraction of a user's step period); consequently, in some embodiments, the synchronism may be achieved with a latency equal to or below a threshold amount of time, where said threshold may be any number equal to or below 0.125 seconds. The referred application U.S. 62/750,292 further describes embodiments where the synchronism latency is equal to or below a fraction of one step period. Other embodiments may use any variations and/or combinations thereof. And in some embodiments, all this may happen while the user's representation (or one or more attributes of the user's representation) is controlled in real time with a determined user's gait velocity and/or cadence and/or stride length and/or activity and/or step count and/or calories burned per time unit, and/or device position, and/or status of a medical condition, and/or balance, and/or steps, and/or any other and/or any variations and/or combinations thereof.

In some embodiments, a gait cadence of the user's representation is controlled in real time with a determined gait cadence of the user, as described at least in paragraph [0117] of application U.S. 62/651,409 entitled "Control Strategies For Mobile Using Gait Analysis", by David Martin, filed on Apr. 2, 2018, herein incorporated by reference for all purposes. For example, as shown in FIG. 13 and FIG. 11A, the user's determined cadence may control the user's representation's cadence in real time and with an update frequency larger than the user's step frequency: the variable completeAnimationPeriod is controlled by the determined (in real time and with an update frequency larger than the user's step frequency) user's cadence, and it controls the value of the variable currentFrame, which is responsible for how fast a whole gait cycle of the user's representation is displayed, or how long it will take to display a whole user's representation's gait cycle (e.g. doDraw method in FIG. 11B is called with regular frequency of, for instance, 60 Hz, and this method calls the manageCurrentFrame method (FIG. 11A) to control which frame to be rendered on the device screen (currentFrame); as shown in FIG. 11A, if completeAnimationPeriod is large, it will take long time for the value of currentFrame to change, while if completeAnimationPeriod is short, it will take short time for the value of currentFrame to change; thus we are controlling the time it takes for currentFrame to change, or the time it takes for frames to change, or the time it takes for 26 frames to be changed, or the time it takes for a whole gait cycle to complete, or the time period of the gait, or the cadence or frequency (=1/period) of the gait of the user's representation on the device screen). At the same time that the user's determined cadence controls the user's representation's cadence, in the same conditions it may also control other attributes in the user's representation. Additional details are included at least in the referred application U.S. 62/651,409. And in some embodiments, all this may happen while the user's representation (or one or more attributes of the user's representation) is controlled in real time with a determined user's gait velocity and/or cadence and/or stride length and/or activity and/or step count and/or any other and/or any variations and/or combinations thereof. And in particular embodiments, the user's representation may additionally show feet landing on a ground in synchronism with the user's feet landing on a ground, and/or a head moving in synchronism with the user's feet landing on a ground (or stepping or footsteps) and/or shoulders moving in synchronism with the user's footsteps, and/or a back moving in synchronism with the user's footsteps, and/or a hip moving in synchronism with the user's footsteps, and/or a hair moving in synchronism with the user's footsteps, and/or any others and/or any variations and/or combinations thereof.

By way of example without limitation, some embodiments may synchronize the user's representation with the determined user's gait cadence (e.g. controlling in real time the user's representation's gait cadence with the determined user's gait cadence, and keeping both cadences constantly equal, for instance updating both cadences with a frequency greater than the user's step frequency, in such a way that the user's representation moves in synchronism with the determined user's gait cadence), and at the same time, leverage a threshold number of different animations for a same type of gait activity. For example, while the user performs a walking activity, some embodiments may use four different animations representing the walking activity, but with different attributes in the user's representation. For instance, FIGS. 9A, 9B, 9C and 9D show four different images/frames strip files from which four different animations may be obtained, all for the same activity (walking), but with different attributes in the user's representation (e.g. different stride length, different angles in the elbows, different extensions in the arms, different angles in the head, different angles in the shoulders, different angles in the back, different angles in the hip, etc.). For example, while the user performs a running activity, some embodiments may use two different animations representing the running activity, but with different attributes in the user's representation. For instance, FIGS. 9E, and 9F show two different images/frames strip files from which two different animations may be obtained, all for the same activity (running), but with different attributes in the user's representation (e.g. different stride length, different angles in the elbows, different extensions in the arms, different angles in the head, different angles in the shoulders, different angles in the back, different angles in the hip, different bouncing movement of the hair, etc.). Other embodiments may use any other approaches and/or any variations and/or combinations thereof. It is interesting to note that in some embodiments the threshold number of different animations for a same activity can be any integer value, including any greater than two. It is also interesting to note that in some embodiments the different animations may be selected in terms of factors comprising the determined user's gait cadence and/or velocity and/or stride length and/or calories burned per time unit and/or device position and/or step count and/or status of a medical condition and/or any other and/or any variations and/or combinations thereof. For example, the animation corresponding to FIG. 9A may be selected for values of determined user's gait cadence below 1 Hz, while the animation corresponding to FIG. 9B may be selected for values of determined user's gait cadence equal to or greater than 1 Hz but below 1.5 Hz, while the animation corresponding to FIG. 9C may be selected for values of determined user's gait cadence equal to or greater than 1.5 Hz but below 2 Hz, while the animation corresponding to FIG. 9D may be selected for values of determined user's gait cadence equal to or greater than 2 Hz, while other embodiments may use any other criteria. For example, the animation corresponding to FIG. 9A may be selected for values of determined user's stride-length below 60 cm, while the animation corresponding to FIG. 9B may be selected for values of determined user's stride-length equal to or greater than 60 cm but below 90 cm, while the animation corresponding to FIG. 9C may be selected for values of determined user's stride-length equal to or greater than 90 cm but below 140 cm, while the animation corresponding to FIG. 9D may be selected for values of determined user's stride-length equal to or greater than 140 cm, while other embodiments may use any other criteria. For example, the animation corresponding to FIG. 9A may be selected for values of determined user's gait velocity below 1 mph while the animation corresponding to FIG. 9B may be selected for values of determined user's gait velocity equal to or greater than 1 mph but below 2 mph, while the animation corresponding to FIG. 9C may be selected for values of determined user's gait velocity equal to or greater than 2 mph but below 3 mph, while the animation corresponding to FIG. 9D may be selected for values of determined user's gait velocity equal to or greater than 3 mph, while other embodiments may use any other criteria. All these examples can be extended for different attributes (e.g. calories burned per time unit and/or device position and/or step count and/or status of a medical condition and/or any other and/or any variations and/or combinations thereof).

Some embodiments may also control a stride length of the user's representation in real time with a determined stride length of the user, as described at least in paragraph [0116] of application U.S. 62/651,409 entitled "Control Strategies For Mobile Using Gait Analysis", by David Martin, filed on Apr. 2, 2018, herein incorporated by reference for all purposes. For example, the user's determined stride length may control the stride length of the user's representation being displayed on the device screen, and this may be achieved in some embodiments by controlling, leveraging the value of determined user's stride length, the selection of an appropriate images strip file where the user's representation has the appropriate value of stride length (e.g. in pseudocode: if (determined_stride_length==value1) {then, images_strip_file="file1.png";} else if (determined_stride_length== value2) {then, images_strip_file="file2.png";} . . . and so on). Additional details can be found at least in paragraphs [0112-0116] of the referred application U.S. 62/651,409. And in some embodiments, all this may happen while the user's representation (or one or more attributes of the user's representation) is controlled in real time with a determined user's gait velocity and/or cadence and/or stride length and/or activity and/or step count and/or any other and/or any variations and/or combinations thereof.

Similar reasoning can be extended to some embodiments where the user's representation's calories burned per time unit are controlled in real time with the determined calories burned per time unit of the user, as described at least in paragraph [0120] of application U.S. 62/651,409 entitled "Control Strategies For Mobile Using Gait Analysis", by David Martin, filed on Apr. 2, 2018, herein incorporated by reference for all purposes. Similar reasoning can be extended to some embodiments where the user's representation's device position is controlled in real time with the determined user's device position, as described at least in paragraph [0121] of the referred application U.S. 62/651,409. It is also interesting to note that in some embodiments, the referred user's device position may be determined in real time leveraging a determined gait cadence of the user, as described at least in paragraph [0126] of the referred application U.S. 62/651,409. Similar reasoning can be extended to some embodiments where the user's representation's step count is controlled in real time with the determined step count of the user, as described at least in paragraph [0105] of application U.S. 62/750,292 entitled "Gait Analysis applied for control", by David Martin, filed on Oct. 25, 2018, herein incorporated by reference for all purposes. It is interesting to note that in some embodiments, the user's step count is determined in real time leveraging a determined gait cadence of the user, as described at least in the referred application U.S. 62/750,292. Similar reasoning can be extended to some embodiments where the user's representation's activity is controlled in real time with the determined user's activity, as described at least in paragraph [0118] of the referred application U.S. 62/651,409. It is also interesting to note that in some embodiments, the referred user's activity may be determined in real time leveraging a determined gait cadence of the user, as described at least in paragraph [0126] of the referred application U.S. 62/651,409. And in some embodiments, all this may happen while the user's representation (or one or more attributes of the user's representation) is controlled in real time with a determined user's gait velocity and/or cadence and/or stride length and/or activity and/or step count and/or any other and/or any variations and/or combinations thereof.

Similar reasoning can be extended to some embodiments where the user's representation's velocity is controlled in real time with the determined gait velocity of the user, as described at least in application U.S. Ser. No. 14/922,174 entitled "Application of Gait Characteristics For Mobile", by David Martin, filed on Oct. 15, 2015, herein incorporated by reference for all purposes, and in paragraph [0119] of application U.S. 62/651,409 entitled "Control Strategies For Mobile Using Gait Analysis", by David Martin, filed on Apr. 2, 2018, herein incorporated by reference for all purposes. And in some particular embodiments, the controlling of the user's representation's velocity is performed with an update frequency chosen in terms of an update frequency of the determining of the user's gait velocity. For example, the update frequency of the controlling of the user's representation's velocity may be equal to the update frequency of the determining of the user's gait velocity, as described at least in the referred application U.S. Ser. No. 14/922,174, while other embodiments may choose to e.g. update the controlling of the user's representation's velocity at half (or at double, or with any other type of relationship) the update frequency of the determining of the user's gait velocity. It is interesting to note that in some embodiments the user's representation represents a human being, and an aspect of an application in the user's device (e.g. the activity of the user's representation being displayed in the user's device within an application) is controlled with a determined gait activity of the user in real time. And in some embodiments, the controlling of the user's representation's velocity with the determined gait velocity is enabled after a gait activity of the user has been recognized (e.g. we may be continuously determining the user's gait activity, and for instance, if the user's device is still, no gait activity such as walking, jogging, running, etc. is recognized, so we may disable any controlling; however, if the user starts moving, as soon as we recognize/determine the user's activity, e.g. walking, we may enable the controlling of the user's representation's velocity with a determined user's gait velocity), as described at least in the referred application U.S. Ser. No. 14/922,174.

It is interesting to note, as already mentioned, that some embodiments may substitute any of the used terms (e.g. activity and/or velocity and/or cadence and/or stride-length and/or calories burned per time unit and/or step count and/or status of a medical condition and/or device position and/or any other) by each and every one of them and/or any variations and/or combinations thereof; by way of example without limitation, throughout any descriptions in this specification or any of the referred applications, the term velocity may be substituted in some embodiments by the term cadence and/or stride-length and/or activity and/or calories burned per time unit and/or step count and/or status of a medical condition and/or device position and/or any other and/or any variations and/or combinations thereof. In this sense, an aspect of an application in the user's device (e.g. the gait cadence of the user's representation, which may be displayed on the user's device screen as part of an application) may be controlled in some embodiments with a determined gait cadence of the user; and in some embodiments, all this may happen while the user's representation (or one or more attributes of the user's representation) is controlled in real time with a determined user's gait velocity and/or cadence and/or stride length and/or activity and/or step count and/or any other and/or any variations and/or combinations thereof. At the same time, in some embodiments, the user's representation can interact with elements in a virtual environment, as described at least in the referred applications U.S. Ser. No. 14/922,174 and U.S. 62/651,409, and in some embodiments the user also participates in a networking environment with other users, and shares the same type of representation with the other users also represented in the virtual environment, wherein the virtual environment further includes one or more dashboard elements indicating velocity, and wherein the user's representation's gait activity is controlled in real time with the determined gait activity, and wherein the controlling of the user's representation's velocity with the determined gait velocity is enabled after a gait activity of the user has been recognized. In other embodiments, the user participates in a networking environment with other users, and one or more users also represented in the virtual environment, are represented with a different type of representation (e.g. human being vs means of transportation vs non-human being and/or young human being vs old human being and/or human being belonging to one team vs human being belonging to a different team (e.g. dressed in a different way) and/or any others and/or any variations and/or combinations thereof). And in some embodiments, the virtual environment further includes one or more dashboard elements indicating velocity (e.g. users' representations' velocities). In other embodiments, the user's representation may represent a means of transportation (e.g. a car), and the user's representation can interact with elements in a virtual environment, wherein the user may participate in a networking environment with other users, and share the same type of representation with the other users also represented in the virtual environment, wherein the virtual environment may further include one or more dashboard elements indicating velocity (e.g. the user's representations' velocities), and wherein an aspect of an application in the user's device (e.g. the enabling of the controlling with the determined user's velocity) may be controlled with a determined gait activity of the user, and wherein the controlling of the user's representation's velocity with the determined gait velocity may be enabled after a gait activity of the user has been recognized, and wherein the determining of the user's gait velocity may be performed within a thread of an application separate from a main thread of the application.

It is interesting to note that in some embodiments, by way of example without limitation, any of the cases/examples described for the update frequency of the determining of the gait characteristic may be used in combination (e.g. simultaneously or in any other way) with any of the cases/examples described for the update frequency of the controlling of an aspect and/or one or more attributes of the user's representation with the determined gait characteristic. The same applies to any of the cases/examples described regarding the thread(s) in which any of the determining and/or controlling is performed. And again, any of the embodiments and/or any of their variations and/or combinations can use interchangeably or in any other way any of the gait characteristics (e.g. gait velocity and/or cadence and/or stride-length and/or activity and/or calories burned per time unit and/or step count and/or device position and/or status of a medical condition and/or any other and/or any variations and/or combinations thereof).

By way of example without limitation, some embodiments may be controlling a velocity of the user's representation with a determined user's gait velocity in real time, and the determining of the user's gait velocity may be performed within a main thread of an application, and the controlling of the user's representation's velocity may be performed with an update frequency chosen in terms of an update frequency of the determining of the user's gait velocity, and the controlling of the user's representation's velocity may be performed within a main thread of an application, and the update frequency of the controlling of the user's representation's velocity may be equal to the update frequency of the determining of the user's gait velocity and/or the controlling of the user's representation's velocity may performed within a thread of an application separate from a main thread of the application in other circumstances. In other examples of embodiments, the controlling of the user's representation's velocity may be performed within the main thread of the application, and the controlling of the user's representation's velocity may be performed with an update frequency chosen in terms of an update frequency of the determining of the user's gait velocity, and the update frequency of the controlling of the user's representation's velocity may be equal to the update frequency of the determining of the user's gait velocity. In other examples of embodiments, the controlling of the user's representation's velocity may be performed with an update frequency, which may be a constant value, while a sampling frequency of an accelerometer of the user's device is variable, and the accelerometer of the user's device may be leveraged in the determining of the user's gait velocity; still in other examples of embodiments, the controlling of the user's representation's velocity may be performed with an update frequency, which may be a constant value greater than an upper edge of a frequency band of the user's gait activity and lower than a sampling frequency of an accelerometer of the user's device, and the accelerometer of the user's device may be leveraged in the determining of the user's gait velocity; and/or the controlling of the user's representation's velocity may be performed with an update frequency, which may be a constant value greater than an upper edge of a frequency band of the user's gait activity and lower than a sampling frequency of an accelerometer of the user's device, while the sampling frequency of the accelerometer of the user's device is variable, and the accelerometer of the user's device may be leveraged in the determining of the user's gait velocity; and/or the controlling of the user's representation's velocity may be performed with an update frequency different from the application's frame (or screen) refresh rate; and/or the controlling of the user's representation's velocity may be performed within a thread of the application separate from the main thread of the application; still in other examples of embodiments, the determining of the user's gait velocity may be performed within a thread of an application separate from a main thread of the application, and the controlling of the user's representation's velocity may be performed within a thread of the application separate from the main thread of the application or the controlling of the user's representation's velocity may be performed within the main thread of the application; still in other examples of embodiments, the controlling may comprise controlling one or more attributes (e.g. color and texture of the face skin) of the user's representation with the determined gait velocity in real time, and wherein the one or more attributes of the user's representation may comprise one or more attributes different from a velocity (e.g. color and texture of the face skin) and/or wherein the one or more attributes of the user's representation may comprise one or more attributes different from properties of a transformation of the whole user's representation, or in other words, wherein said attributes are not properties (e.g. position/location xyz, rotation xyzw, scale xyz) of a transformation of the whole user's representation (e.g. said attributes may be properties of a transform affecting the user's representation's arm's right elbow angle and/or left elbow angle and/or color of face skin and/or texture of neck skin and/or hair bouncing and/or stride length and/or any other and/or any variations and/or combinations thereof); or the attributes controlled with the determined user's gait velocity may be different from translations (or location/position components x,y,z) and/or rotations (e.g. x,y,z,w) and/or scales (e.g. x,y,z); for instance, in the case of e.g. the user's representation being a means of transportation (e.g. a car), the controlled attributes can be: smoke amount coming out of the exhaustion tube, sparks appearing on the wheels, speed of rotation of wheels, velocity indication on the dashboards (both dashboard and user's representation may be displayed simultaneously), color of car, etc.; other embodiments may determine the user's gait velocity with an update frequency larger than the user's step frequency and control an aspect of an application with the determined user's velocity and with said update frequency; and within this last case, in some embodiments, said update frequency may be a constant and/or may be chosen in terms of the user's step frequency, and/or may be lower than an accelerometer sampling rate; and in some embodiments, an aspect of the application may be controlled with the recognition that the user's gait activity has stopped (e.g. the screen brightness can be reduced after the stop of the user's activity has been recognized); in other embodiments, a user's representation may not be part of a virtual environment, but instead be displayed independently or without any relationship to a virtual environment; other embodiments using update frequencies (for determining the user's gait velocity/cadence/stride-length and/or for controlling with said velocity/cadence/stride-length) chosen in terms of the user's step frequency (e.g. greater than the user's step frequency), may not need to monitor the user's step frequency at all (e.g. if an update frequency is set as a constant larger than the user's step frequency, and said constant is e.g. 15 Hz or above, there is no need monitor the user's step frequency, because it is not going to reach 15 Hz, so an update frequency of 15 Hz which is constant does not need to monitor the user's step frequency to fulfil the requirement that it is above the user's step frequency, and this may apply to any constant value above the upper edge of the gait frequency band (e.g. approximately 2.5 Hz for walking, or approximately 7 Hz for running, wherein said upper edge may be determined empirically/experimentally in some embodiments)); other embodiments may determine any gait parameter (e.g. velocity) without relying on signals external to the user's device (e.g. leveraging only an accelerometer, without relying on satellite signals and/or infrared signals and/or any other type of external signals); still in other examples of embodiments, any other attributes and/or elements and/or substitutions (e.g. substituting velocity by cadence and/or stride-length and/or activity and/or calories burned per time unit and/or device position and/or step count and/or status of a medical condition and/or any other and/or any variations and/or combinations thereof) and/or procedures and/or methods and any variations and/or combinations thereof may also be possible.

In the same sense, some examples of embodiments are provided next, emphasizing on the idea that the term(s) "velocity", or "gait velocity", or "gait characteristic(s)" can be substituted throughout all this specification and throughout all the references incorporated in this specification, by velocity and/or cadence and/or stride-length and/or activity and/or calories burned per time unit and/or device position and/or step count and/or status of a medical condition and/or any other and/or any variations and/or combinations thereof; in fact, an example of embodiment described with the help of the code of FIG. 13 shows that we can obtain/determine simultaneously a variety of the user's gait characteristics/parameters; for example FIG. 13 shows that we can directly obtain velocity, calories burned per time unit, cadence, and activity from the "determine_gait_parameters" method, while in other embodiments we can directly obtain/determine from said method (or an adaptation/variation of said method) additional gait characteristics/parameters such as stride or step length (e.g. dividing velocity by cadence) and device position (e.g. using any machine learning technique leveraging any training set gathered in any way and using the gait characteristics we have already determined as features) and status of a medical condition (e.g. using any machine learning technique leveraging any training set gathered in any way and using the gait characteristics we have already determined as features) and any other using any of the mentioned techniques/approaches/methods and/or any others and/or any variations and/or combinations thereof; and for clarity purposes, in the examples of embodiments that follow (the same is applicable to any others as mentioned above), we will use the term "gait characteristic(s)", knowing that it can refer to any and/or all and/or any combinations of any of the mentioned gait characteristics/parameters.

All particularizations made in any of the referred applications (including application Ser. No. 16/275,323 and references within) using any gait attribute (e.g. velocity) are extended in this application to gait cadence (and/or any other attribute). In other words, any example and/or embodiment and/or any other(s) of any said applications are included hereby, substituting the terms "velocity" or "gait velocity" or "gait attribute" or similar, by the term "gait cadence". In other words, all examples and/or embodiments and/or any other(s) of any said applications are hereby incorporated by reference, substituting the terms "velocity" or "gait velocity" or "gait attribute" or similar, by the term "gait cadence".

Some embodiments may use methodologies to help determine the correct value of cadence in conditions in which traditional approaches may be prone to errors; by way of example without limitation, some embodiments may use a method (and/or system and/or non-transitory processor-readable medium) to help in the determination of cadence, by supporting (or nor supporting) a suggested value of cadence. It should be noted that, in some embodiments, this process of "supporting (or not supporting)" a suggested value of cadence, that will be described in these paragraphs, requires a subsequent decision process that will take into consideration this "support (or not support)", together with other factors and/or suggestions and/or conditions in order to make the final decision of determining a value of cadence. By way of example without limitation, some embodiments may determine the value of cadence as the suggested value of cadence if the support described in these paragraphs is positive; other embodiments may determine the value of cadence as the suggested value of cadence if the support described in these paragraphs is positive and other conditions (e.g. if the dominant frequency from a Fourier transformation of the motion sensor signal vector module matches the suggested value of cadence, and/or any other conditions) are also affirmative; while other embodiments may determine the value of cadence by assigning a previously determined value of cadence if the support described in these paragraphs is negative; and other embodiments may determine the value of cadence by assigning a previously determined value of cadence if the support described in these paragraphs is positive but other conditions (e.g. if the dominant frequency from a Fourier transformation of the motion sensor signal vector module matches the suggested value of cadence, and/or any other conditions) are negative; other embodiments may use any other techniques and/or approaches and/or conditions and/or any others and/or any variations and/or combinations thereof. Consequently, in some embodiments, the process described in these paragraphs regarding "supporting (or not supporting)" a suggested value of cadence can not be interpreted as a process of "accepting or rejecting" (or "approving or overriding" or similar) a determined value of cadence.

By way of example without limitation, said suggested value to be supported may be a low cadence (e.g. 0.55 Hz or approximately 0.5 Hz or 0.7 Hz or 0.4 Hz, or any other), although other embodiments may use different values of cadence (e.g. 1 Hz or approximately 0.9 Hz or 1.2 Hz or 1.4 Hz, or any other, e.g. 1.5 Hz or approximately 1.6 Hz or 1.7 Hz or 1.4 Hz, or any other, e.g. 1.8 Hz or approximately 1.9 Hz or 1.75 Hz or 1.95 Hz, or any other). Next, for clarity purposes, an example will be given of an embodiment of a method wherein the determination of a value of cadence comprises supporting a suggested value of cadence; for clarity purposes, this example of embodiment will focus on supporting a low value of cadence (e.g. 0.5 Hz), but other embodiments can focus on different values of cadence (e.g. values expressed above and/or any other values (e.g. 1.1 Hz or 1.3 Hz or 1.6 Hz or 1.85 Hz) and/or any other and/or any variations thereof). For example, if any of the techniques mentioned in this application, or any other techniques and/or methodologies, suggest a value of cadence of 0.5 Hz, we may use a method (and/or system and/or non-transitory processor-readable medium) to support said low value of cadence (e.g. 0.5 Hz). It is interesting to note that in some embodiments, the supporting of a value of cadence can be done automatically within the device and by the device (without any manual or any other type of intervention from the user to support a value); for example, the support of a value of cadence can done in some embodiments automatically and algorithmically within microseconds (e.g. the time it takes for a processor to execute the steps that will be described next), and said support can be implemented in some embodiments for every suggested value of cadence, or only for some range of values of cadence (e.g. from 0.3 Hz to 0.7 Hz, or from 0.8 Hz to 1.25 Hz, or any other values and/or ranges and/or any combinations and/or modifications thereof), or only for some values according to any selection criteria (e.g. if the suggested value of cadence implies a relative change of over 25% with respect to a previous determined value of cadence (e.g. the immediately previously determined value of cadence is 1 Hz, and the currently suggested value of cadence is 0.5 Hz)). The idea is to enable a second decision opportunity for a value of cadence (useful for example for cases where traditional approaches are prone to errors) in order to help in a determination of cadence with high accuracy. Some embodiments may use any other approaches (including opposite of what has been previously described (e.g. allowing manual intervention of the user to support a value, etc.) and/or any other criteria and/or techniques and/or methods and/or any other and/or any variations and/or combinations thereof). By way of example without limitation, the method in an example of an embodiment to support a suggested value of cadence, may comprise the following steps:

Step 1) Determine (or find or identify) the axis of the motion sensor (e.g. a triaxial accelerometer) with the highest mean in absolute value. Some embodiments may determine the mean values of the 3 axes (mean of x axis, mean of y axis, mean of z axis), and determine their absolute values; for example, (we will be using simplistic schematic pseudocode for clarity purposes to help readers easily understand the different steps) mean_x_axis=abs(mean(x)); meany_axis=abs(mean(y)); mean_z_axis=abs(mean(z)). After comparing the 3 determined absolute values, we can identify the order of axis with highest mean: e.g. highestMeanOrder= argmax ([mean_x_axis, mean_y_axis, mean_z_axis]). This determines (identifies the order as 0, 1, or 2) the axis of the motion sensor (e.g. a triaxial accelerometer) with the highest mean in absolute value.

Step 2) Determine (or find or identify) the axes of the motion sensor (e.g. a triaxial accelerometer) with the lowest mean in absolute value. This can be done leveraging the result from the previous step; for example: firstlowMeanOrder=(highestMeanOrder+1) % 3; for clarity purposes, "%" represents modulus operation, well known in the art (please see well known programming references such as "Learning python" by Mark Lutz, ISBN-13: 978-1449355739, or "Python cookbook" by David Beazkey, ISBN-13: 978-1449340377, or "Java programming" by Joyce Farrell, ISBN-13: 978-1285856919 and/or any references within for further details on well known concepts and terms and/or others). The order of the other low mean axis can be computed as: secondlowMeanOrder=3−(highestMeanOrder+firstlowMeanOrder). So we have identified the axes of the motion sensor (e.g. a triaxial accelerometer) with the lowest mean in absolute value (firstlowMeanOrder, secondlowMeanOrder), and consequently, we have identified (e.g. as 0, 1, 2) the 3 axes of the motion sensor (e.g. a triaxial accelerometer).

Step 3) Determine the order of the low mean axis (e.g. either firstlowMeanOrder, or secondlowMeanOrder) with larger value of an average of the frequencies of maximum amplitude computed for said axis using a Fourier transformation (e.g. computing the Fourier transformation of the x (or y or z) axis of the accelerometer over a time window of e.g past 4 seconds, or past 10 seconds, or past 20 seconds, or any other amount of time), wherein said average has been computed over a time window (e.g past 8 seconds, or past 20 seconds, or past 40 seconds, or any other amount of time) leveraging computed values of the frequencies of maximum amplitude computed for said axis using a Fourier transformation. For example, the referred average of the frequencies of maximum amplitude computed for said axis using a Fourier transformation can be computed in some embodiments as follows: x_fftPeak1_avg=weight_for_previous_value*x_fftPeak1_avg+weight_for_new_value*x_fftPeak1. For simplicity and clarity, the names of the variables in the pseudocode refer to the frequency of maximum amplitude computed for said axis (e.g. x, or y or z) using a Fourier transformation as fftPeak1 (the frequency corresponding to the peak with maximum amplitude (peak1) of the Fourier transform of the referred axis); consequently, x_fftPeak1_avg represents the average of the computed fftPeak1 values over time for the x axis. Again, this is a very simplistic example for clarity purposes, and other embodiments may use more complex methodologies to deliver the different results to be computed. Following with these examples, the average for the y axis can be computed as y_fftPeak1_avg=weight_for_previous_value*y_fftPeak1_avg+weight_for_new_value*y_fftPeak1; and for the z axis: z_fftPeak1_avg=weight_for_previous_value*z_fftPeak1_avg+weight_for_new_value*z_fftPeak1. Next we can create an array holding said averages: array([x_fftPeak1_avg, y_fftPeak1_avg, z_fftPeak1_avg]), and use said array to determine the averages of the fftPeak1 of the low mean axes: firstlowMean_fftPeak1_avg=array ([x_fftPeak1_avg, y_fftPeak1_avg, z_fftPeak1_avg]) [firstlowMeanOrder]; secondlowMean_fftPeak1_avg=array ([x_fftPeak1_avg, y_fftPeak1_avg, z_fftPeak1_avg]) [secondlowMeanOrder]; next we can compute the order of the low mean axis with larger average of fftPeak1 (the frequency corresponding to the maximum amplitude computed for said axis (e.g. x, or y or z) using a Fourier transformation) as follows: orderOfLowMeanWithLarger_fftPeak1_avg=array([firstlowMeanOrder, secondlowMeanOrder]) [int(firstlowMean_fftPeak1_avg<secondlowMean_fftPeak1_avg)]; again, other embodiments may use different approaches as previously stated.

Step 4) Check if, in the axis identified in step 3, a frequency corresponding to a peak with maximum amplitude in a Fourier transformation (fftPeak1), matches the suggested value of cadence (frequency) we want to support. For this, we can first determine the frequency corresponding to the peak with maximum amplitude in a Fourier transformation computed for said axis (e.g. using x, or y or z (time domain data of each of the accelerometer axes) depending on which axis has been identified, and applying a Fourier transformation, from where we can identify the peak of maximum (or largest) amplitude); we can call that frequency fftPeak1_of_LowMeanWithLarger_fftPeak1_avg. For example, if the suggested cadence is 0.5 Hz, we check if fftPeak1_of_LowMeanWithLarger_fftPeak1_avg is 0.5 Hz (some embodiments may use tolerance margins, e.g. allowing up to a threshold (e.g. 25% or 35% or any other threshold) of error, so that a value of fftPeak1_of_LowMeanWithLarger_fftPeak1_avg of e.g. 0.4 Hz or 0.6 Hz or any value in between, would still satisfy the condition). Consequently, Step 4 comprises: checking if, in an axis of an accelerometer, said axis being identified leveraging a comparison of absolute values of mean values, a frequency corresponding to a peak with a maximum amplitude in a Fourier transformation, matches the suggested value of cadence. In other words, Step 4 comprises: determining a frequency corresponding to a peak with a maximum amplitude in a Fourier transformation of an axis of an accelerometer, said axis being identified leveraging a comparison of absolute values of mean values; and checking if, the determined frequency corresponding to the peak in the Fourier transformation, matches the suggested value.

Step 5) if the condition in Step 4 has been satisfied, we next check if an index of a secondary maximum with a largest amplitude in the signal resulting from applying an autocorrelation of the motion sensor signal (in the time domain) corresponding to the axis identified in step 3 (e.g. autocorrelation of x axis of accelerometer in time domain, if the identified axis in step 3 is x axis), satisfies the condition of being within an expected range in agreement with the suggested value of cadence (please note that said secondary maximum with largest amplitude in the signal resulting from applying an autocorrelation is different from the central maximum of the autocorrelation). For example, if the suggested value of cadence is 0.5 Hz, we would expect said secondary maximum with largest amplitude in the autocorrelation to be at a distance from the central maximum of the autocorrelation that would correspond with a frequency of 0.5 Hz. Please remember that the inverse of the time distance between the central maximum of the autocorrelation signal and the largest secondary maximum of the autocorrelation signal, represents an indication of the fundamental frequency or cadence of the original motion sensor signal. To check the condition of this step 5, we can follow the next process: substep A) determine a time domain window of the accelerometer's identified axis in step 3 (in other words, determine time domain data of the accelerometer corresponding to the axis identified in step 3); this can be done using the time domain data provided by the accelerometer; for example calling said time domain component axis_ofLowMeanWithLarger_fftPeak1_avg, we can determine it as follows: axis_ofLowMeanWithLarger_fftPeak1_avg=(x, y,z) [orderOfLowMeanWithLarger_fftPeak1_avg], wherein (x,y,z) are the time domain components of the accelerometer signal (e.g. in an example of embodiment, each time domain component of the accelerometer (x,y,z) stores 186 samples); other embodiments may use arrays instead of tuples for the determining:
axis_ofLowMeanWithLarger_fftPeak1_avg=array([x,y,z]) [orderOfLowMeanWithLarger_fftPeak1_avg]; substep B) next we obtain the autocorrelation signal of said accelerometer component: corr_form_ofLowMeanWithLarger_fftPeak1_ avg=find_autocorrelation_form (axis_ofLowMeanWithLarger_fftPeak1_avg); substep C) next we determine an index of a secondary maximum with a largest amplitude in said autocorrelation signal; we can call it peak1_ofLowMeanWithLarger_fftPeak1_avg, and we can compute it as follows: peak1_ofLowMeanWithLarger_ fftPeak1_avg=argmax (corr_form_ofLowMeanWithLarger_ fftPeak1_avg [low_edge:high_edge])+low_edge; As used herein, the term "secondary maximum" is hereby defined to mean: a maximum obtained from an autocorrelation signal, said maximum being different from a central maximum in said autocorrelation signal; please remember that performing an autocorrelation of an accelerometer signal over a time window, delivers another signal (for clarity purposes, called second signal, or autocorrelation signal, which typically consists of a central maximum surrounded by secondary minima and secondary maxima), from which the inverse of the time distance between the central maximum of said second signal and the largest secondary maximum (or secondary maximum with a largest amplitude) of said second signal, represents an indication of the fundamental frequency. It is interesting to note that some embodiments may choose a low edge "low_edge" and a high edge "high_edge" to determine the secondary maximum depending on factors comprising: a determined gait velocity of the user (e.g. higher velocities involving lower edges, and lower velocities involving higher edges), a shape of the autocorrelation signal (e.g. how the central maximum of the autocorrelation signal compares with the secondary maxima, in such a way that a very broad central maximum involves higher edges), and the suggested value of cadence (e.g. the suggested value of cadence, or some harmonic, should fall within the chosen edges); in an example of embodiment working with a determined gait velocity of the user of e.g. 0.9 mph, if the autocorrelation signal is processed to have 186 components (samples) on its right half, and we work with said right half, and the autocorrelation's central and secondary maxima have a similar width, and the suggested cadence is 0.5 Hz, we may choose low_edge=25 and high_edge=150 to determine index of the secondary maximum of largest amplitude of the autocorrelation signal; on another example, if the gait velocity of the user is 0.8 mph, and the central maximum of the autocorrelation signal is considerably larger than secondary maxima, and the suggested cadence is 0.4 Hz, we may choose low_edge=35 and high_edge=180; other embodiments may use different figures and/or approaches and/or techniques depending on different criteria, and/or any variations and/or combinations thereof; substep D) check if peak1_ofLowMeanWithLarger_fftPeak1_avg is within an expected range of values in agreement with the suggested value of cadence; for example, if the suggested value of cadence would suggest the index of the secondary maximum with largest amplitude in the autocorrelation to be at an index of e.g. suggested_index, we can check if peak1_ofLowMeanWithLarger_fftPeak1_avg is within e.g. 5% (or any other value) of suggested_index; by way of example, suggested_index may depend on different criteria and it could have values such as 40, 45, 50, 55, 60, or any other values depending on the specificities of each example of embodiment; some embodiments may use different values and/or approaches and/or techniques following different data and/or criteria and/or any other and/or any variations and/or combinations thereof. For example, if suggested_index is 40, some embodiment may check if an index of a secondary maximum with a largest amplitude in said autocorrelation signal is within a range of values such as 38, 39, 40, 41, 42. Consequently, Step 5 comprises: determining an autocorrelation of time domain data of an axis of an accelerometer, said axis being identified leveraging a comparison of absolute values of mean values, and determining if an index of a secondary maximum with a largest amplitude in said autocorrelation is within a range of values in agreement with the suggested value of cadence; wherein the index of the secondary maximum is determined using a low edge of 25 and a high edge of 150; wherein the index of the secondary maximum is determined using edges chosen in terms of factors comprising: a determined gait velocity of the user.

Regarding Step 5), some embodiments may relax the condition of peak1_ofLowMeanWithLarger_fftPeak1_avg being within an expected range (e.g. within 5%) in agreement with the suggested value of cadence, and instead allow a larger tolerance in the expected range (e.g. being within 30% or any other value) when the secondary maximum with largest amplitude in said autocorrelation signal (peak1_ofLowMeanWithLarger_fftPeak1_avg) satisfies the condition of being an "outstanding maximum". As used herein, the term "outstanding maximum" is hereby defined to mean: a secondary maximum obtained from an autocorrelation of a signal (e.g. an autocorrelation signal's secondary maximum with a largest amplitude), said secondary maximum positively satisfying the process described next, said process comprising the following steps: Step 5.1) determine an index of a secondary maximum with a largest amplitude of an autocorrelation signal; we can call it peak1, and it can be obtained as follows: peak1=argmax (autocorrelation_signal [low_edge:high_edge])+low_edge; Step 5.2) iterate to obtain a number of indexes of secondary maxima (largest amplitude) of the autocorrelation signal, different from the previously determined peak1; for example, we can obtain the next secondary maximum in said autocorrelation signal as follows: we obtain an auxiliary autocorrelation signal to prevent disrupting the original signal: autocorrelation_signal_aux=array ([c for c in autocorrelation_signal]); next, we compute the next secondary maximum (peak2) as follows: autocorrelation_signal_aux [peak1]=0; peak2=argmax (autocorrelation_signal_aux [low_edge:high_edge])+low_edge; we can iterative to obtain as many maxima as we wish; an example of an embodiment may determine 7 indexes of secondary maxima (peak1, peak2, peak3, peak4, peak5, peak6, peak7) while other embodiments may obtain different numbers of indexes of secondary maxima. Consequently, Step 5.2 determines indexes of the top 7 secondary maxima of largest amplitude from the autocorrelation signal. Step 5.3) determine a spread of the previously determined indexes of the top 7 secondary maxima; for example: we determine the smallest index as: smallest=min (peak1, peak2, peak3, peak4, peak5, peak6, peak7); and we determine the largest index as: largest=max (peak1, peak2, peak3, peak4, peak5, peak6, peak7); and we determine the spread of said indexes as: spread=largest−smallest; Step 5.4) determine a threshold to be compared at least with the previously determined spread; in some embodiments, said threshold may be determined based on the value of peak1 (e.g. proportionally increasing with peak1; e.g. threshold is 25% of peak1), while other embodiments may use more sophisticated approaches (including the use of conditionals to distinguish different cases; e.g. leveraging factors comprising peak1 and the largest index (largest)) depending on different criteria, and other embodiments may use any variations and/or combinations thereof. Step 5.5) compute the difference between the previously computed value of "largest" (computed in Step 5.3)), and the value of "2*peak1"; if said difference in relative terms (e.g. (largest−2*peak1)/(largest)) is less than a certain value (e.g. some embodiments may use 0.15 or 0.1 or any other similar value), and if the difference between peak1 and "smallest" is larger than the previously determined threshold, (peak1−smallest)>threshold, then the process is negatively satisfied and terminated; otherwise, the process continues as follows: Step 5.6) check if the previously determined spread is larger than the previously determined threshold; if so, the process is negatively satisfied and terminated; it is worth noting that some embodiments may add conditionals in this step taking into account different cases; other embodiments may use more sophisticated approaches and/or any variations and/or combinations thereof. Consequently, to summarize the steps described so far, in some embodiments, the process comprises: determining a threshold in terms of factors comprising an index of a secondary maximum with a largest amplitude; wherein said threshold is compared with a spread of a number of determined indexes of secondary maxima; wherein the number of determined indexes of secondary maxima is 7; and determining a difference between: a largest index of 7 indexes of secondary maxima, and a double of an index of a secondary maximum with a largest amplitude; and determining a difference between: an index of a secondary maximum with a largest amplitude, and a smallest index of 7 indexes of secondary maxima; and wherein said threshold is compared with said difference between: the index of the secondary maximum with the largest amplitude, and a smallest index of 7 indexes of secondary maxima. Step 5.7) having reached this point, without the process having been negatively satisfied and terminated previously, the process is positively satisfied and terminated; in other words, the maximum (secondary maximum with a largest amplitude) in said autocorrelation signal is an outstanding maximum. It is worth noting that some embodiments may add steps and/or conditionals to take into account different cases; other embodiments may use more sophisticated approaches and/or any variations and/or any combinations thereof. Consequently, in some embodiments, step 5 comprises: determining if a maximum in said autocorrelation signal is an outstanding maximum.

Step 6) check if the Fourier transform of the accelerometer axis identified in step 3, has an amplitude, at the frequency corresponding to the suggested cadence, larger than the amplitude, at the frequency corresponding to the suggested cadence, of the Fourier transform of the accelerometer axis different from the axis with highest mean in absolute value and different from the axis identified in step 3. This can be achieved by checking the following condition: (X_FFT, Y_FFT, Z_FFT) [orderOfLowMeanWithLarger_fftPeak1_avg] [cadence_frequency]>(X_FFT, Y_FFT, Z_FFT) [orderOfLowMeanWithSmaller_fftPeak1_avg] [cadence_frequency] wherein X_FFT, Y_FFT, Z_FFT represent Fourier transformations of the x, y, z axes of the accelerometer, cadence_frequency=0.5 Hz in this example of embodiment, and wherein orderOfLow- MeanWithSmaller_fftPeak1_avg corresponds to the order (0,1,2) of the accelerometer axis different from the axis with highest mean in absolute value and different from the axis identified in step 3; for example orderOfLowMean WithSmaller_fftPeak1_avg can be computed as follows: orderOfLowMeanWithSmaller_fftPeak1_avg=array([firstlowMeanOrder, secondlowMeanOrder]) [int(first- lowMean_fftPeak1_avg>secondlowMean_fftPeak1_avg)], or it can be computed using tuples instead of arrays: orderOfLowMeanWithSmaller_fftPeak1_avg=(firstlow- MeanOrder, secondlowMeanOrder) [int(firstlowMean_ fftPeak1_avg>secondlowMean_fftPeak1_avg)]. If the condition referred in this step 6 is satisfied, the method will support the suggested value of cadence (e.g. 0.5 Hz in this example of embodiment); on the other hand, or if any of the previous steps fails before arriving at step 6, the method will not support the suggested value of cadence. Consequently, step 6 comprises: checking if a Fourier transformation of an axis of an accelerometer, said axis being identified in step 3 leveraging a comparison of absolute values of mean values, has an amplitude, at a frequency corresponding to the suggested cadence, larger than an amplitude, at said frequency corresponding to the suggested cadence, of a Fourier transformation of an axis of the accelerometer, said axis being different from an axis with highest mean in absolute value and different from the axis identified in step 3. In other words, step 6 comprises: comparing an amplitude of a Fourier transformation of a first axis of an accelerometer, at a frequency corresponding to the suggested value of the cadence, with an amplitude of a Fourier transformation of a second axis of the accelerometer, at said frequency corresponding to the suggested value of the cadence.

It should be noted that, in some embodiments, any of the aspects and/or techniques and/or approaches and/or figures and/or elements and/or any others described throughout this Specification (or any others referenced) and/or any variations and/or combinations thereof can be combined simultaneously in any way for any purpose; for example, any of the aspects regarding supporting a suggested value of cadence can be used in any way to determine a gait cadence of the user while a user's representation of any kind is controlled in any way (e.g. with the determined gait cadence and/or any other attribute(s)), and any variations and/or combinations thereof are also possible.

Although the foregoing text sets forth a detailed description of numerous different embodiments of the invention, it should be understood that the scope of the invention is defined by the words of the claims set forth at the end of this patent. The detailed description is to be construed as exemplary only and does not describe every possibly embodiment of the invention because describing every possible embodiment would be impractical, if not impossible. Numerous alternative embodiments could be implemented, using either current technology or technology developed after the filing date of this patent, which would still fall within the scope of the claims defining the invention.

Thus, many modifications and variations may be made in the techniques and structures described and illustrated herein without departing from the spirit and scope of the present invention. Accordingly, it should be understood that the methods and apparatus described herein are illustrative only and are not limiting upon the scope of the invention.

The invention claimed is:

1. A computer-based method comprising:
   determining, by a mobile or wearable device carried by a user, a gait cadence of the user performing a gait motion, in real time; and
   controlling, by the mobile or wearable device, an aspect of an application in the mobile or wearable device based on the determined gait cadence, in real time;
   wherein said mobile or wearable device includes a motion sensor embedded therein; wherein the determining of the gait cadence comprises:
   obtaining a prior estimation of the gait cadence;
   obtaining an autocorrelation of time domain data along an axis of the motion sensor, wherein the autocorrelation presents a first maximum and other maxima;
   determining that a first kinematic value representative of a time distance between one of the other maxima and the first maximum is within a range of numbers; wherein the range of numbers is determined based on the prior estimation of the gait cadence; wherein an inverse of said time distance represents an estimation of the cadence; wherein said numbers indicate time distances from said first maximum, and constrain a second kinematic value representative of an inverse of the prior estimation of the cadence; and
   determining the gait cadence as the prior estimation of the gait cadence.

2. The method of claim 1, further comprising:
   determining a threshold using the first kinematic value representative of the time distance between the one of the other maxima and the first maximum;
   determining that said threshold is larger than a spread of a plurality of determined kinematic values representative of time distances between some of the other maxima and the first maximum of said auto correlation;
   wherein the some of the other maxima comprise the one of the other maxima.

3. The method of claim 2, wherein the threshold is larger than 20% of the first kinematic value representative of the time distance between the one of the other maxima and the first maximum.

4. The method of claim 2, wherein the threshold is proportional to the first kinematic value representative of the time distance between the one of the other maxima and the first maximum; wherein the plurality of determined kinematic values representative of time distances between the some of the other maxima and the first maximum comprise more than 2.

5. The method of claim 1, further comprising:
   determining a threshold using the first kinematic value representative of the time distance between the one of the other maxima and the first maximum;
   wherein the threshold is proportional to the first kinematic value representative of the time distance between the one of the other maxima and the first maximum; determining that said threshold is larger than a difference between: the first kinematic value representative of the time distance between the one of the other maxima and the first maximum, and a smallest kinematic value representative of time distance of a plurality of determined kinematic values representative of time distances between some of the other maxima and the first maximum of said autocorrelation; wherein the some of the other maxima comprise the one of the other maxima.

6. The method of claim 1, further comprising:
   determining a threshold using the first kinematic value representative of the time distance between the one of the other maxima and the first maximum;
   determining that said threshold is larger than a difference between: the first kinematic value representative of the time distance between the one of the other maxima and the first maximum, and a smallest kinematic value representative of time distance of a plurality of determined of kinematic values representative of time distances between some of the other maxima and the first maximum of said autocorrelation; wherein the some of the other maxima comprise the one of the other maxima.

7. The method of claim 1, wherein said axis of the motion sensor has been identified leveraging an average of frequencies of a maximum amplitude computed using a Fourier transformation.

8. The method of claim 1, wherein said axis of the motion sensor has been identified leveraging an average of frequencies of a maximum amplitude computed using a Fourier transformation; wherein said average has been computed over a time window.

9. The method of claim 8, wherein said axis of the motion sensor has been identified leveraging also a comparison of absolute values of mean values of time domain data along all axes of the motion sensor.

10. The method of claim 9, wherein said axis is different from an axis of the motion sensor with a highest value of said absolute values; wherein said axis of the motion sensor has been identified before the determining of the gait cadence.

11. The method of claim 9, further comprising:
determining that, in the identified axis, a frequency corresponding to a peak with a largest amplitude in a Fourier transformation, matches the prior estimation of the gait cadence.

12. The method of claim 1, wherein said axis is identified leveraging a comparison of absolute values of mean values of time domain data along all axes of the motion sensor; wherein said axis is different from an axis of the motion sensor with a highest value of said absolute values.

13. The method of claim 1, wherein said range of numbers span a percentage of one of said numbers; wherein the one of said numbers corresponds to the second kinematic value representative of the inverse of the prior estimation of the cadence; where said percentage is lower than 30%.

14. The method of claim 1, wherein the controlling the aspect of the application in the mobile or wearable device comprises:
controlling a cadence of a representation of the user based on the determined gait cadence, in real time.

15. The method of claim 2, wherein the motion sensor is an accelerometer; wherein the axis is identified leveraging a comparison of absolute values of mean values of time domain data along all axes of the accelerometer.

16. The method of claim 15, wherein said axis is different from an axis of the accelerometer with a highest value of said absolute values.

17. A system comprising:
a processor;
a processor-readable medium including instructions which, when executed by the processor, cause the processor to perform functions comprising:
determining a gait cadence of a user performing a gait motion and carrying a mobile or wearable device, in real time; and
controlling an aspect of an application in the mobile or wearable device based on the determined gait cadence, in real time; wherein said mobile or wearable device includes a motion sensor embedded therein; wherein the determining of the gait cadence comprises:
obtaining a prior estimation of the gait cadence;
obtaining an autocorrelation of time domain data along an axis of the motion sensor, wherein the autocorrelation presents a first maximum and other maxima;
determining that a first kinematic value representative of a time distance between one of the other maxima and the first maximum is within a range of numbers; wherein the range of numbers is determined based on the prior estimation of the gait cadence; wherein an inverse of said time distance represents an estimation of the cadence; wherein said numbers indicate time distances from said first maximum, and constrain a second kinematic value representative of an inverse of the prior estimation of the cadence; and
determining the gait cadence as the prior estimation of the gait cadence.

18. The system of claim 17, wherein the controlling the aspect of the application in the mobile or wearable device comprises: controlling a cadence of a representation of the user based on the determined gait cadence, in real time.

19. A non-transitory processor-readable medium including instructions which, when executed by a processor, cause the processor to perform functions comprising:
determining a gait cadence of a user performing a gait motion and carrying a mobile or wearable device, in real time; and
controlling an aspect of an application in the mobile or wearable device based on the determined gait cadence, in real time; wherein said mobile or wearable device includes a motion sensor embedded therein; wherein the determining of the gait cadence comprises:
obtaining a prior estimation of the gait cadence;
obtaining an autocorrelation of time domain data along an axis of the motion sensor, wherein the autocorrelation presents a first maximum and other maxima;
determining that a first kinematic value representative of a time distance between one of the other maxima and the first maximum is within a range of numbers; wherein the range of numbers is determined based on the prior estimation of the gait cadence; wherein an inverse of said time distance represents an estimation of the cadence; wherein said numbers indicate time distances from said first maximum, and constrain a second kinematic value representative of an inverse of the prior estimation of the cadence; and
determining the gait cadence as the prior estimation of the gait cadence.

20. The non-transitory processor-readable medium of claim 19, wherein the controlling the aspect of the application in the mobile or wearable device comprises: controlling a cadence of a representation of the user based on the determined gait cadence, in real time.

* * * * *